US012083027B2

(12) United States Patent
Nguyen et al.

(10) Patent No.: US 12,083,027 B2
(45) Date of Patent: Sep. 10, 2024

(54) UNIVERSAL FEMORAL TRIAL SYSTEM AND METHODS

(71) Applicant: Optimotion Implants LLC, Orlando, FL (US)

(72) Inventors: Vuong Binh Nguyen, Windermere, FL (US); Andrew Rynearson, Winter Springs, FL (US); Daniel F. Justin, Orlando, FL (US); Dinesh V. Koka, Winter Springs, FL (US)

(73) Assignee: Optimotion Implants LLC, Orlando, FL (US)

( * ) Notice: Subject to any disclaimer, the term of this patent is extended or adjusted under 35 U.S.C. 154(b) by 894 days.

(21) Appl. No.: 17/164,796

(22) Filed: Feb. 1, 2021

(65) Prior Publication Data
US 2021/0161681 A1    Jun. 3, 2021

Related U.S. Application Data

(63) Continuation-in-part of application No. 16/505,595, filed on Jul. 8, 2019, now Pat. No. 11,406,502, and a
(Continued)

(51) Int. Cl.
*A61B 17/17* (2006.01)
*A61B 17/15* (2006.01)
(Continued)

(52) U.S. Cl.
CPC ............ *A61F 2/4684* (2013.01); *A61B 17/17* (2013.01); *A61B 17/154* (2013.01); *A61B 17/157* (2013.01);
(Continued)

(58) Field of Classification Search
CPC ... A61B 17/157; A61B 17/16; A61B 17/1604; A61B 17/17; A61B 17/1675;
(Continued)

(56) References Cited

U.S. PATENT DOCUMENTS

| | | | |
|---|---|---|---|
| 4,257,129 A | 3/1981 | Volz | |
| 4,293,963 A | 10/1981 | Gold et al. | |

(Continued)

FOREIGN PATENT DOCUMENTS

| | | |
|---|---|---|
| CN | 101732761 | 6/2010 |
| GB | 2388034 | 11/2003 |

OTHER PUBLICATIONS

Blair et al., "Rapid Solid-State Synthesis of Titanium Aluminides", American Chemical Society, Chem Mater., Jan. 9, 2003 (8 pages).
(Continued)

*Primary Examiner* — Marcela I. Shirsat
(74) *Attorney, Agent, or Firm* — David Meibos; Maywood IP Law

(57) ABSTRACT

Implant assemblies, systems, kits, and methods for replacing a knee joint may include a universal femoral trial component for preparing and trialing a femoral bone of a patient to receive a plurality of different femoral implant types. The assembly may include a body and drill guide and an attachment mechanism including first and second compressible tabs and a rotatable handle operationally connected to the first and second tabs. The universal femoral trial component may be configured to receive any of a plurality of femoral bone preparation attachments and any of a plurality of femoral trial attachments in order to facilitate the preparation and trialing of the femoral bone to receive the plurality of different femoral implant types.

17 Claims, 53 Drawing Sheets

Related U.S. Application Data continuation-in-part of application No. 16/046,583, filed on Jul. 26, 2018, now Pat. No. 10,940,024, and a continuation-in-part of application No. 16/046,554, filed on Jul. 26, 2018, now Pat. No. 11,039,938, and a continuation-in-part of application No. 15/622,688, filed on Jun. 14, 2017, now Pat. No. 10,905,436.

(60) Provisional application No. 62/694,834, filed on Jul. 6, 2018, provisional application No. 62/537,106, filed on Jul. 26, 2017, provisional application No. 62/466,249, filed on Mar. 2, 2017.

(51) Int. Cl.
*A61B 17/16* (2006.01)
*A61F 2/46* (2006.01)
*A61F 2/30* (2006.01)
*A61F 2/38* (2006.01)

(52) U.S. Cl.
CPC ....... *A61B 17/1675* (2013.01); *A61B 17/1764* (2013.01); *A61F 2002/30331* (2013.01); *A61F 2002/305* (2013.01); *A61F 2002/30884* (2013.01); *A61F 2/3859* (2013.01); *A61F 2/389* (2013.01); *A61F 2/461* (2013.01)

(58) Field of Classification Search
CPC ..... A61B 17/15; A61B 17/155; A61B 17/154; A61B 17/1735; A61B 17/1739; A61B 17/1764; A61B 17/1767; A61F 2/3886; A61F 2/3859; A61F 2/385; A61F 2/46; A61F 2/461; A61F 2/4684; A61F 2/38; A61F 2/30734; A61F 2/389; A61F 2002/3863; A61F 2002/30604; A61F 2002/30607
USPC ... 606/879, 167, 184–185, 88, 86 R, 87, 96, 606/98, 99, 104, 86 B, 902, 915
See application file for complete search history.

(56) References Cited

U.S. PATENT DOCUMENTS

| | | |
|---|---|---|
| 4,323,756 A | 4/1982 | Brown et al. |
| 4,524,766 A | 6/1985 | Petersen |
| 4,659,331 A | 4/1987 | Matthews et al. |
| 4,714,474 A | 12/1987 | Brooks, Jr. et al. |
| 4,822,366 A | 4/1989 | Bolesky |
| 4,936,847 A | 6/1990 | Manginelli |
| 4,938,762 A | 7/1990 | Wehrli |
| 4,944,757 A | 7/1990 | Martinez et al. |
| 4,946,379 A | 8/1990 | Berchem |
| 4,950,298 A | 8/1990 | Gustilo et al. |
| 4,960,643 A | 10/1990 | Lemelson |
| 4,963,152 A | 10/1990 | Hofmann et al. |
| 5,007,933 A | 4/1991 | Sidebotham et al. |
| 5,047,058 A | 9/1991 | Roberts et al. |
| 5,059,216 A | 10/1991 | Winters |
| 5,100,409 A | 3/1992 | Coates et al. |
| 5,116,375 A | 5/1992 | Hofmann |
| 5,147,405 A | 9/1992 | Van Zile et al. |
| 5,176,684 A | 1/1993 | Ferrante et al. |
| 5,192,328 A | 3/1993 | Winters |
| 5,201,881 A | 4/1993 | Evans |
| 5,226,915 A | 7/1993 | Bertin |
| 5,330,534 A | 7/1994 | Herrington et al. |
| 5,354,414 A | 10/1994 | Feygin |
| 5,415,662 A | 5/1995 | Ferrante et al. |
| 5,531,793 A | 7/1996 | Kelman et al. |
| 5,549,685 A | 8/1996 | Hayes |
| 5,569,259 A | 10/1996 | Ferrante et al. |
| 5,609,645 A | 3/1997 | Vinciguerra |
| 5,653,714 A | 8/1997 | Dietz et al. |
| 5,658,334 A | 8/1997 | Caldarise et al. |
| 5,658,341 A | 8/1997 | Delfosse |
| 5,658,344 A | 8/1997 | Hurlburt |
| 5,672,284 A | 9/1997 | Devanathan et al. |
| 5,681,316 A | 10/1997 | DeOrio et al. |
| 5,683,397 A | 11/1997 | Vendrely et al. |
| 5,687,788 A | 11/1997 | Caldarise et al. |
| 5,702,460 A | 12/1997 | Carls et al. |
| 5,702,463 A | 12/1997 | Pothier et al. |
| 5,716,412 A | 2/1998 | DeCarlo, Jr. et al. |
| 5,755,808 A | 5/1998 | DeCarlo et al. |
| 5,762,125 A | 6/1998 | Mastrorio |
| 5,776,201 A | 7/1998 | Colleran et al. |
| 5,824,100 A | 10/1998 | Kester et al. |
| 5,824,103 A | 10/1998 | Williams |
| 5,879,393 A | 3/1999 | Whiteside et al. |
| 5,879,394 A | 3/1999 | Ashby et al. |
| 5,897,592 A | 4/1999 | Caldarise et al. |
| 5,910,173 A | 6/1999 | DeCarlo, Jr. et al. |
| 5,964,808 A | 10/1999 | Blaha et al. |
| 5,980,974 A | 11/1999 | Armini et al. |
| 6,004,352 A | 12/1999 | Buni |
| 6,074,424 A | 6/2000 | Perrone, Jr. et al. |
| 6,087,553 A | 7/2000 | Cohen et al. |
| 6,105,235 A | 8/2000 | Caldarise |
| 6,132,674 A | 10/2000 | Compton et al. |
| 6,165,221 A | 12/2000 | Schmotzer |
| 6,165,223 A | 12/2000 | Metzger et al. |
| 6,206,926 B1 | 3/2001 | Pappas |
| RE37,277 E | 7/2001 | Baldwin et al. |
| 6,258,127 B1 | 7/2001 | Schmotzer |
| 6,506,216 B1 | 1/2003 | McCue et al. |
| 6,652,588 B2 | 11/2003 | Hayes, Jr. et al. |
| 6,827,739 B2 | 12/2004 | Griner et al. |
| 6,858,032 B2 | 2/2005 | Chow et al. |
| 6,869,448 B2 | 3/2005 | Tuke et al. |
| 6,896,702 B2 | 5/2005 | Collazo |
| 6,916,340 B2 | 7/2005 | Metzger et al. |
| 6,923,832 B1 | 8/2005 | Sharkey et al. |
| 6,945,448 B2 | 9/2005 | Medlin et al. |
| 6,974,625 B2 | 12/2005 | Hunter et al. |
| 7,001,672 B2 | 2/2006 | Justin et al. |
| 7,048,741 B2 | 5/2006 | Swanson |
| 7,081,137 B1 | 7/2006 | Servidio |
| 7,087,200 B2 | 8/2006 | Taboas et al. |
| 7,105,030 B2 | 9/2006 | Despres, III et al. |
| 7,160,330 B2 | 1/2007 | Axelson, Jr. et al. |
| 7,175,665 B2 | 2/2007 | German et al. |
| 7,182,786 B2 | 2/2007 | Justin et al. |
| 7,189,262 B2 | 3/2007 | Hayes, Jr. et al. |
| 7,258,810 B2 | 8/2007 | Hunter et al. |
| 7,294,149 B2 | 11/2007 | Hozack et al. |
| 7,309,339 B2 | 12/2007 | Cusick et al. |
| 7,357,817 B2 | 4/2008 | D'Alessio, II |
| 7,413,577 B1 | 8/2008 | Servidio |
| 7,445,640 B2 | 11/2008 | Despres, III et al. |
| 7,497,874 B1 | 3/2009 | Metzger et al. |
| 7,513,912 B2 | 4/2009 | Hayes, Jr. et al. |
| 7,524,334 B2 | 4/2009 | Haidukewych |
| 7,537,664 B2 | 5/2009 | O'Neill et al. |
| 7,578,851 B2 | 8/2009 | Dong et al. |
| 7,625,407 B2 | 12/2009 | Akizuki et al. |
| 7,628,817 B1 | 12/2009 | Axelson, Jr. et al. |
| 7,632,575 B2 | 12/2009 | Justin et al. |
| 7,648,735 B2 | 1/2010 | Hunter et al. |
| 7,666,522 B2 | 2/2010 | Justin et al. |
| 7,771,484 B2 | 8/2010 | Campbell |
| 7,837,690 B2 | 11/2010 | Metzger |
| 7,842,092 B2 | 11/2010 | Otto et al. |
| 7,850,862 B2 | 12/2010 | Amrich et al. |
| 7,857,858 B2 | 12/2010 | Justin et al. |
| 7,883,510 B2 | 2/2011 | Kim et al. |
| 7,887,542 B2 | 2/2011 | Metzger et al. |
| 7,918,382 B2 | 4/2011 | Charlebois et al. |
| 7,938,833 B2 | 5/2011 | Bastian |
| 7,963,968 B2 | 6/2011 | Dees, Jr. |
| 8,038,681 B2 | 10/2011 | Koenemann |
| 8,070,821 B2 | 12/2011 | Roger |
| 8,075,628 B2 | 12/2011 | Justin et al. |

(56) References Cited

U.S. PATENT DOCUMENTS

| | | |
|---|---|---|
| 8,142,886 B2 | 3/2012 | Noble et al. |
| 8,147,861 B2 | 4/2012 | Jones et al. |
| 8,162,949 B2 | 4/2012 | Duggineni et al. |
| 8,167,954 B2 | 5/2012 | Despres, III et al. |
| 8,187,335 B2 | 5/2012 | Wyss et al. |
| 8,191,760 B2 | 6/2012 | Charlebois et al. |
| 8,192,498 B2 | 6/2012 | Wagner et al. |
| 8,236,061 B2 | 8/2012 | Heldreth et al. |
| 8,241,367 B2 | 8/2012 | Justin et al. |
| 8,268,006 B2 | 9/2012 | Meyers et al. |
| 8,268,099 B2 | 9/2012 | O'Neill et al. |
| 8,268,100 B2 | 9/2012 | O'Neill et al. |
| 8,350,186 B2 | 1/2013 | Jones et al. |
| 8,357,201 B2 | 1/2013 | Mayer et al. |
| 8,388,887 B2 | 3/2013 | Gupta et al. |
| 8,403,992 B2 | 3/2013 | Otto et al. |
| 8,403,994 B2 | 3/2013 | Maloney et al. |
| 8,414,908 B2 | 4/2013 | Jin et al. |
| 8,449,618 B2 | 5/2013 | Otto et al. |
| 8,518,047 B2 | 8/2013 | Metzger et al. |
| 8,551,100 B2 | 10/2013 | Metzger |
| 8,556,981 B2 | 10/2013 | Jones et al. |
| 8,562,688 B2 | 10/2013 | Belcher |
| 8,603,178 B2 | 12/2013 | Otto et al. |
| 8,632,600 B2 | 1/2014 | Zannis et al. |
| 8,663,337 B2 | 3/2014 | Anderson et al. |
| 8,668,743 B2 | 3/2014 | Perler |
| 8,690,954 B2 | 4/2014 | Parisi et al. |
| 8,702,803 B2 | 4/2014 | Otto et al. |
| 8,715,359 B2 | 5/2014 | Deffenbaugh et al. |
| 8,728,387 B2 | 5/2014 | Jones et al. |
| 8,735,773 B2 | 5/2014 | Lang |
| 8,758,444 B2 | 6/2014 | Wentorf et al. |
| 8,764,759 B2 | 7/2014 | Dees, Jr. |
| 8,771,280 B2 | 7/2014 | Bailey et al. |
| 8,784,496 B2 | 7/2014 | Wagner et al. |
| 8,790,345 B2 | 7/2014 | Anderson |
| 8,795,380 B2 | 8/2014 | Heldreth et al. |
| 8,828,086 B2 | 9/2014 | Williams et al. |
| 8,834,575 B2 | 9/2014 | Wyss et al. |
| 8,843,229 B2 | 9/2014 | Vanasse et al. |
| 8,870,883 B2 | 10/2014 | Metzger et al. |
| 8,900,315 B2 | 12/2014 | Lipman et al. |
| 8,900,316 B2 | 12/2014 | Lenz et al. |
| 8,900,317 B2 | 12/2014 | Zubok et al. |
| 8,951,465 B2 | 2/2015 | Gupta |
| 8,968,413 B2 | 3/2015 | Cook et al. |
| 8,979,847 B2 | 3/2015 | Belcher et al. |
| 8,985,430 B2 | 3/2015 | Charlebois et al. |
| 8,986,310 B2 | 3/2015 | Bailey et al. |
| 8,992,703 B2 | 3/2015 | O'Neill et al. |
| 9,023,053 B2 | 5/2015 | Metzger |
| 9,044,249 B2 | 6/2015 | Dees, Jr. |
| 9,072,605 B2 | 7/2015 | Coon et al. |
| 9,119,734 B2 | 9/2015 | Dees |
| 9,149,287 B2 | 10/2015 | Bailey et al. |
| 9,161,761 B2 | 10/2015 | Metzger et al. |
| 9,186,255 B2 | 11/2015 | Parisi et al. |
| 9,192,459 B2 | 11/2015 | Bonutti |
| 9,220,601 B2 | 12/2015 | Williams et al. |
| 9,226,827 B2 | 1/2016 | Luscher |
| 9,237,950 B2 | 1/2016 | Hensley et al. |
| 9,265,613 B2 | 2/2016 | Nevins et al. |
| 9,278,003 B2 | 3/2016 | Deffenbaugh et al. |
| 9,287,301 B2 | 3/2016 | Tohyama |
| 9,301,846 B2 | 4/2016 | Landon |
| 9,320,605 B2 | 4/2016 | Otto et al. |
| 9,326,864 B2 | 5/2016 | Wyss et al. |
| 9,370,605 B2 | 6/2016 | Zhang et al. |
| 9,381,085 B2 | 7/2016 | Axelson, Jr. et al. |
| 9,387,084 B2 | 7/2016 | Masini et al. |
| 9,402,729 B2 | 8/2016 | Otto et al. |
| 9,408,699 B2 | 8/2016 | Stalcup et al. |
| 9,427,334 B2 | 8/2016 | Axelson, Jr. et al. |
| 9,445,823 B2 | 9/2016 | Harris et al. |
| 9,445,902 B2 | 9/2016 | Klein et al. |
| 9,445,909 B2 | 9/2016 | Cohen et al. |
| 9,452,051 B2 | 9/2016 | Collazo et al. |
| 9,452,053 B2 | 9/2016 | Wagner et al. |
| 9,456,901 B2 | 10/2016 | Jones et al. |
| 9,480,511 B2 | 11/2016 | Butters et al. |
| 9,517,134 B2 | 12/2016 | Lang |
| 9,517,138 B2 | 12/2016 | Zubok et al. |
| 9,539,099 B2 | 1/2017 | Heldreth et al. |
| 9,554,862 B2 | 1/2017 | Davignon et al. |
| 9,566,161 B2 | 2/2017 | Hartdegen et al. |
| 9,579,210 B2 | 2/2017 | Wong |
| 9,636,229 B2 | 5/2017 | Lang et al. |
| 9,642,711 B2 | 5/2017 | Carson |
| 9,649,195 B2 | 5/2017 | Bechtold et al. |
| 9,649,205 B2 | 5/2017 | Dees, Jr. |
| 9,655,632 B2 | 5/2017 | Dmuschewsky et al. |
| 9,655,728 B2 | 5/2017 | Parisi et al. |
| 9,655,729 B2 | 5/2017 | Parisi et al. |
| 9,656,358 B2 | 5/2017 | Charlebois et al. |
| 9,662,214 B2 | 5/2017 | Li et al. |
| 9,668,863 B2 | 6/2017 | Sharp et al. |
| 9,668,871 B2 | 6/2017 | Irwin et al. |
| 9,693,788 B2 | 7/2017 | Metzger |
| 9,693,869 B2 | 7/2017 | Salehi et al. |
| 9,717,598 B2 | 8/2017 | Otto |
| 9,763,794 B2 | 9/2017 | Sanford et al. |
| 9,770,345 B2 | 9/2017 | Belcher et al. |
| 9,788,954 B2 | 10/2017 | Parisi et al. |
| 9,839,522 B2 | 12/2017 | Bechtold et al. |
| 9,918,845 B2 | 3/2018 | Roby et al. |
| 9,931,216 B2 | 4/2018 | Williams et al. |
| 9,937,049 B2 | 4/2018 | Wyss et al. |
| 10,940,024 B2 * | 3/2021 | Nguyen .................. A61F 2/389 |
| 2002/0082741 A1 | 6/2002 | Mazumder et al. |
| 2002/0198529 A1 | 12/2002 | Masini |
| 2004/0039395 A1 | 2/2004 | Coon et al. |
| 2004/0191106 A1 | 9/2004 | O'Neill et al. |
| 2006/0106388 A1 | 5/2006 | Lococo |
| 2006/0147332 A1 | 7/2006 | Jones et al. |
| 2006/0229715 A1 | 10/2006 | Istephanous et al. |
| 2007/0100461 A1 | 5/2007 | Incavo |
| 2007/0142914 A1 | 6/2007 | Jones et al. |
| 2008/0004709 A1 | 1/2008 | O'Neill |
| 2008/0215157 A1 | 9/2008 | Earl et al. |
| 2008/0243258 A1 | 10/2008 | Sancheti |
| 2010/0016980 A1 | 1/2010 | Donno et al. |
| 2010/0016987 A1 | 1/2010 | Scrafton et al. |
| 2010/0305708 A1 | 12/2010 | Lang et al. |
| 2010/0318089 A1 | 12/2010 | Metzger et al. |
| 2011/0029093 A1 | 2/2011 | Bojarski et al. |
| 2011/0230973 A1 | 9/2011 | Hippensteel et al. |
| 2012/0041564 A1 | 2/2012 | Landon |
| 2012/0116524 A1 | 5/2012 | Walker et al. |
| 2012/0191204 A1 | 7/2012 | Bae et al. |
| 2012/0239098 A1 | 9/2012 | Bae et al. |
| 2013/0006374 A1 | 1/2013 | Le Couedic et al. |
| 2013/0144293 A1 * | 6/2013 | Wilkinson ............. A61B 17/16 606/88 |
| 2013/0173010 A1 | 7/2013 | Irwin et al. |
| 2013/0218288 A1 | 8/2013 | Fonte et al. |
| 2014/0010951 A1 | 1/2014 | Vargas et al. |
| 2014/0257504 A1 | 9/2014 | Dong et al. |
| 2014/0257507 A1 | 9/2014 | Wang et al. |
| 2014/0277530 A1 | 9/2014 | Stalcup |
| 2014/0277540 A1 | 9/2014 | Leszko et al. |
| 2014/0277548 A1 | 9/2014 | Cohen et al. |
| 2014/0316528 A1 | 10/2014 | Bechtold et al. |
| 2014/0371863 A1 | 12/2014 | Vanasse et al. |
| 2015/0032218 A1 | 1/2015 | Landon |
| 2015/0093283 A1 | 4/2015 | Miller et al. |
| 2015/0257900 A1 | 9/2015 | Dees, Jr. |
| 2015/0258735 A1 | 9/2015 | O'Neill et al. |
| 2015/0305754 A1 | 10/2015 | Metzger |
| 2015/0305878 A1 | 10/2015 | O'Neil et al. |
| 2015/0342741 A1 | 12/2015 | Davignon et al. |
| 2015/0342742 A1 | 12/2015 | Ferro et al. |
| 2015/0359638 A1 | 12/2015 | Khowaylo et al. |
| 2016/0015520 A1 | 1/2016 | Smith et al. |

(56) References Cited

U.S. PATENT DOCUMENTS

| | | |
|---|---|---|
| 2016/0157906 A1 | 6/2016 | Hollis et al. |
| 2016/0157908 A1 | 6/2016 | Cawley et al. |
| 2016/0199193 A1 | 7/2016 | Willis et al. |
| 2016/0213821 A1 | 7/2016 | Melkent et al. |
| 2016/0228255 A1 | 8/2016 | Samuelson et al. |
| 2016/0278929 A1 | 9/2016 | Harris et al. |
| 2016/0296289 A1 | 10/2016 | Choudhury et al. |
| 2016/0310279 A1 | 10/2016 | Samuelson et al. |
| 2016/0310282 A1 | 10/2016 | Bojarski et al. |
| 2017/0014235 A1 | 1/2017 | Jones et al. |
| 2017/0027700 A1 | 2/2017 | Cohen et al. |
| 2017/0035572 A1 | 2/2017 | Servidio |
| 2017/0042576 A1 | 2/2017 | Butters et al. |
| 2017/0056025 A1 | 3/2017 | Trachsler et al. |
| 2017/0071744 A1 | 3/2017 | Bali et al. |
| 2017/0209279 A1 | 7/2017 | Leszko et al. |
| 2017/0312084 A1 | 11/2017 | Ferro et al. |
| 2017/0333209 A1 | 11/2017 | Tsukayama et al. |
| 2018/0028325 A1 | 2/2018 | Bojarski et al. |
| 2018/0049880 A1 | 2/2018 | Sun et al. |
| 2018/0065324 A1 | 3/2018 | Isobe et al. |
| 2018/0161167 A1 | 6/2018 | Bae et al. |
| 2018/0250022 A1 | 9/2018 | Nguyen et al. |
| 2018/0250134 A1 | 9/2018 | Justin et al. |
| 2020/0085592 A1* | 3/2020 | Oh .................. A61F 2/4684 |

OTHER PUBLICATIONS

Restrepo et al., Size Controlled Mechanochemical Synthesis of ZrSi2, The Royal Society of Chemistry, ChemComm, Aug. 30, 2012 (3 pages).
Bone Ingrowth Performance of OsteoSync Ti, Sites Medical Research and Development, Document: 2007-001-40 REV A (5 pages).
Mechanical Characteristics of OsteoSync Ti, Sites Medical Research and Development, Document: 2007-001-41 REV A (4 pages).
International Search Report and Written Opinion dated May 31, 2018 for corresponding PCT Application No. PCT/US2018/019652.
Reference U, DePuy, Knee Revision Reference Cards, published May 2009 (65 pages).
Reference V, Conformis, Comformis Launches Next Generation of Only Patient-Specific Total Knee Replacement Implant System Available on Market, published Oct. 3, 2012 (6 pages).
Reference W, Smith & Nephew, Legion Total Knee System, Apr. 2015 (8 pgs).
Reference X, Smith & Nephew, Journey II TKA Total Knee System, Nov. 2013 (68 pages).

* cited by examiner

|  | Cruciate Retaining Insert | Posterior Stabilizing Insert | Constrained Condylar Knee Insert |
|---|---|---|---|
| Cruciate Retaining Femoral Component | X | X | X |
| Posterior Stabilizing Femoral Component | X | X | X |

Fig. 13

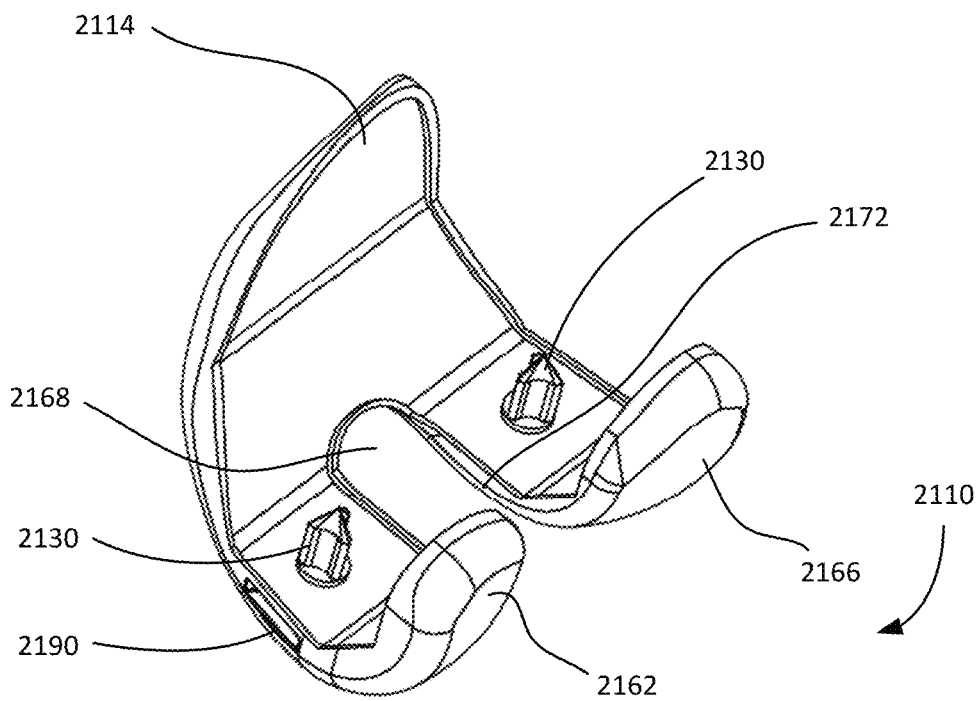
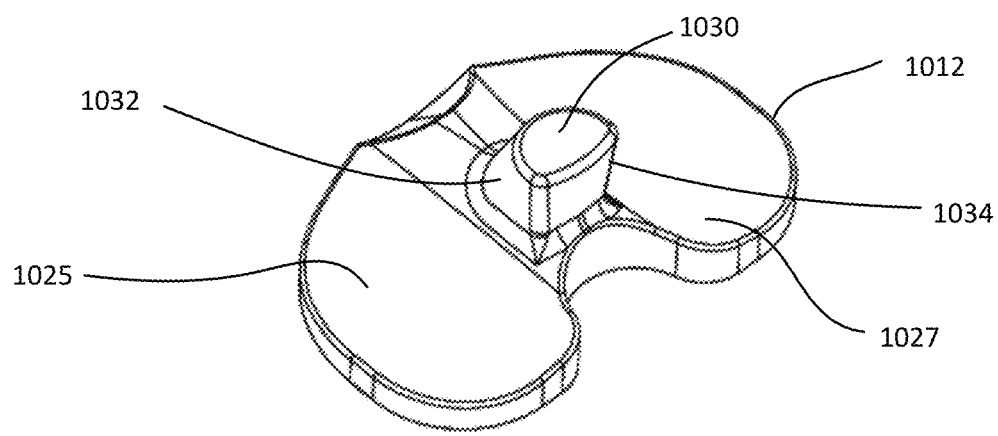
Fig. 20

↙ 4000

```
┌─────────────────────────────────────────────────────────────┐
│ Accessing A First Knee Joint Prosthesis Assembly Comprising │
│ A First Tibial Insert Between A Tibial Base Plate And A     │
│ Femoral Component                                            │
│                          4010                                │
└─────────────────────────────────────────────────────────────┘
                              │
                              ▼
┌─────────────────────────────────────────────────────────────┐
│ Removing The First Tibial Insert From Between The Tibial    │
│ Baseplate Component And The Femoral Component                │
│                          4020                                │
└─────────────────────────────────────────────────────────────┘
                              │
                              ▼
┌─────────────────────────────────────────────────────────────┐
│ Inserting A Second Tibial Insert Between The Tibial Baseplate│
│ Component And The Femoral Component To Create A Second Knee │
│ Joint Prosthesis Assembly That Is More Constrained Than The │
│ First Knee Joint Prosthesis Assembly                         │
│                          4030                                │
└─────────────────────────────────────────────────────────────┘
```

Fig. 37

UNIVERSAL FEMORAL TRIAL SYSTEM AND METHODS

CROSS-REFERENCE TO RELATED APPLICATIONS

The present application is a continuation-in-part of U.S. patent application Ser. No. 15/622,688 filed on Jun. 14, 2017, entitled KNEE ARTHROPLASTY SYSTEMS AND METHODS, which claims the benefit of U.S. Provisional Application No. 62/466,249 filed on Mar. 2, 2017, entitled COMPOSITE JOINT ARTHROPLASTY SYSTEMS AND METHODS. The present application is also a continuation-in-part of U.S. patent application Ser. No. 16/046,554 filed on Jul. 26, 2018, entitled MODULAR KNEE PROSTHESIS, which claims the benefit of U.S. Provisional Application No. 62/537,106 filed on Jul. 26, 2017, entitled MODULAR KNEE PROSTHESIS. The present application is also a continuation-in-part of U.S. patent application Ser. No. 16/505,595 filed on Jul. 8, 2019, entitled ORTHOPEDIC IMPLANTS AND METHODS, which claims the benefit of U.S. Provisional Application No. 62/694,834 filed on Jul. 6, 2018, entitled ORTHOPEDIC IMPLANTS AND METHODS. The present application is also a continuation-in-part of U.S. patent application Ser. No. 16/046,583 filed on Jul. 26, 2018, entitled UNIVERSAL FEMORAL TRIAL SYSTEM AND METHODS, which claims the benefit of U.S. Provisional Application No. 62/537,106 filed on Jul. 26, 2017, entitled MODULAR KNEE PROSTHESIS. The above-referenced applications are incorporated by reference as though set forth herein in their entirety.

TECHNICAL FIELD

The present disclosure relates to surgical devices, systems, instruments, and methods. More specifically, the present disclosure relates to orthopedic knee replacement surgical devices, instruments, systems, and methods.

BACKGROUND

A number of knee replacement options exist which may be implemented depending upon the level of compromise of the natural knee anatomy. The knee anatomy complex includes the knee joint between the femur distal end and the tibia proximal end, and the surrounding anterior and posterior cruciate ligaments (ACL, PCL), and medial and lateral collateral ligaments (MCL, LCL), which provide support and stabilization to the knee joint. When one or more ligaments are compromised, for example through injury, disease, or aging, a knee prosthesis system may be implanted to replace the knee joint.

In a situation where the anterior cruciate ligament is compromised, it may be removed and a cruciate retaining (CR) knee prosthesis system, which allows retention of the posterior cruciate ligament and the collateral ligaments, may be implanted. Typical CR knee prosthesis femoral components and tibial inserts have large U-shaped openings providing room for the extant PCL, MCL, and LCL ligaments.

In a case where both the anterior and posterior cruciate ligaments are compromised but, yet the collateral ligaments are functional, both the ACL and PCL may be removed, and a posterior stabilizing (PS) knee prosthesis system may be implanted. A typical PS tibial insert includes a central post, and many PS femoral components include a cam element extending between the medial and lateral condyles. The post and cam interact to provide stability in place of the removed PCL ligament.

In a case where the anterior and posterior cruciate ligaments are compromised, and the collateral ligaments are unstable, both the ACL and PCL may be removed and a constrained condylar knee (CCK) prosthesis system may be implanted. In a case where all four ligaments are compromised, all ligaments may be removed, and a hinge type knee replacement system may be implanted.

A typical knee prosthesis system includes a tibial bone anchoring component, a tibial articulating component, which may be called a tibial insert, and a femoral bone anchoring component. Since the tibial and femoral bone anchoring components are anchored to bone through various fasteners, cement, and/o bone ingrowth, it may be difficult and invasive to remove and replace either of the bone anchoring components, should the need arise. The tibial insert is typically made of polyethylene, and since it is not anchored to bone, is much more easily replaced if necessary. For example, a patient may have a CR knee prosthesis and then experience compromise of the PCL, thus requiring replacement of the CR knee prosthesis with a PS knee prosthesis. Or, a patient may have a PS knee prosthesis and then experience instability of the collateral ligaments, thus requiring replacement of the PS knee prosthesis with a CCK prosthesis.

SUMMARY

The various systems and methods of the present disclosure have been developed in response to the present state of the art, and in particular, in response to the problems and needs in the art that have not yet been fully solved by currently available technology.

In an embodiment, an assembly for facilitating orthopedic surgery may include a body with a drill guide connected to the body and an attachment mechanism connected to the body. The attachment mechanism may include a first tab, a second tab, and a handle connected to the first and second tabs. The rotation of the handle about an axis may cause the first and second tabs to extend outward from the body to secure the body to an external frame secured to a patient. The drill guide may further include at least one drill guide aperture that extends through the drill guide and through the body. The drill guide may further include at least one broach guide aperture that extends through the drill guide and through the body. The at least one drill guide aperture may be in communication with the at least one broach guide aperture.

The first tab and the second tab each may have a proximal end and a distal end, and the proximal ends of the tabs may be adjacent to one another and the distal ends of the tabs may extend away from each other. The proximal ends of the tabs may each have a handle attachment feature and the handle may further include tab attachment features complementary to the handle attachment features on each of the tabs. The rotation of the handle about the axis may cause each of the first tab and the second tab to transition between a retracted position and an extended position, relative to the body. The proximal ends of the first and second tabs may be located within a cavity in the body so that the handle attachment features and/or the tab attachment features extend into the cavity. At least one of the first tab and the second tab may further include a stop member and the body may further include an abutment member. The rotation of the handle may cause the stop member to engage the abutment member to retain the at least one of the first tab and the second tab in the extended position.

The first and the second tabs each may have a proximal end, a distal end, and an intermediate section therebetween. The intermediate section may be compressible such that the proximal end and the distal end are configured to be translatable. The assembly may further include the external frame which may be a trial component for joint arthroplasty. The first and second tabs each may have a proximal end, a distal end, and an intermediate section therebetween. The trial component may have a receiving aperture shaped to receive the body and locking apertures, in communication with the receiving aperture, shaped to receive the distal ends of the first tab and the second tab when the handle is rotated with the body positioned in the receiving aperture.

In an embodiment, an assembly may include a body, and a drill and broach guide. The drill and broach guide may include a first drill guide aperture, a second drill guide aperture, a third drill guide aperture, a first broach guide aperture intermediate the first drill guide aperture and the second drill guide aperture, and a second broach guide aperture intermediate the second drill guide aperture and the third drill guide aperture. The second drill guide aperture may be intermediate the first broach guide aperture and the second broach guide aperture. The assembly may have a locking mechanism including a handle connected to the body such that the handle is rotatable about an axis, a first tab having a first proximal end, a first distal end, and a first compressible intermediate section. The first proximal end may have a first handle connection feature, a second tab having a second proximal end, a second distal end, and a second compressible intermediate section. The second proximal end may have a second handle connection feature. The handle may be movably connected to the first handle connection feature and the second handle connection feature such that rotation of the handle about the axis extends the first and second tabs outward from the body.

The first and second tabs may be located within a cavity in the body. At least one of the first tab and the second tab may further have a stop member. The body may further have an abutment member. Rotation of the handle may cause the stop member to engage the abutment member to retain the at least one of the first tab and the second tab in the extended position. The handle may further have a circular base and a grip portion. The circular base may have a concave surface. The body may further have an aperture, surrounding the axis, extending from a first surface of the body to a second surface of the body. The circular base may engage the aperture. The handle may be rotatably secured to the base at the aperture by two pins extending into the base proximate an edge of the aperture, so that the pins securely engage the concave surface, allowing the handle to rotate about the axis.

The assembly may further include an external frame, which may be a trial component for joint arthroplasty. The trial component may further have a receiving aperture shaped to receive the body and locking apertures, in communication with the receiving aperture, shaped to receive the first and second distal ends of the first tab and the second tab when the handle is rotated with the body positioned in the receiving aperture.

In an embodiment, an assembly for preparing and trialing a bone to receive an implant, may include a body, a drill guide connected to the body, and an attachment mechanism connected to the body. The attachment mechanism may further include a first tab, a second tab, and a handle connected to the first and second tabs. The assembly may be configured to be removably coupled to a trial component by rotating the handle such that the first tab and the second tab are first in the retracted position, positioning the assembly adjacent to the trial component, and rotating the handle such that the first tab and the second tab move to the extended position and engage within corresponding attachment apertures in the trial component. At least one of the first tab and the second tab may further include a stop member and the body may further have an abutment member. The rotation of the handle may cause the stop member to engage the abutment member to retain the at least one of the first tab and second tab in in the extended position or a retracted position.

The first and the second tabs each may have a proximal end, a distal end, and an intermediate section therebetween. The handle may engage the first tab and the second tab at the proximal ends. The intermediate section may be compressible, and the handle may be rotatable to transition the first and second tabs to the extended position so that the distal ends of the first and second tabs enter the corresponding attachment apertures in the trial component. The intermediate section may be compressible such that, in response to the distal ends abutting a surface, the intermediate section is compressed to urge the stop member against the abutment member and prevents rotation of the handle. The distal ends may be configured to abut a surface and cause a compression of the intermediate section. The compression may urge the stop member against the abutment member and prevent rotation of the handle. The assembly may further include the external frame. The external frame may be a trial component for joint arthroplasty and may further include a receiving aperture shaped to receive the body. The first and second tabs may each have a proximal end, a distal end, and an intermediate section therebetween. The frame may further have locking apertures, in communication with the receiving aperture, shaped to receive the distal ends of the first tab and the second tab when the handle is rotated with the body positioned in the receiving aperture.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIG. 13 is a chart demonstrating the interchangeability of the tibial inserts disclosed herein with various femoral components;

FIG. 20 is another exploded rear view of the assembly of FIG. 19;

FIG. 37 is a flow chart diagram of a method for revising a knee joint prosthesis to provide increased stability;

It is to be understood that the drawings are for purposes of illustrating the concepts of the disclosure and may not be to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, instruments, systems, and methods, as represented in the Figures, is not intended to limit the scope of the disclosure, as claimed, but is merely representative of exemplary embodiments of the disclosure.

Disclosed herein are components for a modular knee prosthesis system. This system may allow for revision procedures by replacement of only the tibial insert, allowing the originally implanted femoral and tibial anchoring components to remain implanted. The system may include CR tibial inserts, PS tibial inserts, and/or CCK tibial inserts. Any one of these tibial inserts may be interchangeably used with CR and/or PS femoral components disclosed herein to provide the stabilization needed to substitute for compromised or removed ligaments. The system may be used with any suitable tibial baseplate component, or tibial tray, to support the tibial insert. The PS tibial inserts disclosed herein may include tapered posts that permit the inserts to be used with cruciate retaining (CR) femoral components and/or posterior stabilizing (PS) femoral components.

Figure 1A:
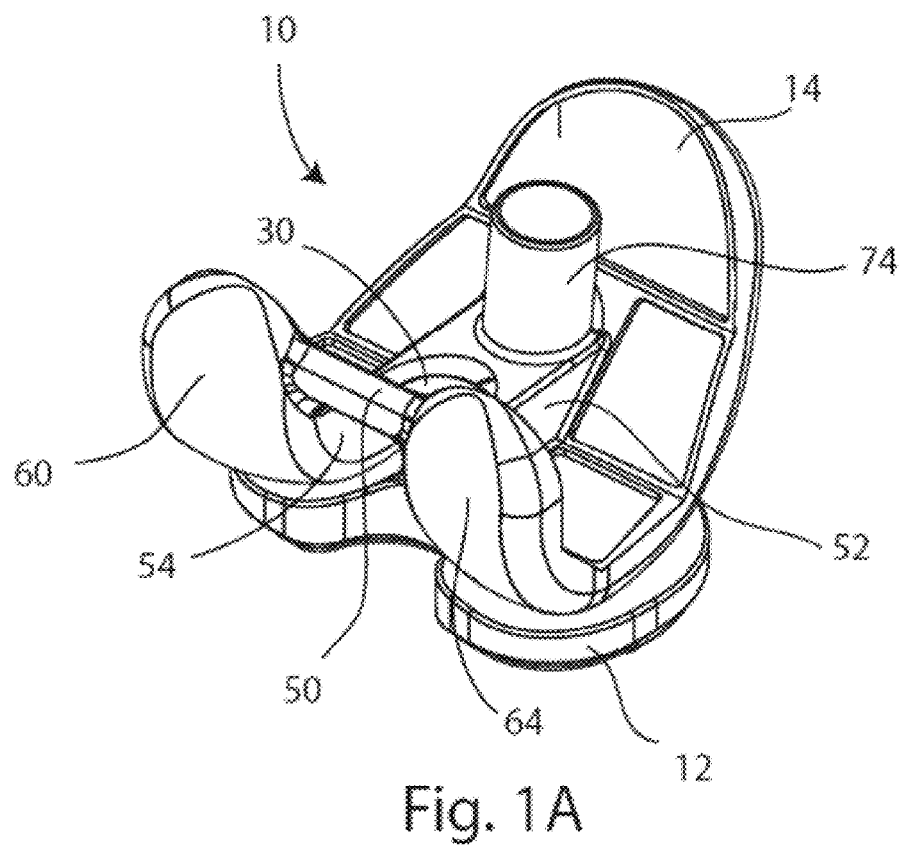
FIG. 1A is a perspective rear view of an assembly of the disclosure, including a posterior stabilizing femoral component and a tibial insert coupled in extension.
Figure 1B:
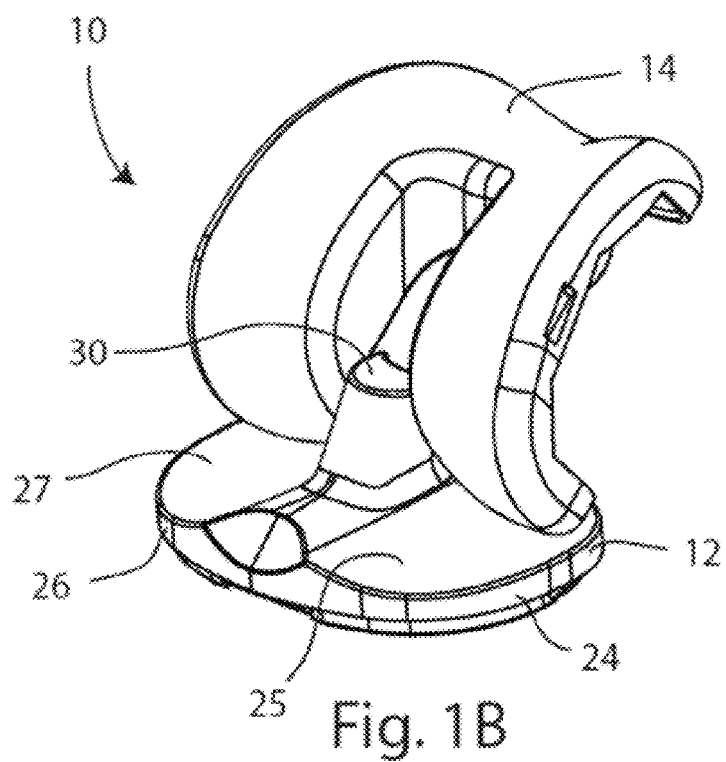
FIG. 1B is a perspective front view of the assembly of FIG. 1A in flexion.
Figure 2:
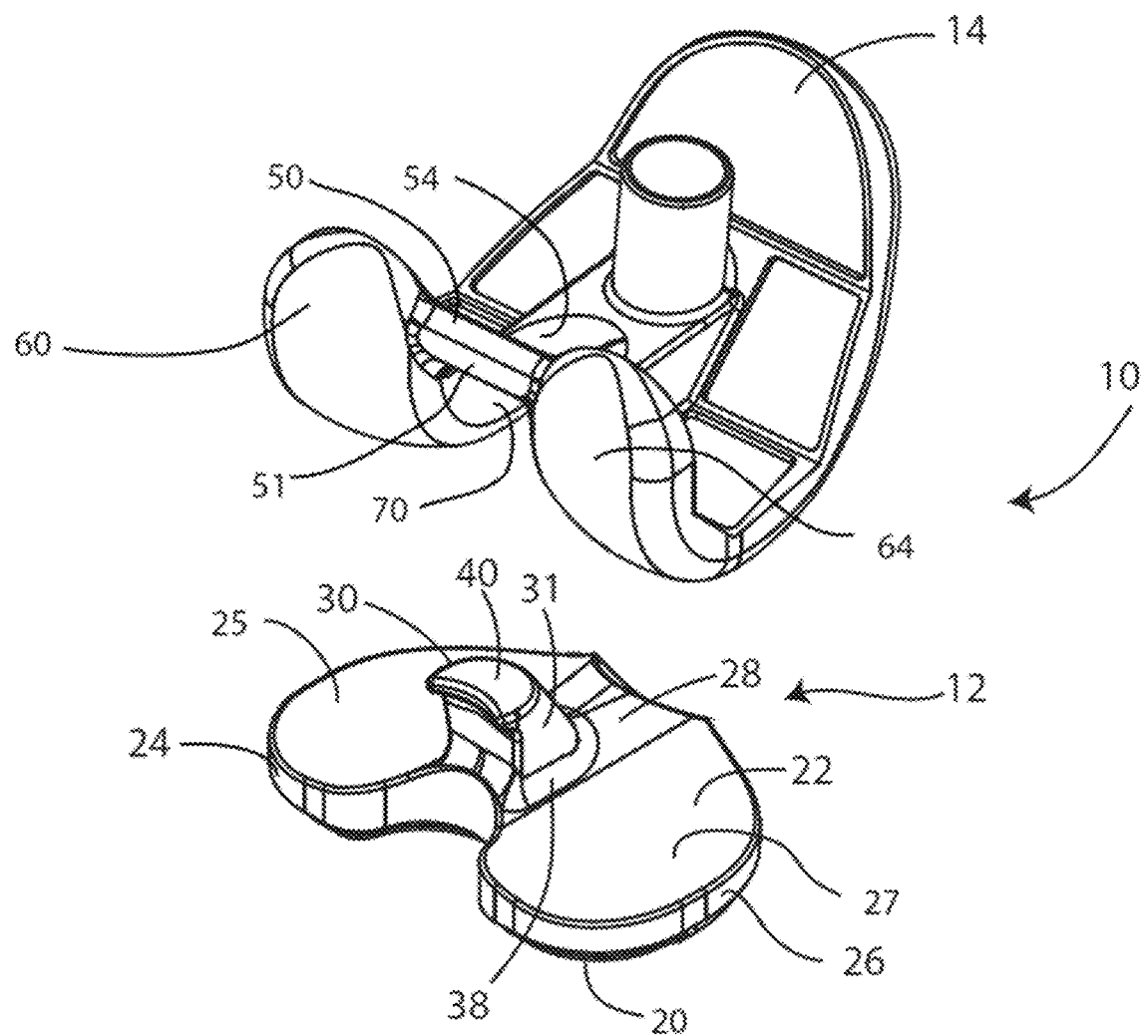
FIG. 2 is an exploded view of the assembly of FIG. 1A.

Referring to FIGS. 1A-2, an assembly 10 for an implantable knee prosthesis is shown including a femoral component 14 and a tibial insert 12. The femoral component 14 and tibial insert 12 are shown coupled in extension in FIG. 1A, coupled in flexion in FIG. 1B, and shown in an exploded view in FIG. 2. The tibial insert 12 may be further coupled to a tibial baseplate component (not shown) which may be implanted in a prepared tibia of a patient (also not shown). The femoral component 14 and tibial insert 12 illustrated in FIGS. 1A-2 are right femoral and tibial insert components. Left femoral and tibial insert components (not shown) would be mirror images of the right femoral and tibial insert components shown in FIGS. 1A-2. The femoral component 14 may also be referred to as a posterior stabilizing femoral component 14 (or "PS femoral component") and the tibial insert 12 may also be referred to as a posterior stabilizing tibial insert (or "PS insert").

FIGS. 3A-3D show the PS insert 12 of FIGS. 1A-2 in isolation. The PS insert 12 may include a fixation side 20, which may be an inferior side, opposite an articulation side 22, which may be a superior side. The articulation side 22 may include a medial articulation portion 24 having a medial condylar articulation surface 25 and a lateral articulation portion 26 having a lateral condylar articulation surface 27. A central portion 28 may separate the medial articulation portion 24 from the lateral articulation portion 26. A post 30 may protrude superiorly from the central portion 28 and extend from a post base 38 to a post top or post superior end 40. From the anterior perspective (shown in FIG. 3B) and/or the posterior perspective (shown in FIG. 3A), the post 30 may have its maximum medial-lateral or horizontal width toward the post superior end 40 of the post 30, and its minimum medial-lateral or horizontal width toward the post base 38 of the post 30. The post 30 may also be bilaterally symmetrical from the anterior and/or posterior perspectives. A recess 45 may be formed posterior to the central portion 28, between the medial and lateral articulation portions 24, 26, and may provide room for a posterior cruciate ligament (not shown). The PS insert 12 may further include an insert base 46, which may further include an engagement feature 48 for engagement with a tibial baseplate component.

Figure 3A:
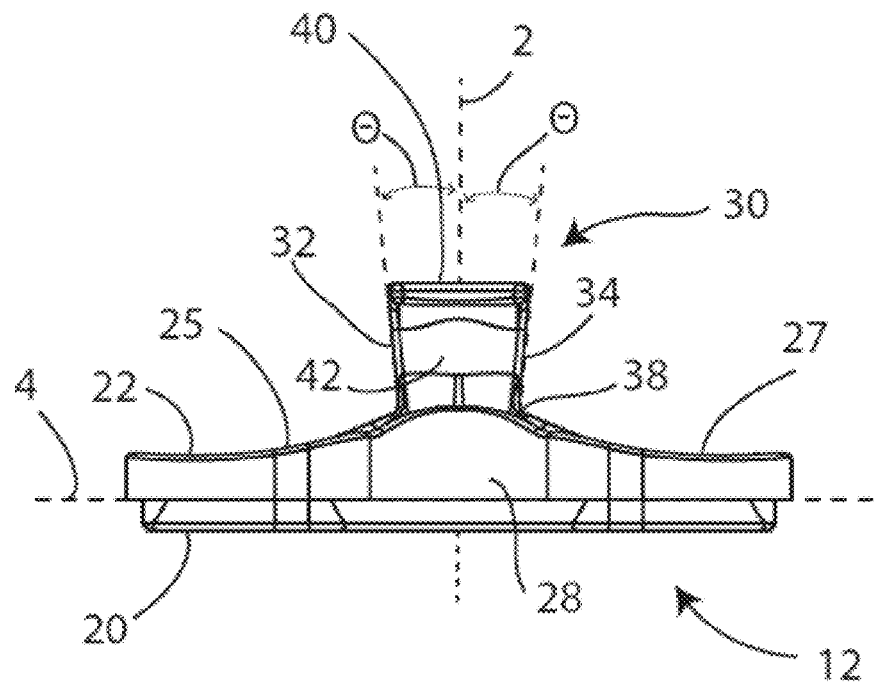
FIG. 3A is a posterior view of the tibial insert of FIG. 1A.
Figure 3B:
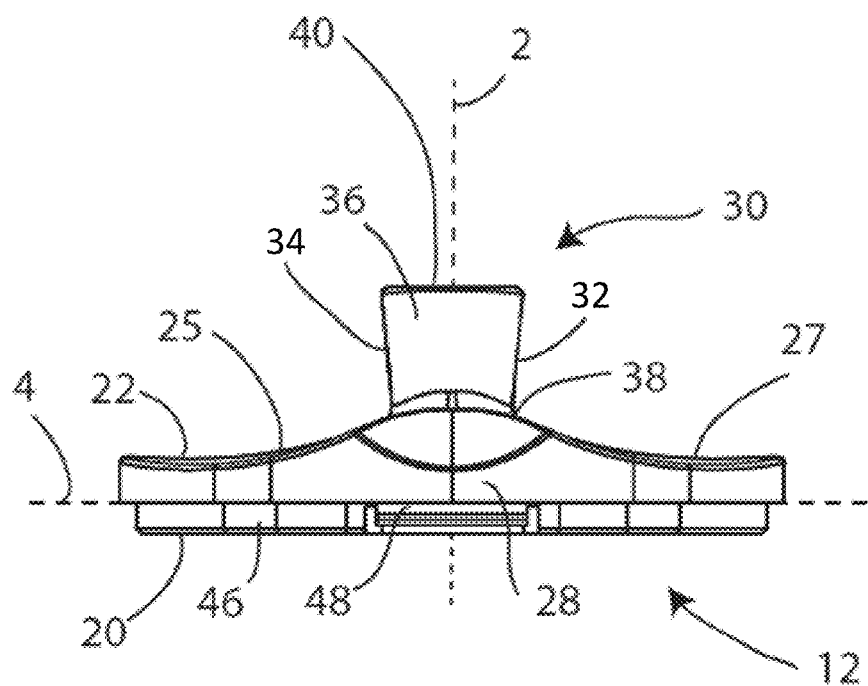
FIG. 3B is an anterior view of the tibial insert of FIG. 1A.
Figure 3C:
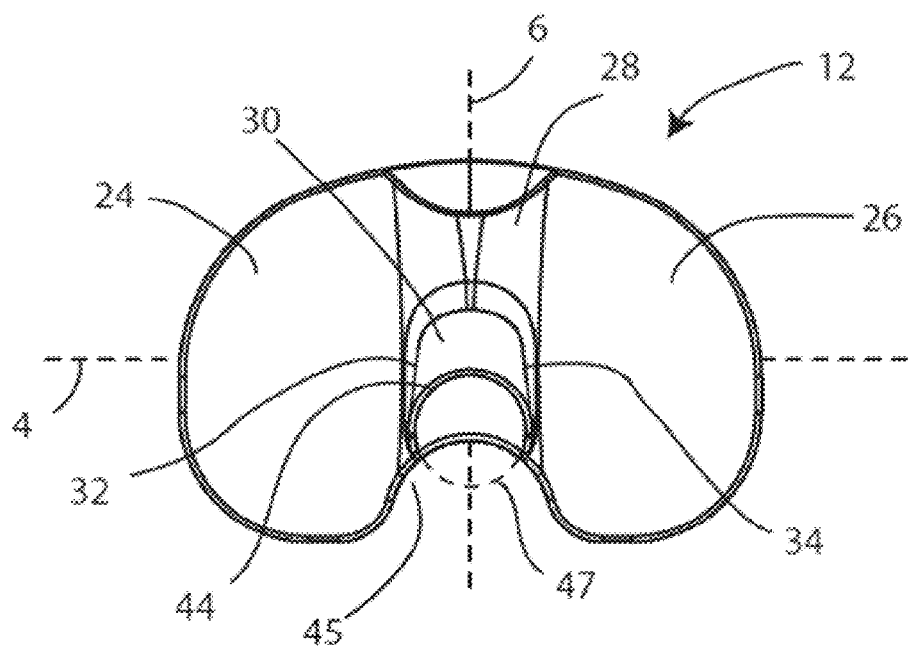
FIG. 3C is a superior view of the tibial insert of FIG. 1A.
Figure 3D:
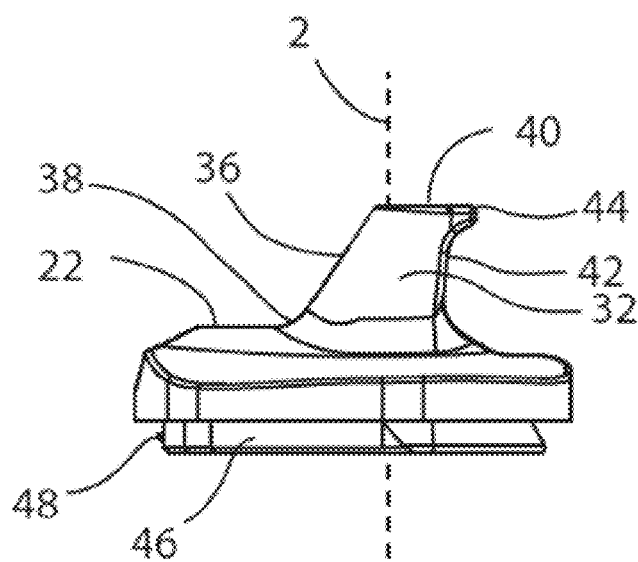
FIG. 3D is a medial side view of the tibial insert of FIG. 1A.
Figure 4:
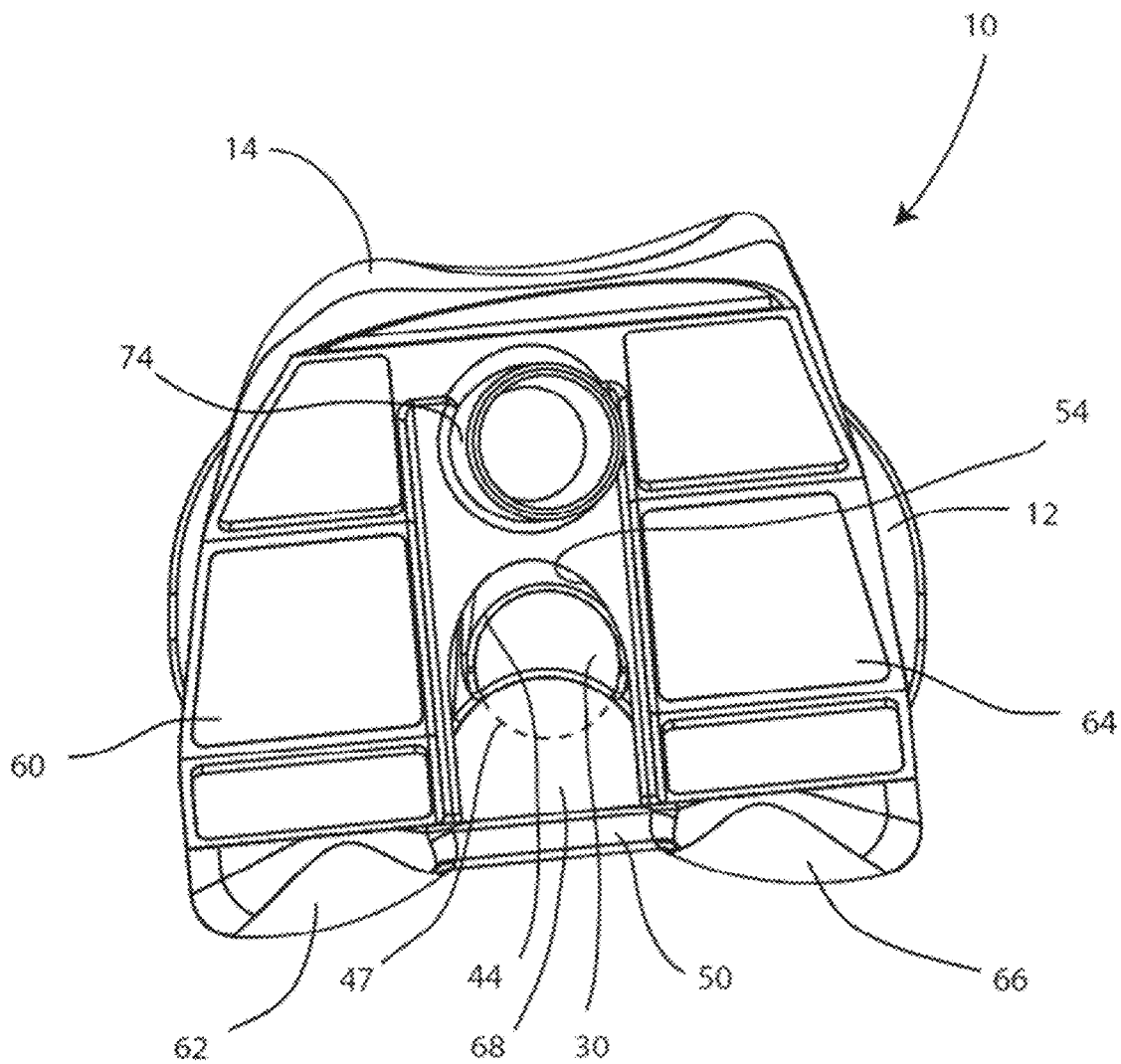
FIG. 4 is a top down view of the assembly of FIG. 1A.
Figure 5:
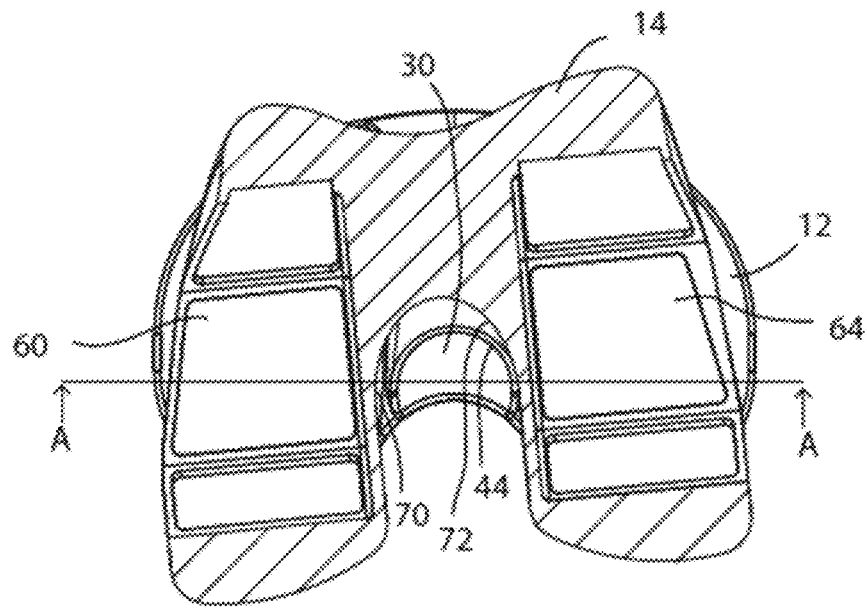
FIG. 5 is a top down cross-sectional view of the assembly of FIG. 1A, taken along line B-B in FIG. 6.
Figure 6:
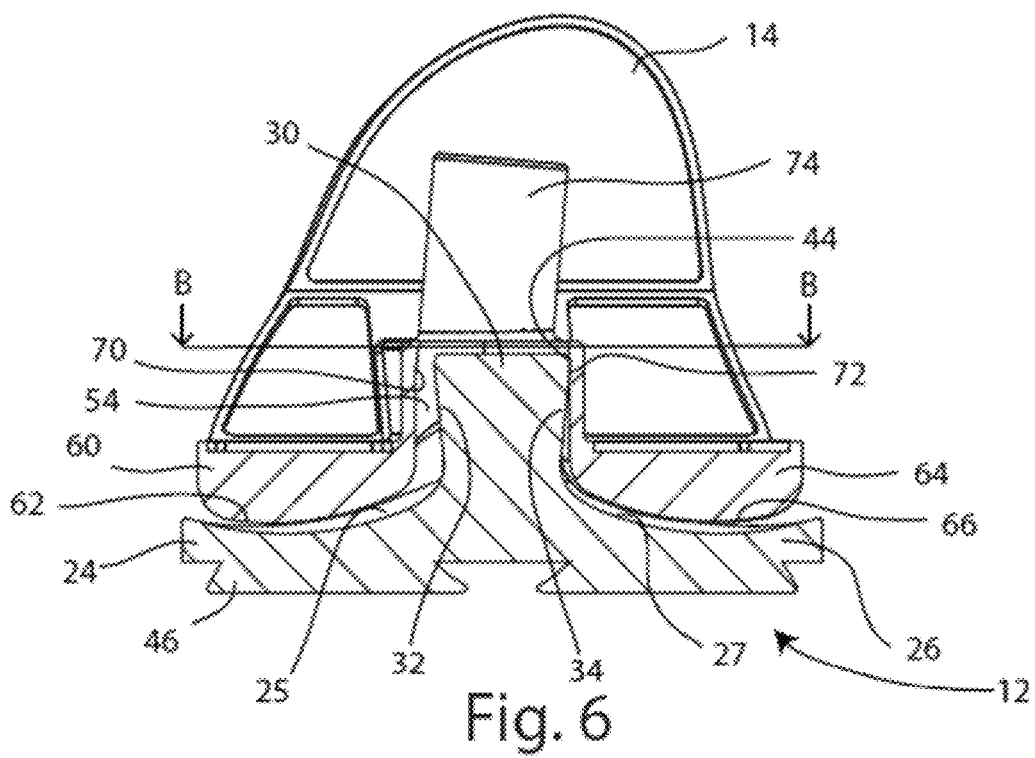
FIG. 6 is a posterior cross-sectional view of the assembly of FIG. 1A, taken along line A-A in FIG. 5.
Figure 7:
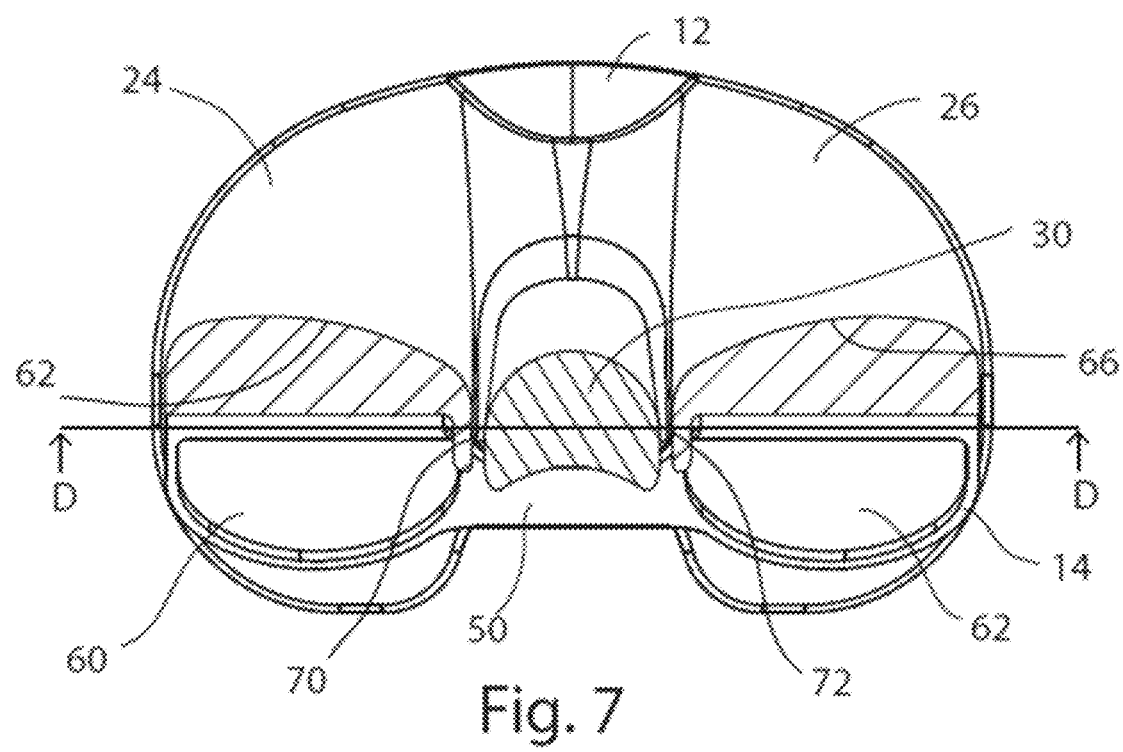
FIG. 7 is a top down cross-sectional view of the assembly of FIG. 1B, taken along line C-C in FIG. 8.
Figure 8:
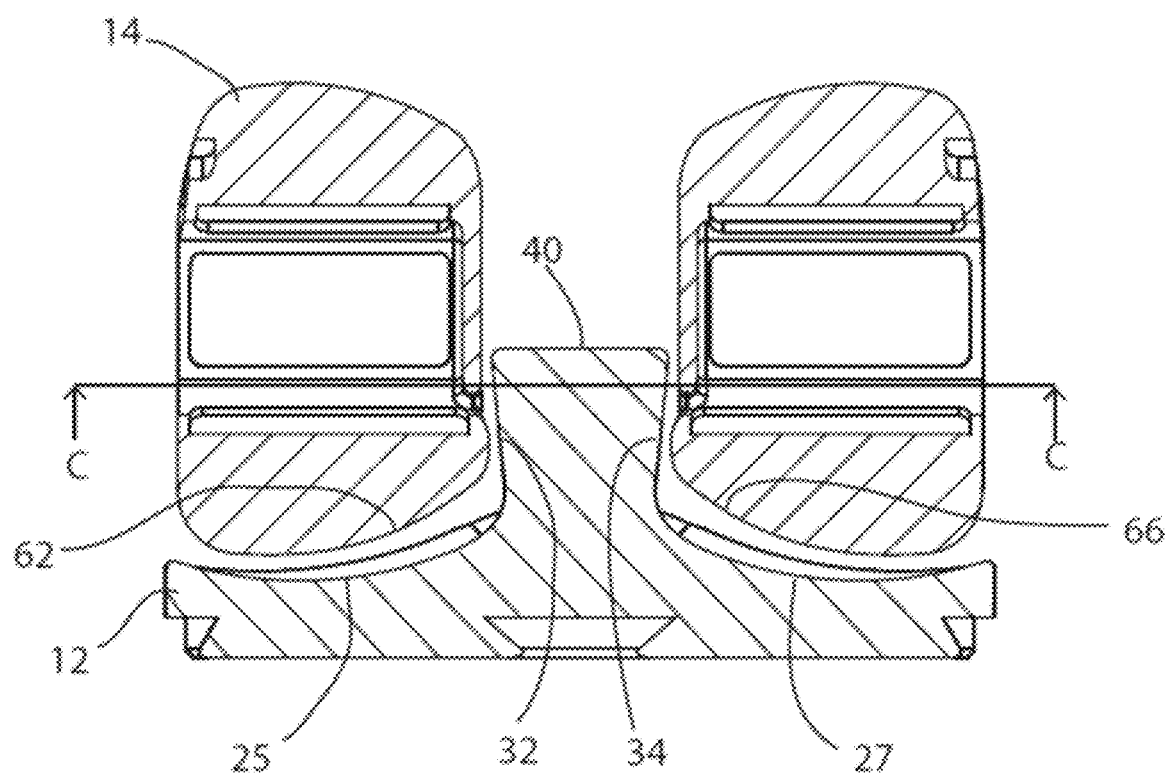
FIG. 8 is a posterior cross-sectional view of the assembly of FIG. 1B, taken along line D-D in FIG. 7.

Continuing with FIGS. 1A-3D, the post 30 may have an articulation surface 31 extending around the post 30 on the medial, posterior, lateral, and anterior aspects of the post 30. The articulation surface 31 may include a medial articulation surface 32, a lateral articulation surface 34, an anterior post surface 36, and a posterior articulation surface 42. The medial and lateral articulation surfaces 32, 34 may be non-parallel to one another and taper inward from the post superior end 40 to the post base 38 relative to an insert midline vertical axis 2, as shown in FIGS. 3A and 3B. As shown in FIG. 3A, an angle θ between the vertical axis 2 and each tapered surface 32, 34 may be about 6.5°, in at least one embodiment. Since the post 30 may be bilaterally symmetrical, the angle θ may be the same on both the medial and lateral articulation surfaces 32, 34 of the post 30. In other embodiments of the disclosure, angle θ may range from about 6° to 11° degrees. The medial articulation surface 32 may be continuous with the medial condylar articulation surface 25, and the lateral articulation surface 34 may be continuous with the lateral condylar articulation surface 27, as can been further seen in cross-section in FIGS. 6 and 8. The anterior post surface 36 may extend between the medial and lateral articulation surfaces 32, 34 and may be convexly rounded. The anterior post surface 36 may also taper outward from the post superior end 40 to the post base 38 relative to the midline vertical axis 2, as best seen in FIG. 3D. In other embodiments of the PS insert 12, the anterior post surface 36 may include less or no taper.

Referring to FIG. 3C, the boundary of the post superior end 40 defines a rounded rim 44 shaped as a portion of a circle defined by a circular envelope 47, as seen from a superior perspective. The post superior end 40 and rim 44 may be crescent-shaped with a concave recess toward a posterior end of the post 30 as shown, and may permit passage of the posterior cruciate ligament. The post superior end 40 may be circular; the rim 44 may provide increased rotational range of motion and surface contact against the femoral component 14 in comparison to traditional posts with a more square or rectangular shape and no rim. Thus, the rounded post superior end 40 and rim 44 may allow for surface contact with the femoral component 14 in contrast to the mere point or edge contact that is achieved by traditional posts that do not have these features.

The PS femoral component 14 depicted in FIGS. 1-8 may include a cam element or cam bar 50 and a box structure 52 for providing posterior stabilization in place of absent ligaments. The cam bar 50 may include a cam articulating surface 51 which may contact the posterior articulation surface 42 of the post 30 during flexion, as in FIGS. 1B and 7. An internal articulation surface 54 may reside on the inside of the box structure 52 and may contact the post 30 during articulation and rotation of the knee joint. The internal articulating surface 54 may be concavely curved, and may contact the rim 44 of the post 30 during axial rotation of the knee joint about the post. The PS femoral component 14 may further include a medial condyle 60 having a medial condylar articulation surface 62, and a lateral condyle 64 having a lateral condylar articulation surface 66. The medial and lateral condylar articulation surfaces 62, 66 may articulate against the PS insert 12 medial and lateral condylar articulation surfaces 25, 27 respectively. A gap 68 may be formed between the medial and lateral condyles 60, 64, with the cam bar 50 extending medial-laterally across the gap 68. The internal articulation surface 54 may include a medial portion 70 continuous with a lateral portion 72. In the embodiment depicted, a fixation post 74 may protrude superiorly from the PS femoral component 14. However, in other embodiments of the PS femoral component 14, the fixation post 74 may be absent and/or other fixation features such as posts, spikes, pegs, webs, keels or teeth may be present to affix the PS femoral component 14 to a prepared femur (not shown).

Figure 9:
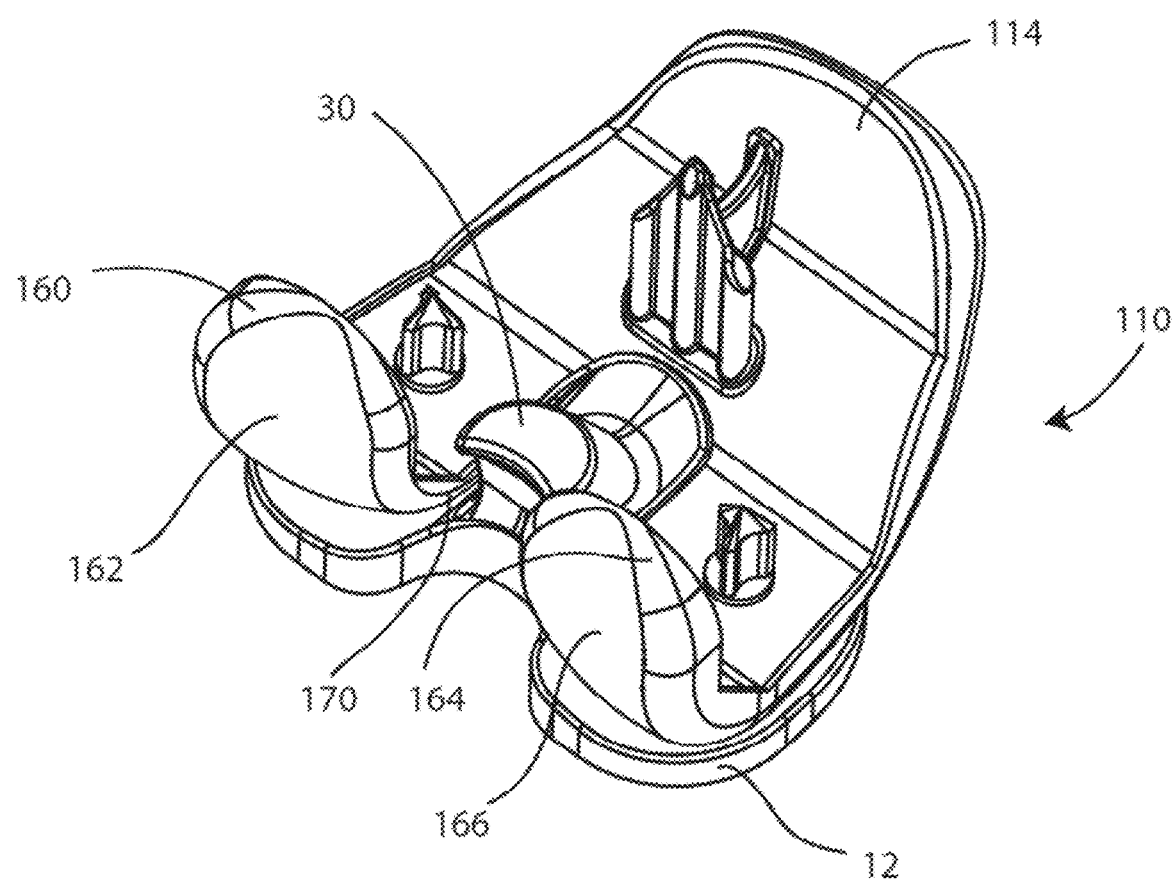
FIG. 9 is a perspective rear view of an assembly of the disclosure, including a cruciate retaining femoral component and the tibial insert of FIG. 1A coupled in extension.
Figure 10:
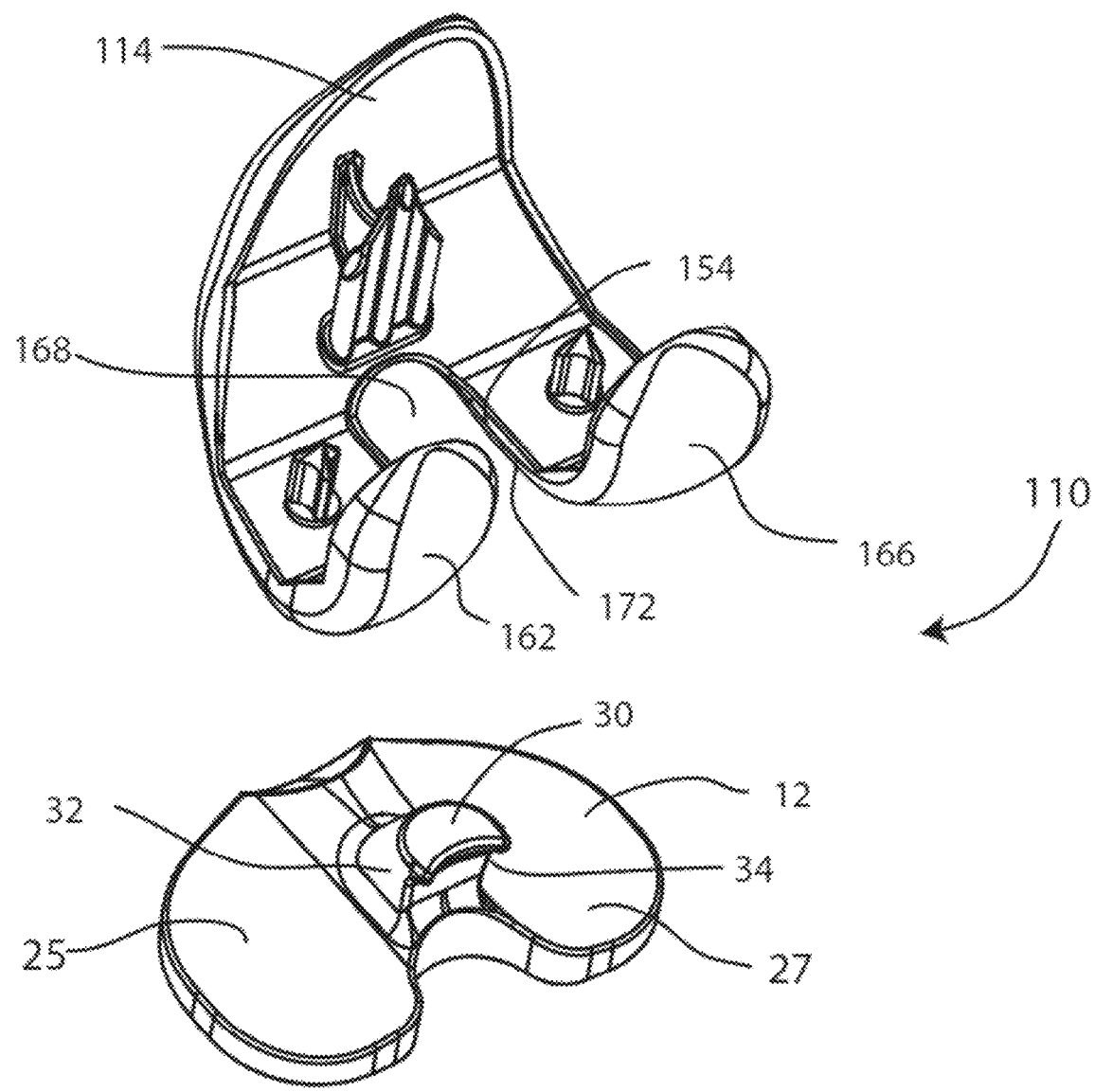
FIG. 10 is an exploded perspective rear view of the assembly of FIG. 9.
Figure 11A:
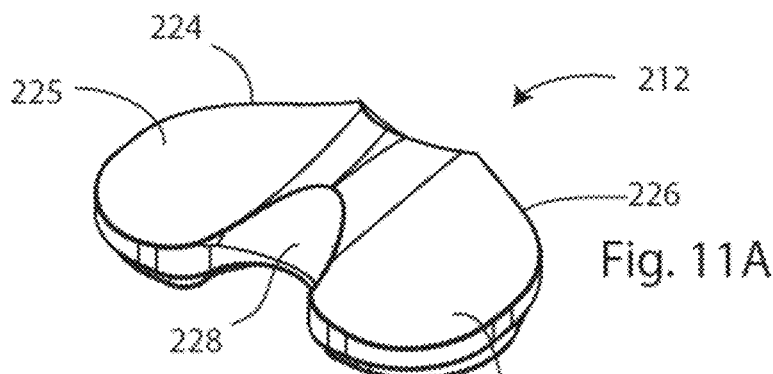
FIG. 11A is a perspective rear view of another tibial insert of the disclosure.
Figure 11B:
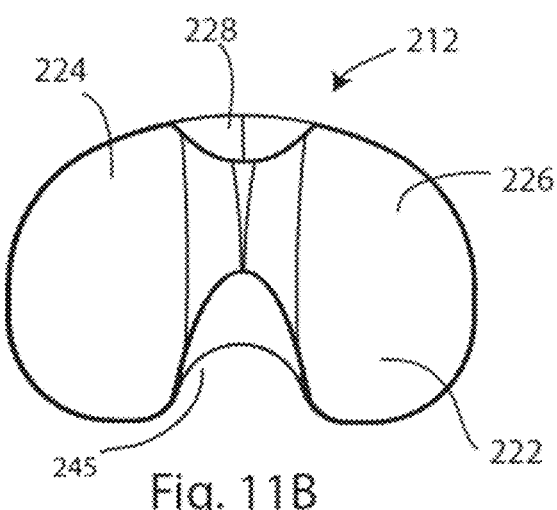
FIG. 11B is a top view of the tibial insert of FIG. 11A.
Figure 11C:
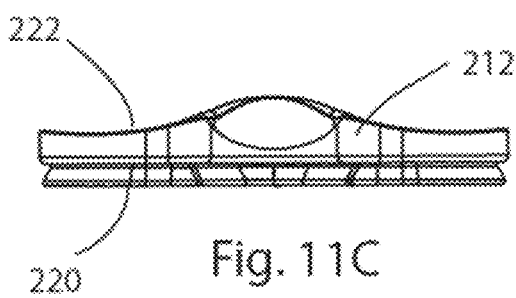
FIG. 11C is a posterior view of the tibial insert of FIG. 11A.
Figure 11D:
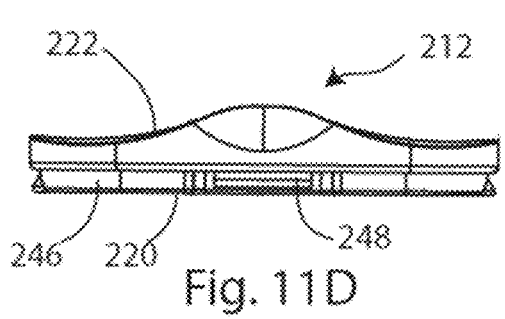
FIG. 11D is an anterior view of the tibial insert of FIG. 11A.
Figure 11E:
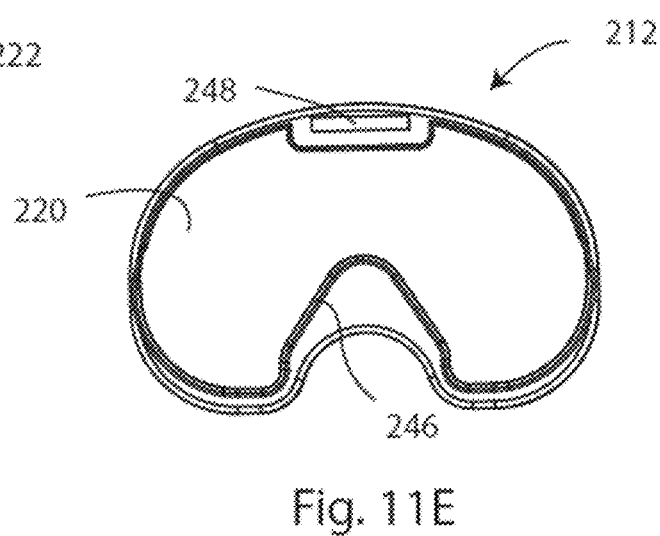
FIG. 11E is a bottom view of the tibial insert of FIG. 11A.

Referring to FIGS. 9 and 10, another assembly 110 embodiment of the disclosure may include the PS insert 12 of FIGS. 1-8 coupled with a cruciate retaining femoral component 114 (or "CR femoral component"). The CR femoral component 114 may include medial and lateral condyles 160, 164, with a gap 168 formed between the medial and lateral condyles 160, 164. As a CR femoral component 114, no cam bar or box may be present. The medial and lateral condyles 160, 164 may include medial and lateral condylar articulation surfaces 162, 166, and an internal articulation surface 154 with medial and lateral articulating surfaces 170, 172.

The medial and lateral articulation surfaces 32, 34 of the post 30 may be tapered and may permit natural articulation of the CR femoral component 114 with the PS insert 12, which may not be achievable if the post 30 were not tapered. For example, if the post 30 had straight sides instead of tapered sides, the wider width of the post 30 at the base of the post 30 would interfere with the internal articulating surfaces 170, 172 of the medial and lateral condyles 160, 164. When the PS femoral component 14 is coupled with the PS insert 12 to form assembly 10, as in FIG. 1A and FIG. 4, the circular shape of the post superior end 40 in combination with the tapered medial and lateral articulation surfaces 32, 34 of the post 30, may permit the PS femoral component 14 to articulate relative to the PS insert 12 in the manner of a posterior stabilized femoral component. However, when the PS insert 12 is paired and implanted with the CR femoral component 114, the resultant assembly 110 may provide the native articulation and rotation of a cruciate retaining implant.

Referring to FIGS. 11A-11E, an alternative embodiment of a tibial insert 212 is shown. Tibial insert 212 may be referred to as a cruciate retaining tibial insert 212 (or "CR insert"). In a system of the disclosure, CR insert 212 may be implanted with the CR femoral component 114 and a tibial baseplate component (not shown) to form a cruciate retaining knee prosthesis system. The CR insert 212 may include a fixation side 220, which may be an inferior side, opposite an articulation side 222, which may be a superior side. The articulation side 222 may include a medial articulation portion 224 having a medial condylar articulation surface 225 and a lateral articulation portion 226 having a lateral condylar articulation surface 227. A central portion 228 may separate the medial articulation portion 224 from the lateral articulation portion 226. A recess 245 may be formed posterior to the central portion 228, between the medial and lateral articulation portions 224, 226, and may provide room for a posterior cruciate ligament. The CR insert 212 may further include an insert base 246 and an engagement feature 248 for engagement with a tibial baseplate component. The CR insert 212 may be coupled with the CR femoral component 114 to form a cruciate retaining assembly. This assembly may be implanted with a suitable tibial baseplate as a cruciate retaining knee prosthesis. The CR insert 212 may also be coupled with the PS femoral component 14 and implanted with a suitable tibial baseplate.

Figure 12A:
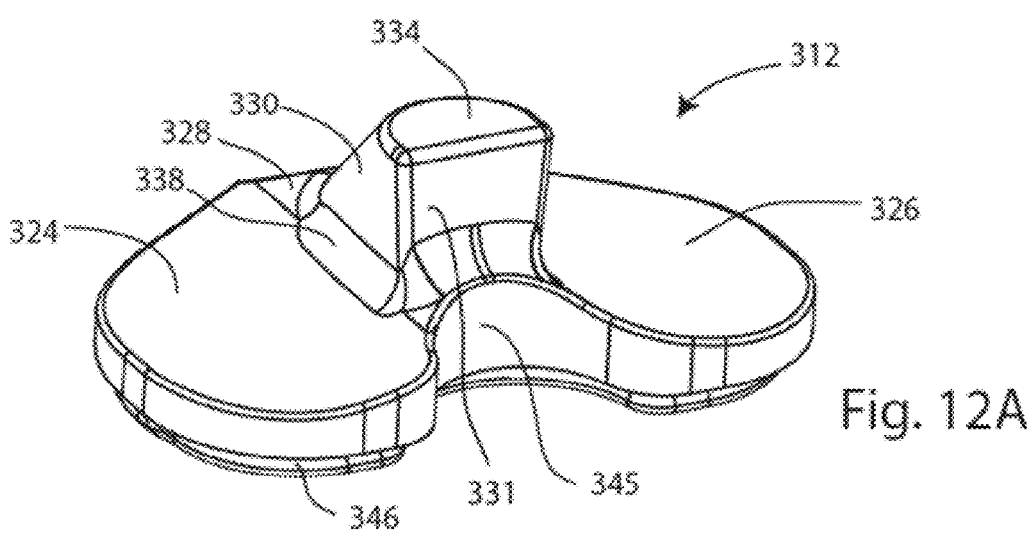
FIG. 12A is a perspective rear view of another tibial insert of the disclosure.
Figure 12B:
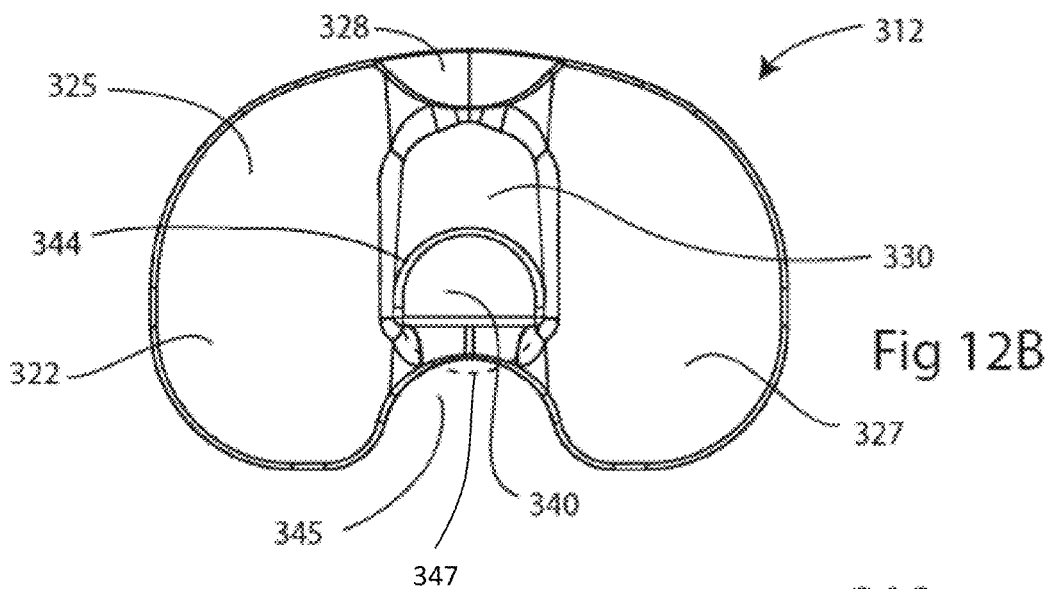
FIG. 12B is a top view of the tibial insert of FIG. 12A.
Figure 12C:
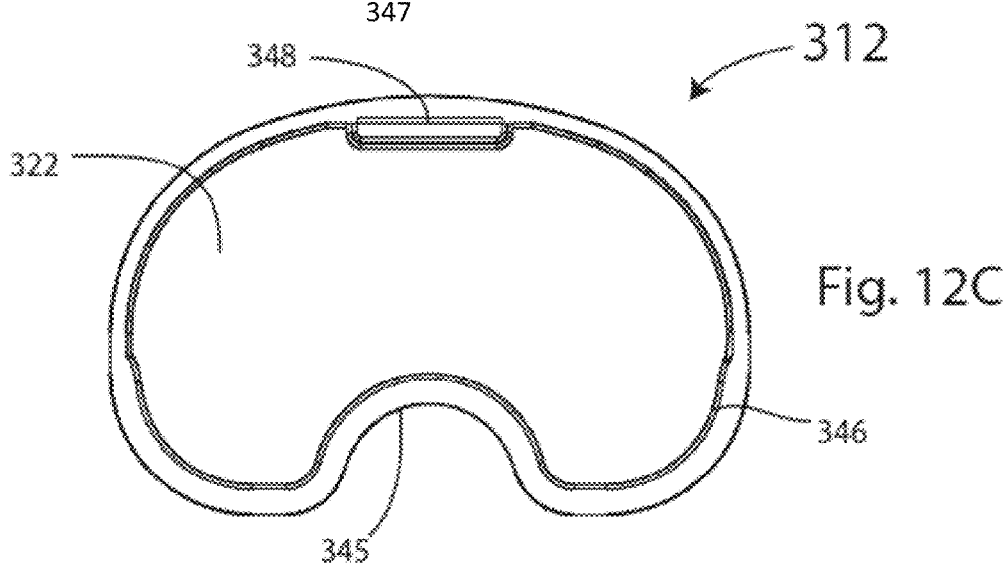
FIG. 12C is a bottom view of the tibial insert of FIG. 12A.
Figure 12D:
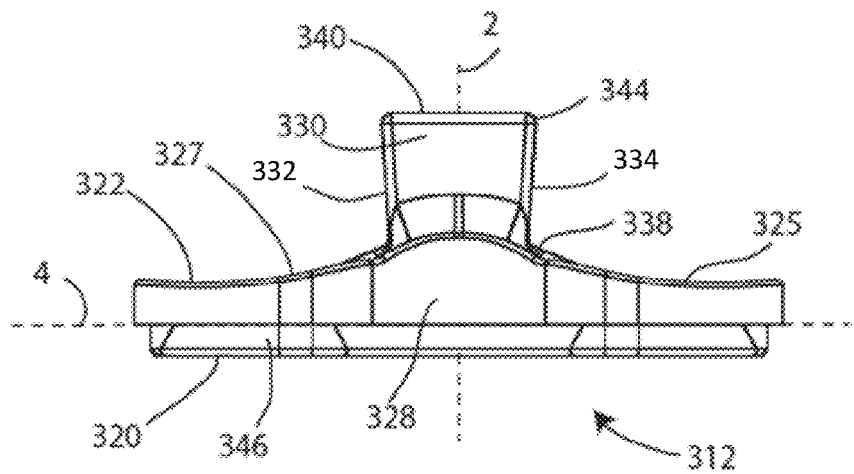
FIG. 12D is a posterior view of the tibial insert of FIG. 12A.
Figure 12E:
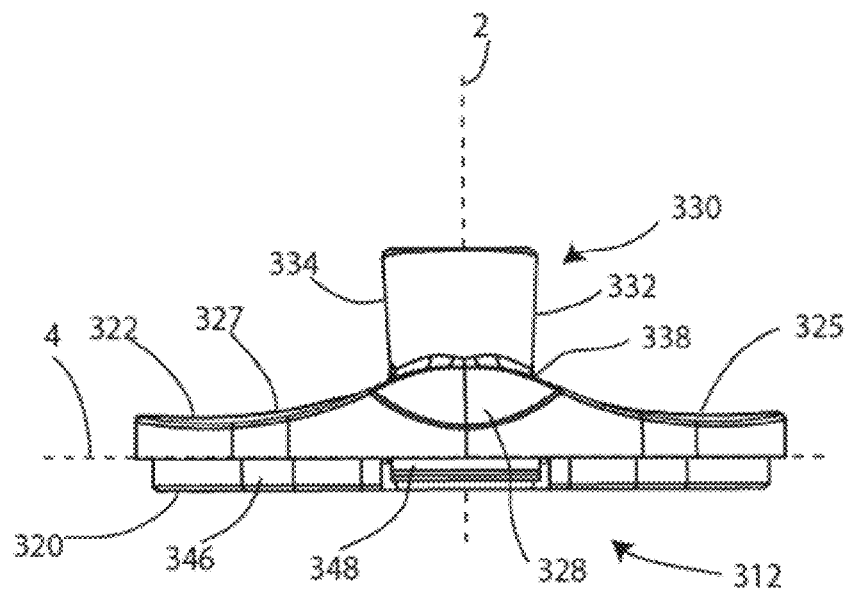
FIG. 12E is an anterior view of the tibial insert of FIG. 12A.

Referring to FIGS. 12A-12F, another alternative embodiment of a tibial insert 312 is shown. The tibial insert 312 may be referred to as a constrained condylar knee (CCK) tibial insert 312 (or "CCK insert"). The CCK insert 312 may include a fixation side 320, which may be an inferior side, opposite an articulation side 322, which may be a superior side. The articulation side 322 may include a medial articulation portion 324 having a medial condylar articulation surface 325 and a lateral articulation portion 326 having a lateral condylar articulation surface 327. A central portion 328 may separate the medial articulation portion 324 from the lateral articulation portion 326. A post 330 may protrude superiorly from the central portion 328, and extend from a post base 338 to a top, or post superior end 340. From the anterior perspective, as shown in FIG. 12E, and the posterior perspective, as shown in FIG. 12D, the post 330 may have its maximum medial-lateral or horizontal width at the superior end 340 of the post 330, and its minimum medial-lateral or horizontal width at the post base 338 of the post 330. The post 330 may be bilaterally symmetrical from the anterior and posterior perspectives. The CCK insert 312 may further include an insert base 346 and an engagement feature 348 for engagement with a tibial tray (not shown).

Figure 12F:
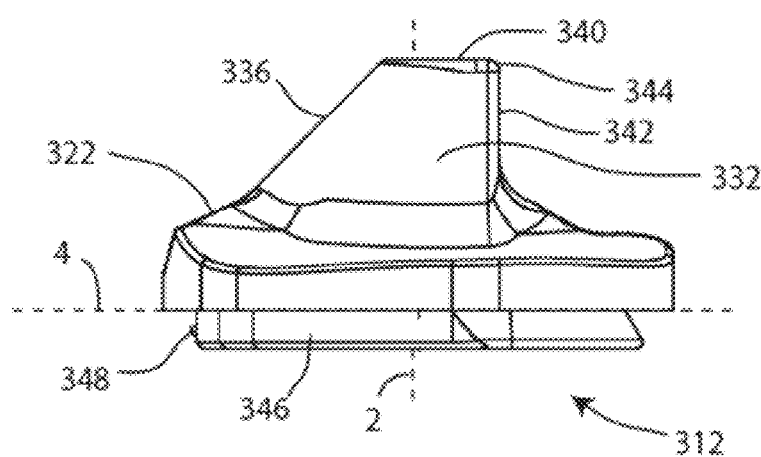
FIG. 12F is a medial side view of the tibial insert of FIG. 12A.

The post 330 may have an articulation surface 331 extending around the post 330 on the medial, posterior, lateral, and anterior aspects of the post 330. The articulation surface 331 may include a medial articulation surface 332, a lateral articulation surface 334, an anterior post surface 336, and a posterior articulation surface 342. The medial and lateral articulation surfaces 332, 334 may taper slightly inward from the post superior end 340 to the post base 338 of the post 330 relative to an insert midline vertical axis 2. However, some embodiments of CCK insert 312 may include no taper of the medial and lateral articulation surfaces 332, 334. The medial articulation surface 332 may be continuous with the medial condylar articulation surface 325, and the lateral articulation surface 334 may be continuous with the lateral condylar articulation surface 327. The anterior post surface 336 may extend between the medial and lateral surfaces 332, 334 and may be convexly rounded. The anterior post surface 336 may taper outward from the post superior end 340 to the post base 338 relative to the midline axis 2, as best seen in FIG. 12F. In other embodiments of the CCK insert 312, the anterior post surface 336 may include less taper, more taper, and/or no taper. The post 330 of the CCK insert 312 may be wider and bigger in diameter than the post 30 of PS insert 12, for example to provide increased stability in the case of removal of the collateral ligaments.

Referring to FIG. 12B, the boundary of the post superior end 340 may define a rounded rim 344 shaped as a portion of a circle, from a superior perspective. The post superior end 340 and rim 344 may be semi-circular as shown, however the rim 344 may define a circular envelope 347. The post superior end 340 may be circular and rim 344 may provide increased surface contact and rotational range of motion when coupled and implanted with the PS femoral component 14 in comparison to traditionally shaped posts with a more square or rectangular shaped post. Thus, the rounded post superior end 340 and rim 344 may allow for surface contact with the femoral component 14 in contrast to the mere point or edge contact that is achieved by traditional posts that do not have these features. The CCK insert 312 may be coupled with the PS femoral component 14 to form a constrained condylar knee assembly, and this assembly may be implanted with a suitable tibial baseplate as a constrained condylar knee prosthesis. The CCK insert 312 may also be coupled with the CR femoral component 114 and implanted with a suitable tibial baseplate. Thus, all of the tibial inserts 12, 212, and 312 disclosed herein are interchangeable with both the CR femoral component 114 and the PS femoral component 14. FIG. 13 is a chart showing the potential combinations of components.

The tibial inserts 12, 212, 312, PS femoral component 14 and CR femoral component 114 may be grouped together as a modular knee replacement system and provided as a kit in one or more packages, in one non-limiting example. Another kit may include a CR femoral component 114, a PS insert 12 and a CR insert 212, in one or more packages in another non-limiting example. Yet another kit may include a PS femoral component 14, a PS insert 12, a CR insert 212, and a CCK insert 312, in one or more packages in yet another non-limiting example. However, it will also be understood that other kit embodiments may utilize any of the tibial inserts and/or femoral components described herein in any number or combination, in one or more packages. Furthermore, other components may also be including in any kit described herein, such as suitable tibial baseplate components, patellar components, etc., in one or more packages. It will also be understood that any of the tibial inserts disclosed herein may be formed of vitamin E polyethylene, highly cross linked polyethylene, ultra-high molecular weight polyethylene (UHMWPE), or any other suitable material.

In a method of the disclosure, a patient may initially experience compromise of the anterior cruciate ligament. The ACL may be removed, and a CR type prosthesis may be implanted, including a CR femoral component 114, a CR insert 212, and a tibial baseplate component. Later, the same patient may experience compromise of the PCL and may need additional stabilization of the knee joint. The PCL may be removed, the CR tibial insert 212 may be removed, and a PS tibial insert 12 of the disclosure may be inserted between the originally implanted CR femoral component 114 and the tibial baseplate component, thus providing additional stability for the missing PCL. Even later, the same patient may experience instability of the collateral ligaments. The PS tibial insert 12 may be removed, and the CCK tibial insert 312 of the disclosure may be inserted between the originally implanted CR femoral component 114 and the tibial baseplate component. Thus, the patient may progress from a CR knee prosthesis, to a PS knee prosthesis, and finally to a CCK knee prosthesis without requiring replacement of the originally implanted femoral and/or tibial baseplate components. The interchangeability of the inserts 12, 212, 312 permit replacement of only the tibial insert component in order to provide increasing levels of support and stability to the knee joint.

In another method of the disclosure, a patient may initially experience compromise of both the ACL and the PCL. These ligaments may be removed, and a PS type prosthesis may be implanted, including a PS femoral component 14, a PS insert 12, and a tibial baseplate component. Later, the same patient may experience instability of the collateral ligaments. The PS insert 12 may be removed, and a CCK insert 312 may be inserted between the originally implanted PS femoral component 14 and the tibial baseplate component. Thus, the patient may progress from a PS knee prosthesis to a CCK knee prosthesis without requiring replacement of the originally implanted PS femoral component 14 and tibial baseplate component.

Figure 14:
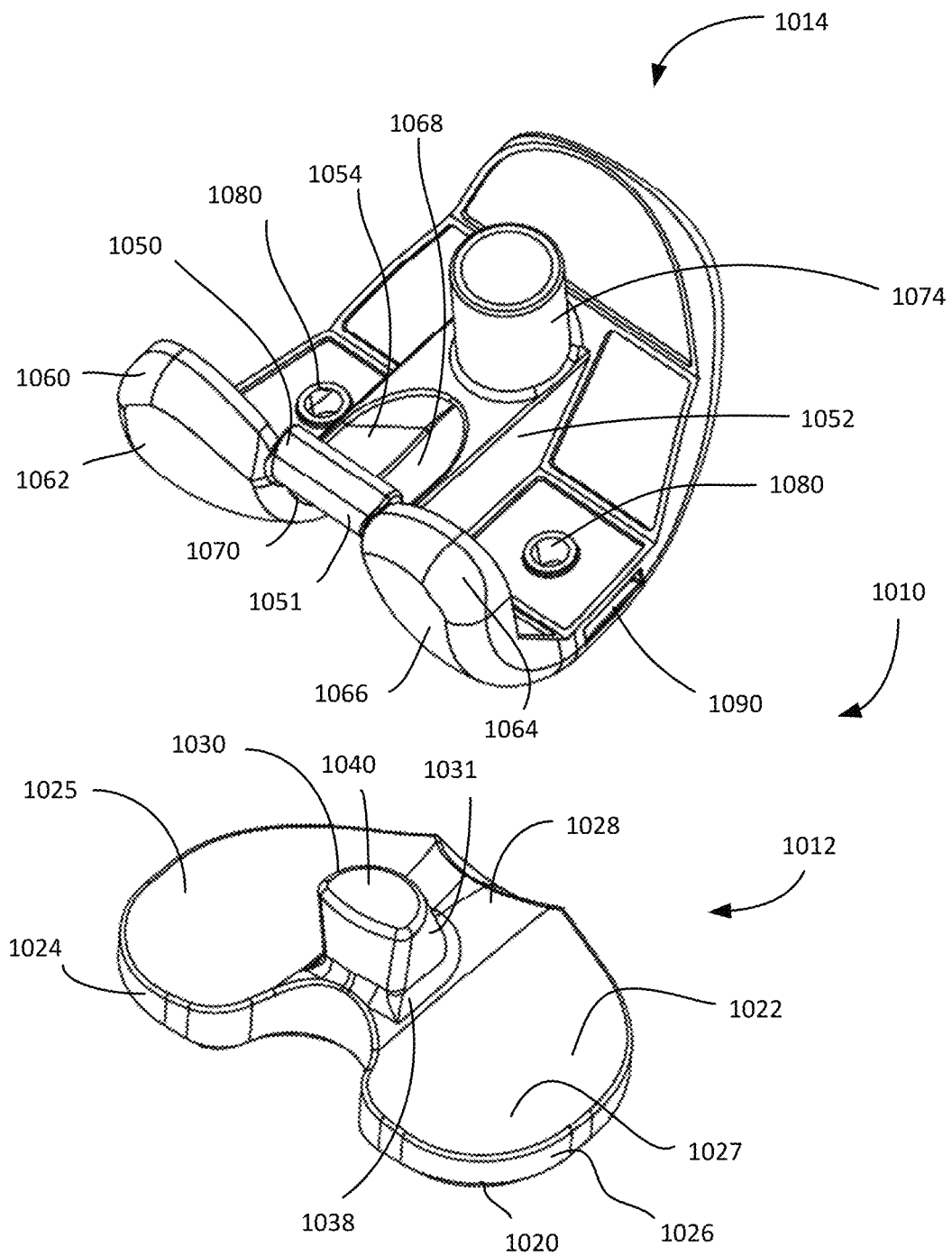
FIG. 14 is an exploded rear view of another assembly of the disclosure, including a posterior stabilizing femoral component and a posterior stabilizing tibial insert.
Figure 15:
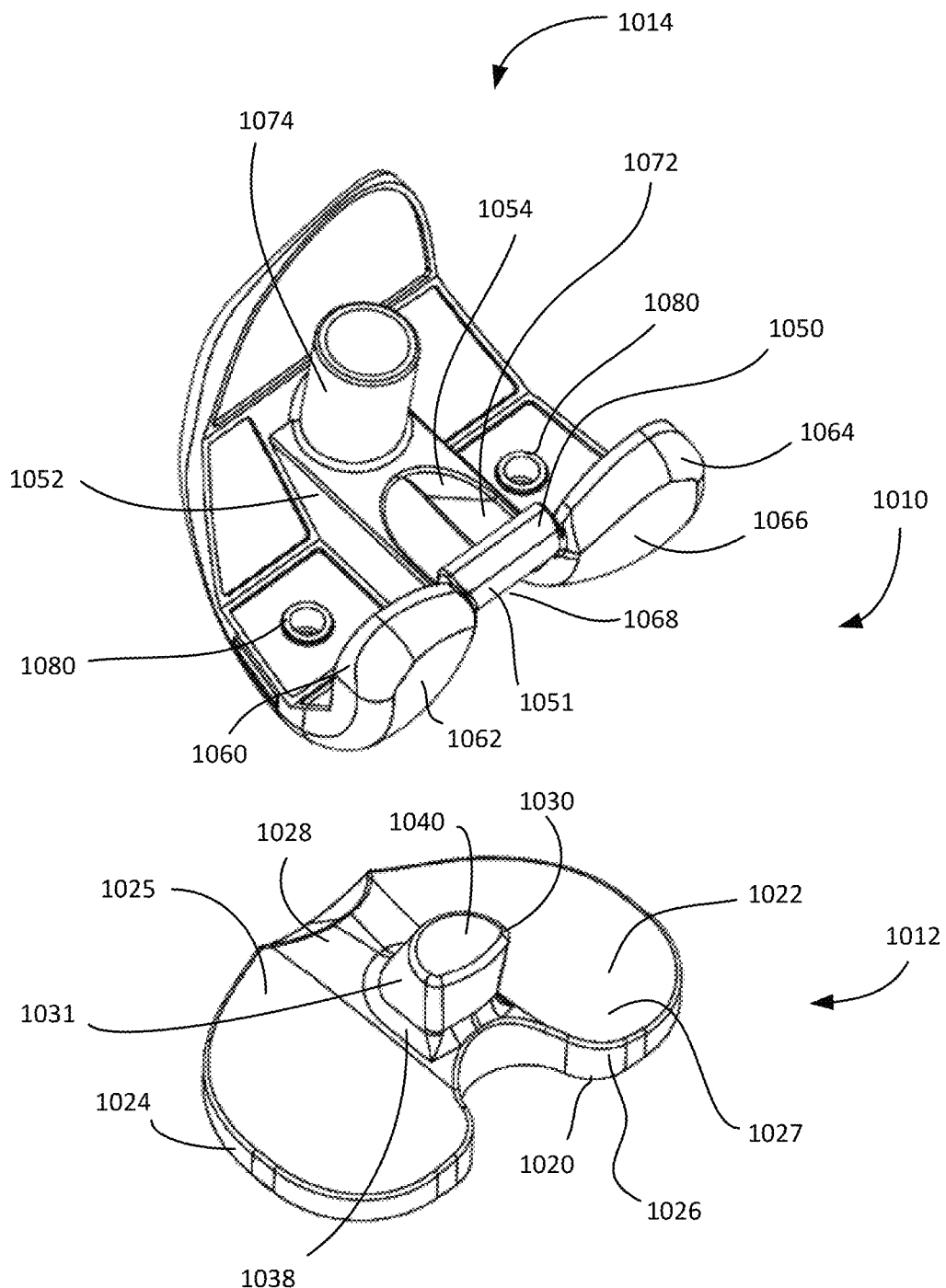
FIG. 15 is another exploded rear view of the assembly of FIG. 14.

Referring to FIGS. 14 and 15, another assembly 1010 of the disclosure for an implantable knee prosthesis is shown in various exploded rear views. The assembly 1010 may include a femoral component 1014 and a tibial insert 1012. The tibial insert 1012 may be further coupled to a tibial baseplate component (not shown) which may also be implanted in a prepared tibia of a patient (not shown). The femoral component 1014 and tibial insert 1012 illustrated in FIGS. 14 and 15 are right side femoral and tibial insert components. Left side femoral and tibial insert components (not shown) would be mirror images of the right side femoral and tibial insert components that are shown in FIGS. 14 and 15. The femoral component 1014 may also be referred to as a posterior stabilizing femoral component 1014 (or "PS femoral component") and the tibial insert 1012 may also be referred to as a posterior stabilizing tibial insert (or "PS insert").

FIGS. 16A-16D show the PS insert 1012 of FIGS. 15 and 14 in isolation. The PS insert 1012 may include a fixation side 1020, which may be an inferior side, opposite an articulation side 1022, which may be a superior side. The articulation side 1022 may include a medial articulation portion 1024 having a medial condylar articulation surface 1025 and a lateral articulation portion 1026 having a lateral condylar articulation surface 1027. A central portion 1028 may separate the medial articulation portion 1024 from the lateral articulation portion 1026. A post 1030 may protrude superiorly from the central portion 1028 and extend from a post base 1038 to a post top 1040 or post superior end. From the anterior perspective (shown in FIG. 16B) and/or the posterior perspective (shown in FIG. 16A), the post 1030 may have its maximum medial-lateral or horizontal width toward the top 1040 of the post 1030, and its minimum medial-lateral or horizontal width toward the base 1038 of the post 1030. The post 1030 may also be bilaterally symmetrical from the anterior and/or posterior perspectives. A recess 1045 may be formed posterior to the central portion 1028, between the medial and lateral articulation portions 1024, 1026, and may provide room for a posterior cruciate ligament (not shown). The PS insert 1012 may further include an insert base 1046, which may further include an engagement feature 1048 for engagement with a tibial baseplate component.

Figure 16A:
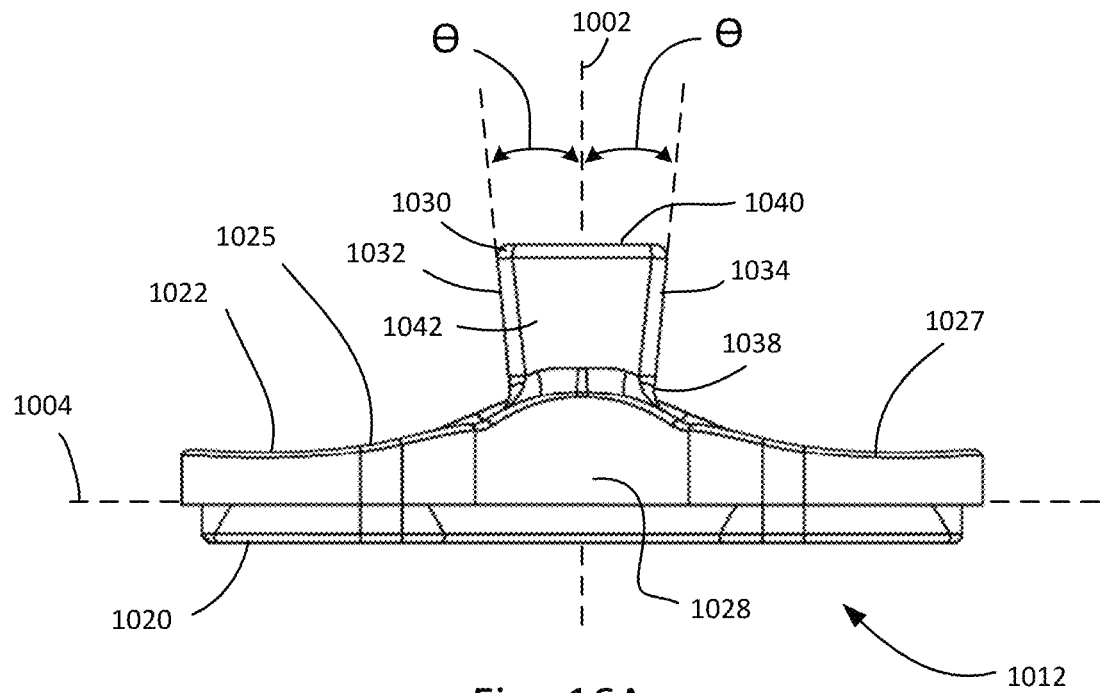
FIG. 16A is a posterior view of the tibial insert of FIG. 14.
Figure 16B:
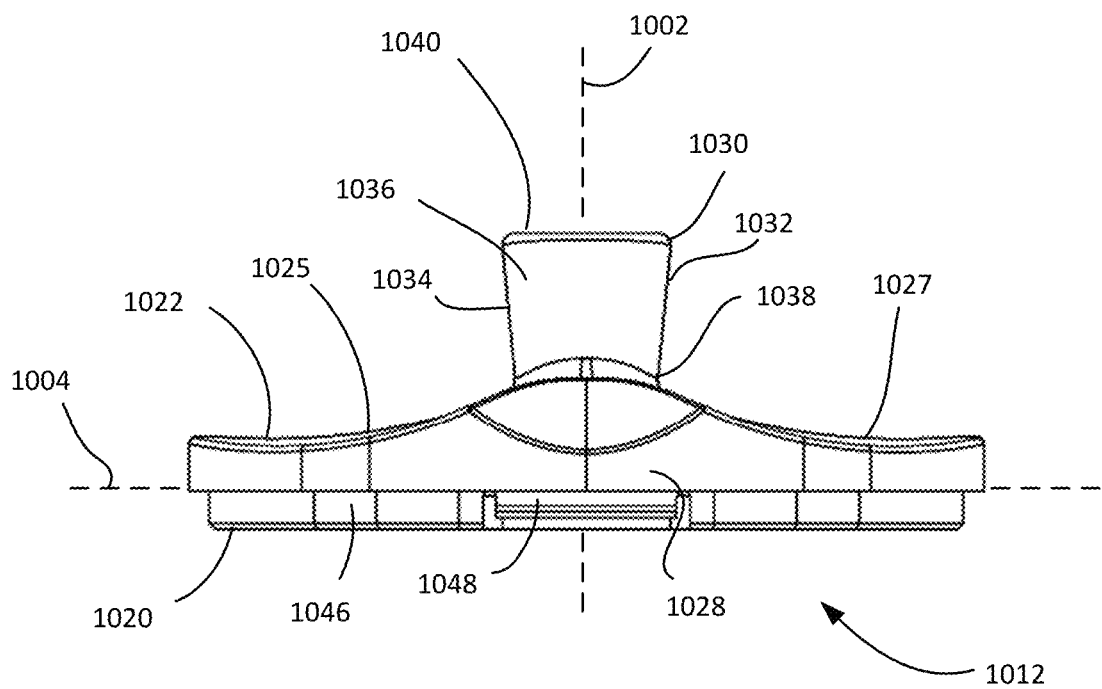
FIG. 16B is an anterior view of the tibial insert of FIG. 14.
Figure 16C:
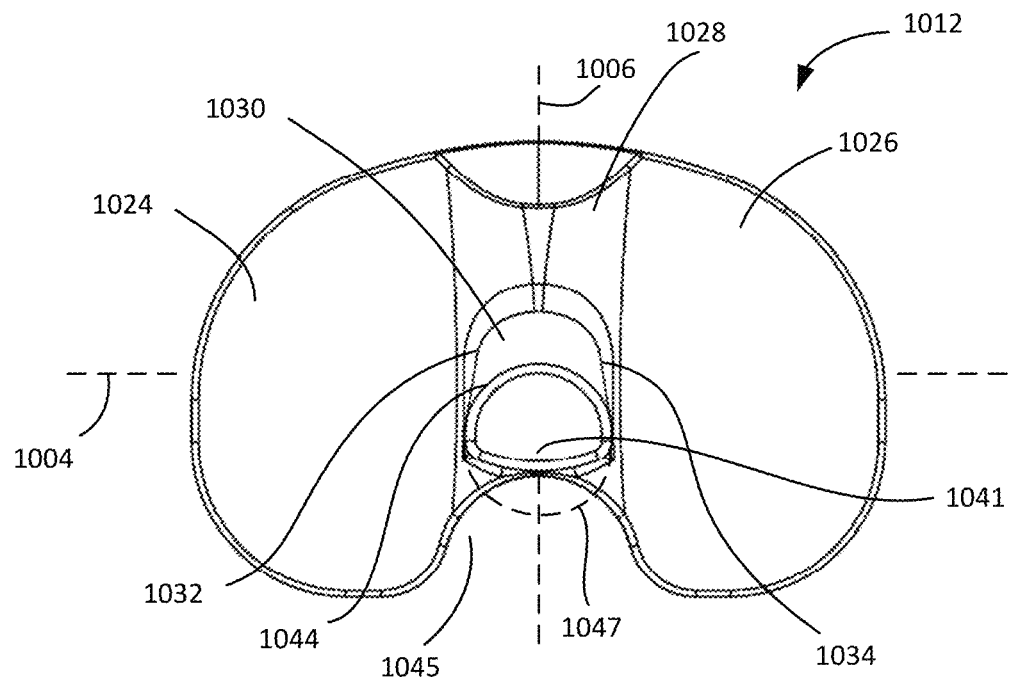
FIG. 16C is a superior view of the tibial insert of FIG. 14.
Figure 16D:
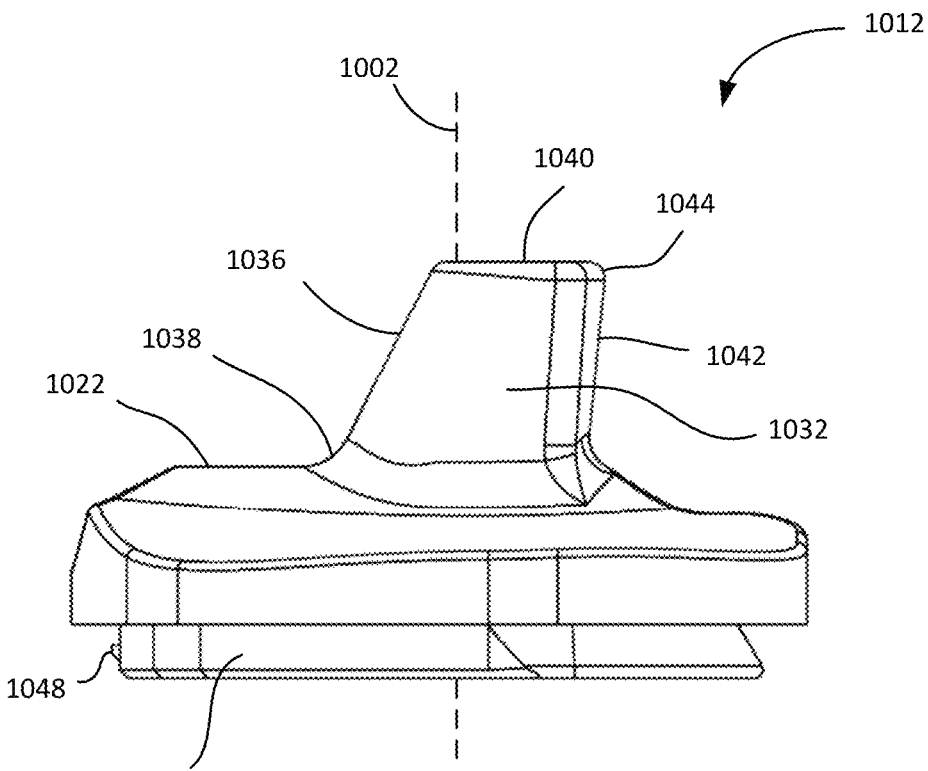
FIG. 16D is a medial side view of the tibial insert of FIG. 14.

Continuing with FIGS. 14-16D, the post 1030 may have an articulation surface 1031 extending around the post 1030 on the medial, posterior, lateral, and anterior aspects of the post 1030. The articulation surface 1031 may include a medial articulation surface 1032, a lateral articulation surface 1034, an anterior post surface 1036, and a posterior articulation surface 1042. The medial and lateral articulation surfaces 1032, 1034 may be non-parallel to one another and taper inward from the post superior end 1040 to the post base 1038 relative to an insert midline vertical axis 1002, as shown in FIGS. 16A and 16B. As shown in FIG. 16A, an angle θ between the vertical axis 1002 and each tapered surface 1032, 1034 may be about 6.5°, in at least one embodiment. Since the post 1030 may be bilaterally symmetrical, the angle θ may be the same on both the medial and lateral sides 1032, 1034 of the post 1030. In other embodiments of the disclosure, angle θ may range from about 6° to 11° degrees. The medial articulation surface 1032 may be continuous with the medial condylar articulation surface 1025, and the lateral articulation surface 1034 may be continuous with the lateral condylar articulation surface 1027. The anterior post surface 1036 may extend between the medial and lateral surfaces 1032, 1034 and may be convexly rounded. The anterior post surface 1036 may also taper outward from the post superior end 1040 to the post base 38 relative to the insert midline vertical axis 1002, as best seen in FIG. 16D. In other embodiments of the PS insert 1012, the anterior post surface 1036 may include less taper, more taper, and/or no taper. A midline medial-lateral axis 1004 and a mid-line anterior-posterior axis 1006 are also shown.

Referring to FIG. 16C, the boundary of the superior end 1040 may define a rounded rim 1044 shaped as a portion of a circle defined by a circular envelope 1047, as seen from a superior perspective. The superior end 1040 and rim 1044 may have a convex protrusion 1041 toward a posterior end of the post 1030 as shown, and may permit passage of the posterior cruciate ligament. The circular superior end 1040 with rim 1044 may provide increased rotational range of motion and surface contact against the femoral component 1014 in comparison to traditional posts with a more square or rectangular shape and no rim. Thus, the rounded superior end 1040 and rim 1044 may allow for greater surface contact with the femoral component 1014 in contrast to the mere point or edge contact that is achieved by traditional posts that do not have these features.

The PS femoral component 1014 depicted in FIGS. 14-15 may include augment fixation apertures 1080, impact driver apertures 1090, a cam element or cam bar 1050, and a box structure 1052 for providing posterior stabilization in place of absent ligaments. The cam bar 1050 may include a cam articulating surface 1051 which may contact the posterior articulation surface 1042 of the post 1030 during flexion. An internal articulation surface 1054 may reside on the inside of the box structure 1052 and may contact the post 1030 during articulation and rotation of the knee joint. The internal articulating surface 1054 may be concavely curved, and may contact the rim 1044 of the post 1030 during axial rotation of the knee joint about the post 1030. The PS femoral component 1014 may further include a medial condyle 1060 having a medial condylar articulation surface 1062, and a lateral condyle 1064 having a lateral condylar articulation surface 1066. The medial and lateral condylar articulation surfaces 1062, 1066 may articulate against the PS insert 1012 medial and lateral articulation surfaces 1025, 1027 respectively. A gap 1068 may be formed between the medial and lateral condyles 1060, 1064, with the cam bar 1050 extending medial-laterally across the gap 1068. The internal articulation surface 1054 may include a medial portion 1070 continuous with a lateral portion 1072. In the embodiment depicted, a fixation post 1074 may protrude superiorly from the PS femoral component 1014. However, in other embodiments of the PS femoral component 1014, the fixation post 1074 may be absent and/or other fixation features such as posts, spikes, pegs, webs, keels or teeth may be present to affix the PS femoral component 1014 to a prepared femur (not shown).

Figure 17:
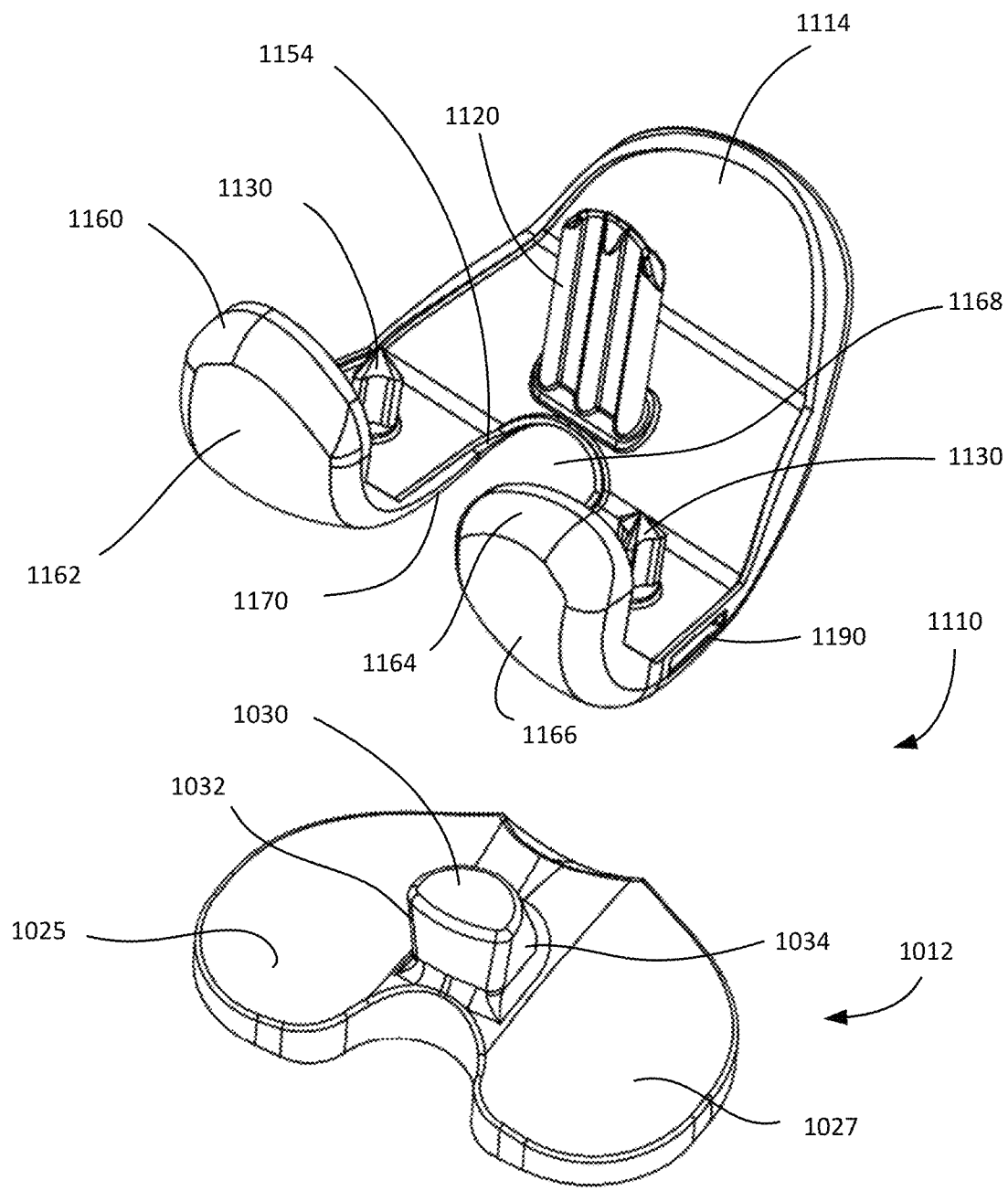
FIG. 17 is an exploded rear view of another assembly of the disclosure, including a cruciate retaining femoral component with a keel and the posterior stabilizing tibial insert of FIG. 14.
Figure 18:
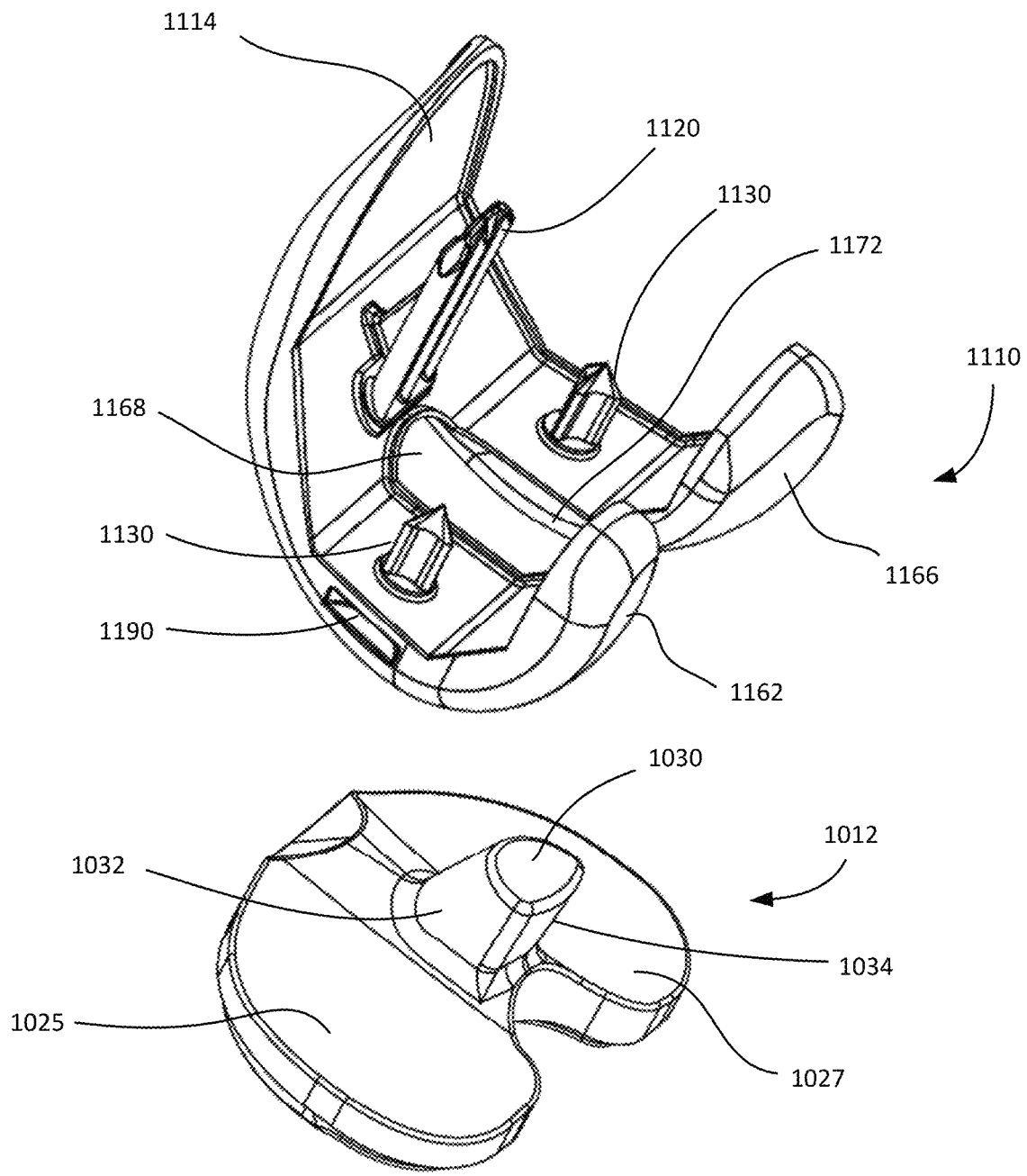
FIG. 18 is another exploded rear view of the assembly of FIG. 17.

Referring to FIGS. 17 and 18, another assembly 1110 embodiment of the disclosure may include the PS insert 1012 of FIGS. 14-16D coupled with a cruciate retaining femoral component 1114 (or "CR femoral component"). The CR femoral component 1114 may include a keel 1120, fixation members 1130, impact driver apertures 1190, and medial and lateral condyles 1160, 1164 with a gap 1168 formed between the condyles 1160, 1164. As a CR femoral component 1114, no cam bar or box may be present. The condyles 1160, 1164 may include medial and lateral condylar articulation surfaces 1162, 1166, and an internal articulation surface 1154 with medial and lateral portions 1170, 1172.

The tapered sides 1032, 1034 of the post 1030 may permit natural articulation of the CR femoral component 1114 with the PS insert 1012, which may not be achievable if the post 1030 were not tapered. For example, if the post 1030 had straight sides instead of tapered sides, the wider width of the post 1030 at the base of the post 1030 may interfere with the internal articulating surfaces 1170, 1172 of the condyles 1160, 1164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 1114, the resultant assembly 1110 may provide the native articulation and rotation of a cruciate retaining implant.

Figure 19:
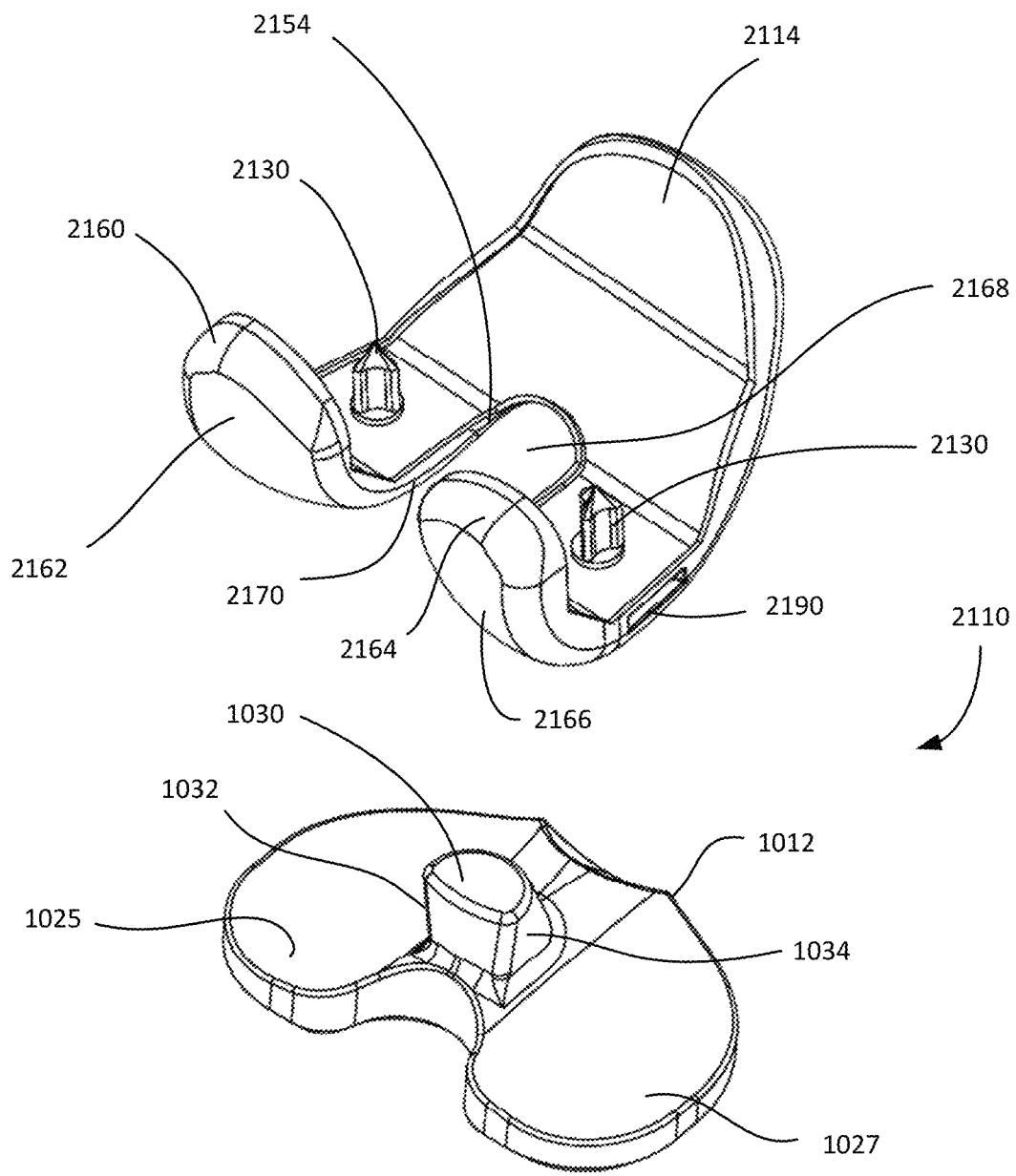
FIG. 19 is an exploded rear view of another assembly of the disclosure, including a cruciate retaining femoral component without a keel and the posterior stabilizing tibial insert of FIG. 14.
Figure 21A:
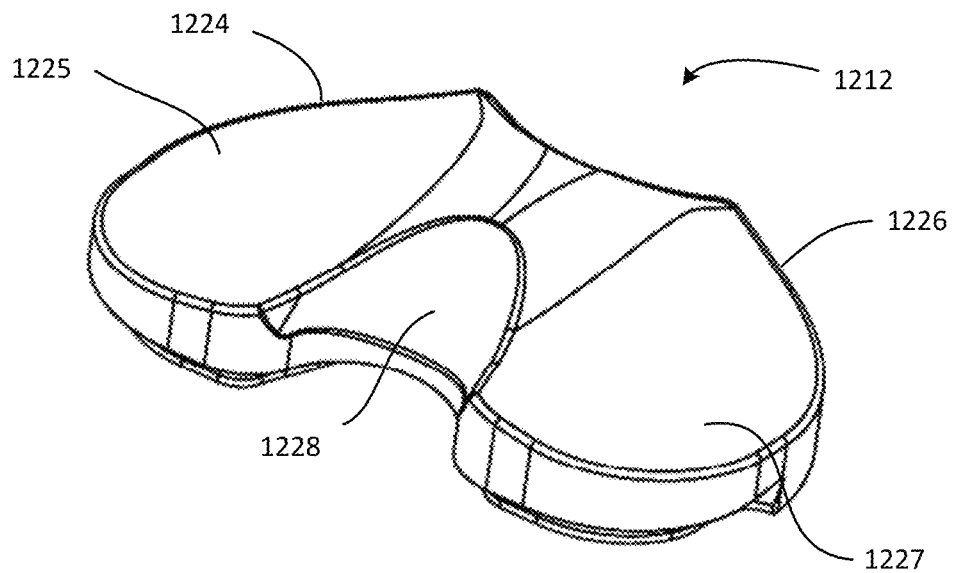
FIG. 21A is a perspective rear view of another tibial insert of the disclosure.
Figure 21B:
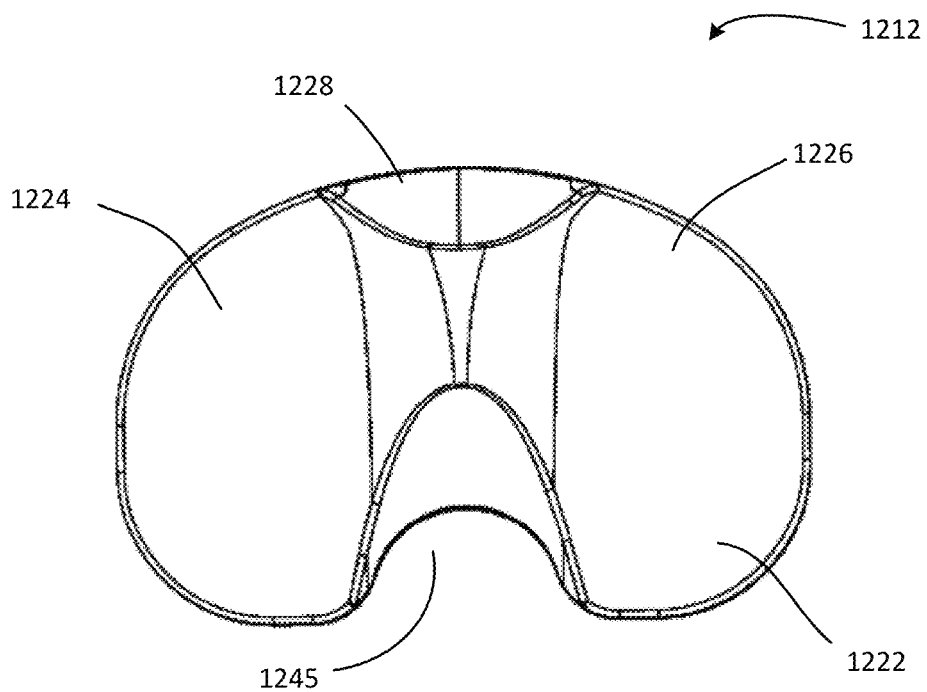
FIG. 21B is a top view of the tibial insert of FIG. 21A.
Figure 21C:
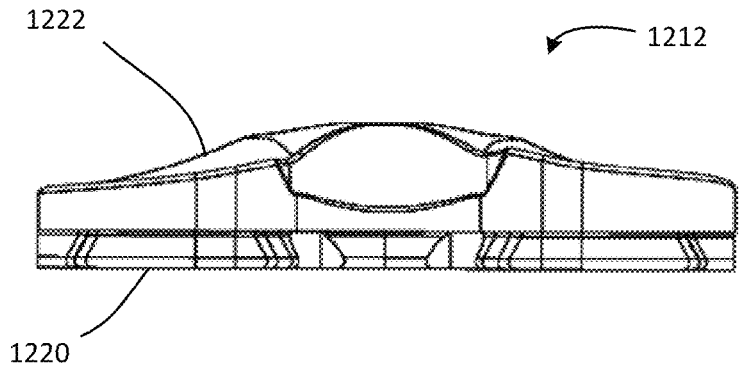
FIG. 21C is a posterior view of the tibial insert of FIG. 21A.
Figure 21D:
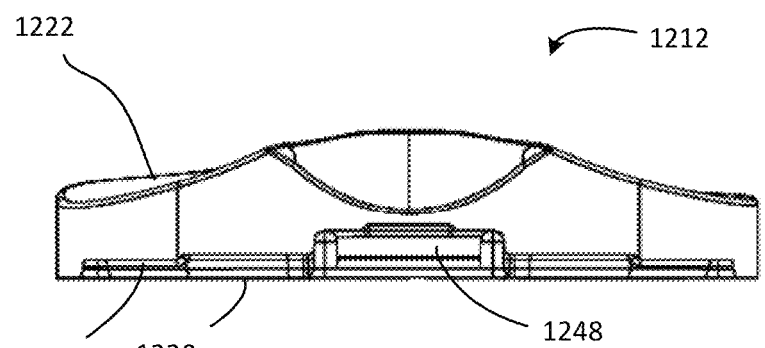
FIG. 21D is an anterior view of the tibial insert of FIG. 21A.
Figure 21E:
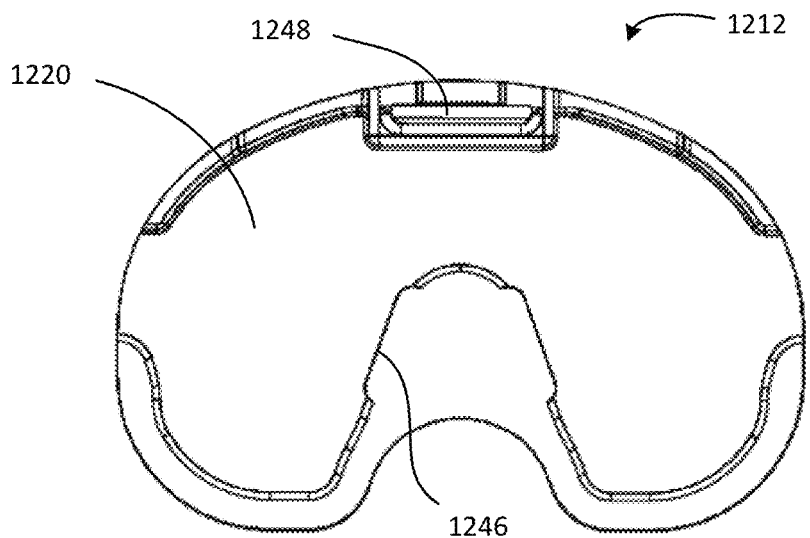
FIG. 21E is a bottom view of the tibial insert of FIG. 21A.

Referring to FIGS. 19 and 20, another assembly 2110 embodiment of the disclosure may include the PS insert 1012 of FIGS. 14-16D coupled with a cruciate retaining femoral component 2114 (or "CR femoral component"). The CR femoral component 2114 may not include a keel, as opposed to the CR femoral component 1114 shown in FIGS. 17 and 18, and the CR femoral component 2114 may be configured for cemented and/or cementless fixation to a femoral bone. The CR femoral component 2114 may include fixation members 2130, impact driver apertures 2190, and medial and lateral condyles 2160, 2164 with a gap 2168 formed between the condyles 2160, 2164. As a CR femoral component 2114, no cam bar or box may be present. The condyles 2160, 2164 may include medial and lateral condylar articulation surfaces 2162, 2166, and an internal articulation surface 2154 with medial and lateral portions 2170, 2172.

The tapered sides 1032, 1034 of the post 1030 may permit natural articulation of the CR femoral component 2114 with the PS insert 1012, which may not be achievable if the post 1030 were not tapered. For example, if the post 1030 had straight sides instead of tapered sides, the wider width of the post 1030 at the base 1038 of the post 1030 may interfere with the internal articulating surfaces 2170, 2172 of the condyles 2160, 2164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 2114, the resultant assembly 2110 may provide the native articulation and rotation of a cruciate retaining implant.

Referring to FIGS. 21A-21E, an alternative embodiment of a tibial insert 1212 is shown. The tibial insert 1212 may be referred to as a cruciate retaining tibial insert 1212 (or "CR insert"). In a system of the disclosure, the CR insert 1212 may be implanted with the CR femoral components 114, 1114, 2114 and a tibial baseplate component (not shown) to form a cruciate retaining knee prosthesis system. The CR insert 1212 may include a fixation side 1220, which may be an inferior side, opposite an articulation side 1222, which may be a superior side. The articulation side 1222 may include a medial articulation portion 1224 having a medial condylar articulation surface 1225 and a lateral articulation portion 1226 having a lateral condylar articulation surface 1227. A central portion 1228 may separate the medial articulation portion 1224 from the lateral articulation portion 1226. A recess 1245 may be formed posterior to the central portion 1228, between the medial and lateral articulation portions 1224, 1226, and may provide room for a posterior cruciate ligament. The CR insert 1212 may further include an insert base 1246 and an engagement feature 1248 for engagement with a tibial baseplate component.

The CR insert 1212 may be coupled with CR femoral components 114, 1114, 2114 to form a cruciate retaining assembly. This cruciate retaining assembly may be implanted with a suitable tibial baseplate as a complete cruciate retaining knee prosthesis. The CR insert 1212 may also be coupled with PS femoral components 14, 1014 to form a posterior stabilizing assembly and implanted with a suitable tibial baseplate as a complete posterior stabilizing knee prosthesis.

Figure 22A:
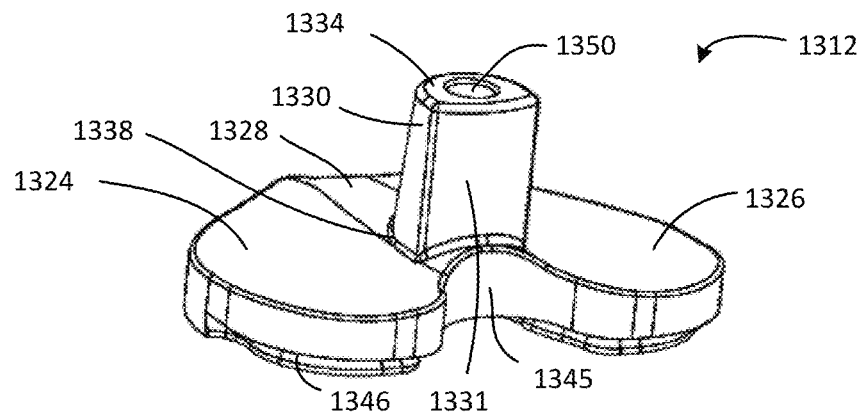
FIG. 22A is a perspective rear view of another tibial insert of the disclosure.
Figure 22B:
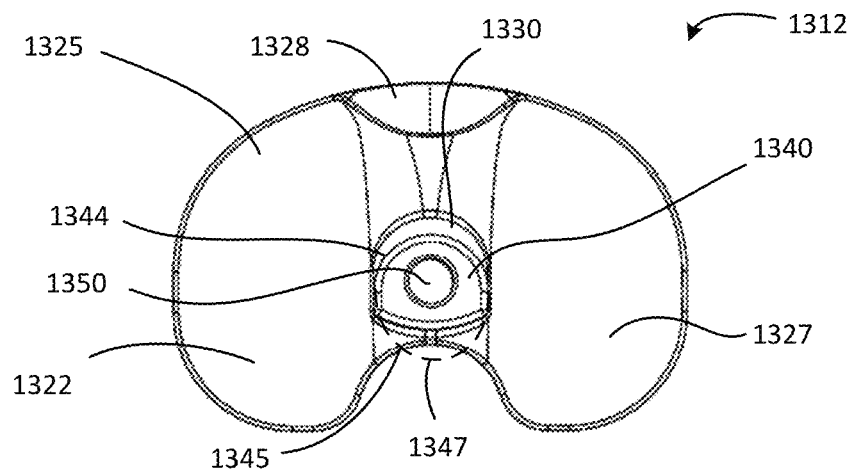
FIG. 22B is a top view of the tibial insert of FIG. 22A.
Figure 22C:
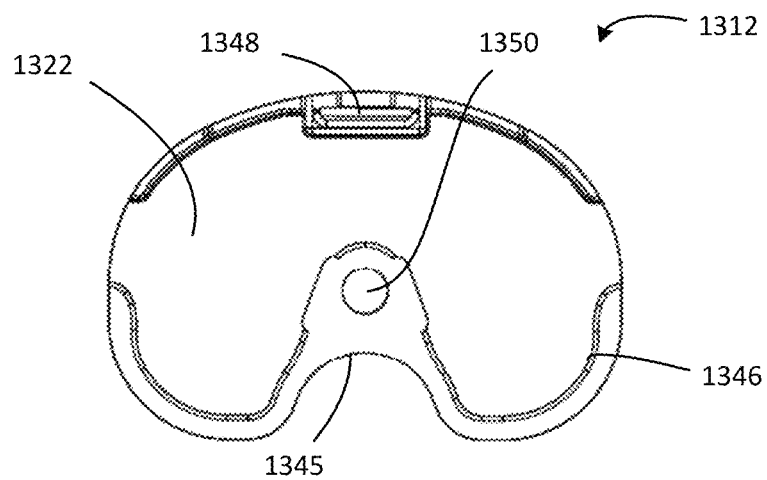
FIG. 22C is a bottom view of the tibial insert of FIG. 22A.
Figure 22D:
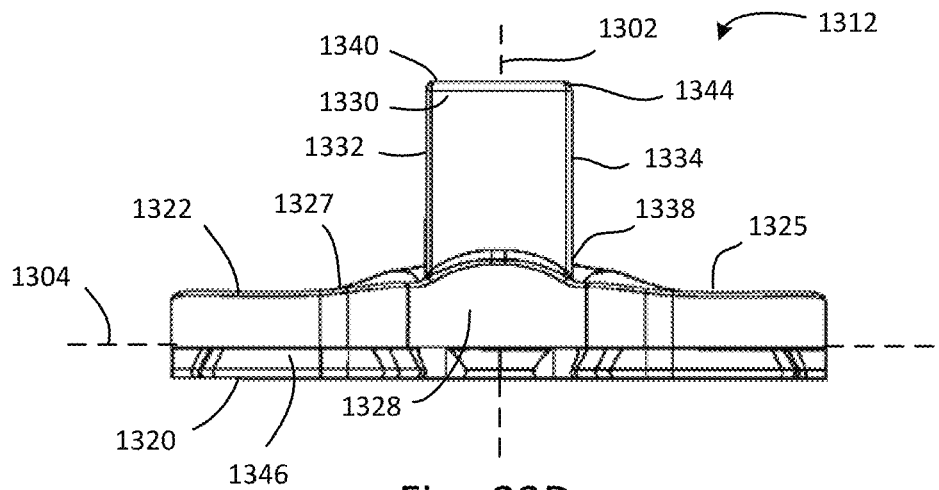
FIG. 22D is a posterior view of the tibial insert of FIG. 22A.
Figure 22E:
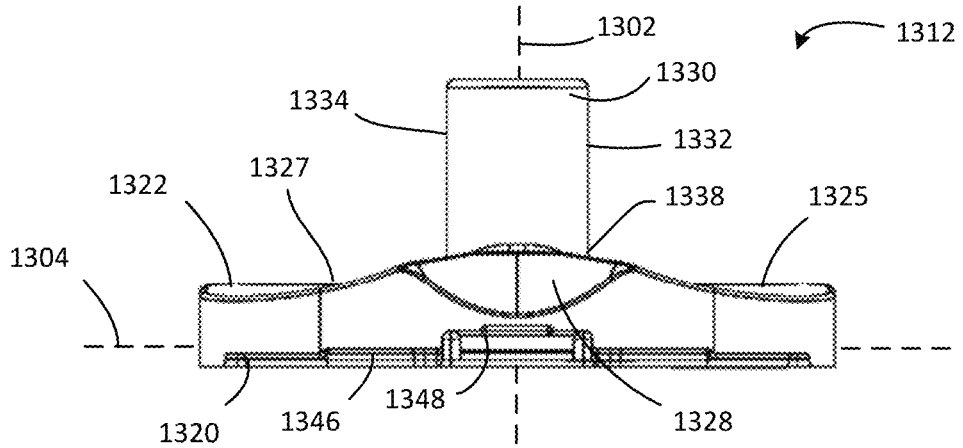
FIG. 22E is an anterior view of the tibial insert of FIG. 22A.

Referring to FIGS. 22A-22F, another alternative embodiment of a tibial insert 1312 is shown. The tibial insert 1312 may be referred to as a constrained condylar knee (CCK) tibial insert 1312 (or "CCK insert"). The CCK insert 1312 may include a fixation side 1320, which may be an inferior side, opposite an articulation side 1322, which may be a superior side. The articulation side 1322 may include a medial articulation portion 1324 having a medial condylar articulation surface 1325 and a lateral articulation portion 1326 having a lateral condylar articulation surface 1327. A central portion 1328 may separate the medial articulation portion 1324 from the lateral articulation portion 1326. A post 1330 may protrude superiorly from the central portion 1328, and extend from a post base 1338 to a top, or post superior end 1340. From the anterior perspective, as shown in FIG. 22E, and the posterior perspective, as shown in FIG. 22D, the post 1330 may have its maximum medial-lateral or horizontal width at the post superior end 1340 of the post 1330, and its minimum medial-lateral or horizontal width at the post base 1338 of the post 1330. The post 1330 may be bilaterally symmetrical from the anterior and posterior perspectives. The CCK insert 1312 may further include a posterior recess 1345, an insert base 1346, and an engagement feature 1348 for engagement with a tibial tray (not shown). An opening 1350 may be present in the superior surface of the post 1330.

Figure 22F:
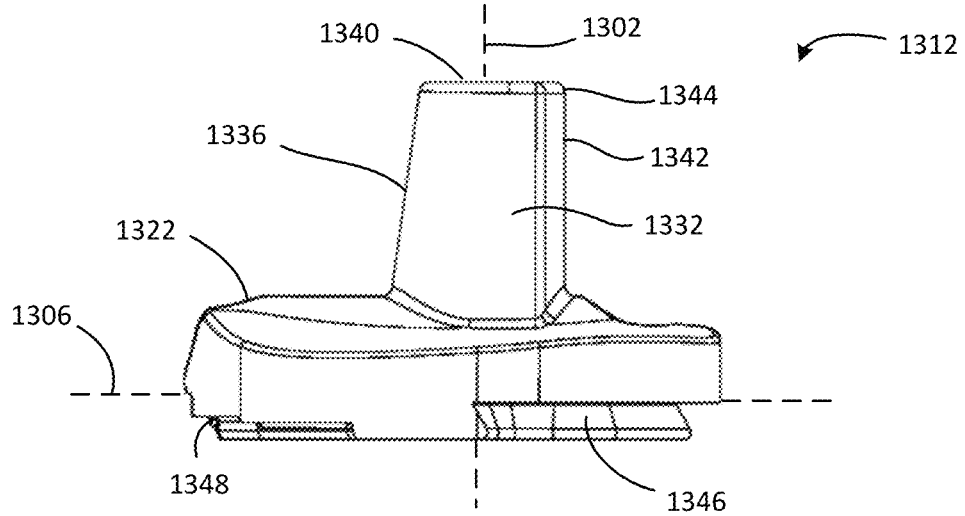
FIG. 22F is a medial side view of the tibial insert of FIG. 22A.

The post 1330 may have an articulation surface 1331 extending around the post 1330 on the medial, posterior, lateral, and anterior aspects of the post 1330. The articulation surface 1331 may include a medial articulation surface 1332, a lateral articulation surface 1334, an anterior post surface 1336, and a posterior articulation surface 1342. The medial and lateral articulation surfaces 1332, 1334 may taper slightly inward from the post superior end 1340 to the post base 1338 of the post 1330 relative to an insert midline vertical axis 1302. However, some embodiments of CCK insert 1312 may include less taper, more taper, and/or no taper of the medial and lateral articulation surfaces 1332, 1334. The medial articulation surface 1332 may be continuous with the medial condylar articulation surface 1325, and the lateral articulation surface 1334 may be continuous with the lateral condylar articulation surface 1327. The anterior post surface 1336 may extend between the medial and lateral articulation surfaces 1332, 1334 and may be convexly rounded. The anterior post surface 1336 may taper outward from the post superior end 1340 to the post base 1338 relative to the midline axis 1302, as best seen in FIG. 22F. In other embodiments of the CCK insert 1312, the anterior post surface 1336 may include less taper, more taper, and/or no taper. The post 1330 of the CCK insert 1312 may be wider and bigger in diameter than the post 30 of PS insert 12, for example to provide increased stability in the case of removal of the collateral ligaments. A midline medial-lateral axis 1304 and a mid-line anterior-posterior axis 1306 are also shown in FIGS. 22D through 22F.

Referring to FIG. 22B, the boundary of the post superior end 1340 may define a rounded rim 1344 shaped as a portion of a circle, from a superior perspective, and may have a convex protrusion toward a posterior end of the post 1330. The post superior end 1340 and rim 1344 may be semicircular as shown, however the rim 1344 may define a circular envelope 1347. The post superior end 1340 may be circular and the rim 1344 may provide increased surface contact and rotational range of motion when coupled and implanted with the PS femoral components disclosed herein in comparison to traditionally shaped posts with a more square or rectangular shaped post. Thus, the rounded post superior end 1340 and rim 1344 may allow for greater surface contact with the femoral components 14, 1014 in contrast to the mere point or edge contact that is achieved by traditional posts that do not include these features.

The CCK insert 1312 may be coupled with the PS femoral components 14, 1014 to form a constrained condylar knee assembly, and this assembly may be implanted with a suitable tibial baseplate as a constrained condylar knee prosthesis. The CCK insert 1312 may also be coupled with any of the CR femoral components disclosed herein and implanted with a suitable tibial baseplate. Thus, all of the tibial inserts disclosed herein are interchangeable with all of the CR and PS femoral components disclosed herein.

Any of the tibial inserts, CR femoral components, and/or PS femoral components disclosed herein may be grouped together in any number or combination as one or more modular knee replacement systems or kits. A particular kit may include a CR femoral component, a PS insert, and a CR insert. Yet another particular kit may include a PS femoral component, a PS insert, a CR insert, and a CCK insert. Suitable tibial baseplate components may also be included with any kit. Moreover, any of the tibial inserts disclosed herein may be formed of vitamin E polyethylene, highly cross linked polyethylene, ultra-high molecular weight polyethylene (UHMWPE), and/or the like.

In an example method of the disclosure, a patient may initially experience compromise of the anterior cruciate ligament. The ACL may be removed, and a CR type prosthesis may be implanted, including a CR femoral component, a CR insert, and a tibial baseplate component. Later, the same patient may experience compromise of the PCL and may need additional stabilization of the knee joint. The PCL may be removed, the CR tibial insert may be removed, and a PS tibial insert of the disclosure may be inserted between the originally implanted CR femoral component and the tibial baseplate component, thus providing additional stability for the missing PCL. Even later, the same patient may experience instability of the collateral ligaments. The PS tibial insert may be removed, and the CCK tibial insert of the disclosure may be inserted between the originally implanted CR femoral component and the tibial baseplate component. Thus, the patient may progress from a CR knee prosthesis, to a PS knee prosthesis, and finally to a CCK knee prosthesis without requiring replacement of the originally implanted femoral and/or tibial baseplate components. The interchangeability of the inserts permits replacement of only the tibial insert component in order to provide increasing levels of support and stability to the knee joint.

In another example method of the disclosure, a patient may initially experience compromise of both the ACL and the PCL. These ligaments may be removed, and a PS type prosthesis may be implanted, including a PS femoral component, a PS insert, and a tibial baseplate component. Later, the same patient may experience instability of the collateral ligaments. The PS insert may be removed, and a CCK insert may be inserted between the originally implanted PS femoral component and the tibial baseplate component. Thus, the patient may progress from a PS knee prosthesis to a CCK knee prosthesis without requiring replacement of the originally implanted PS femoral component and tibial baseplate component.

Figure 23A:
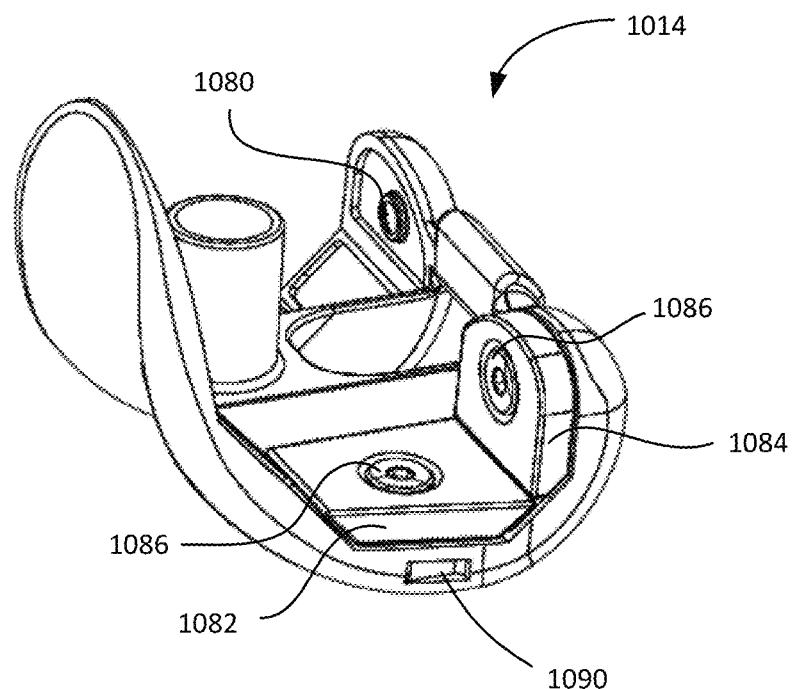
FIG. 23A is a perspective front view of the femoral component of FIG. 14 coupled to one or more augments of the present disclosure.
Figure 23B:
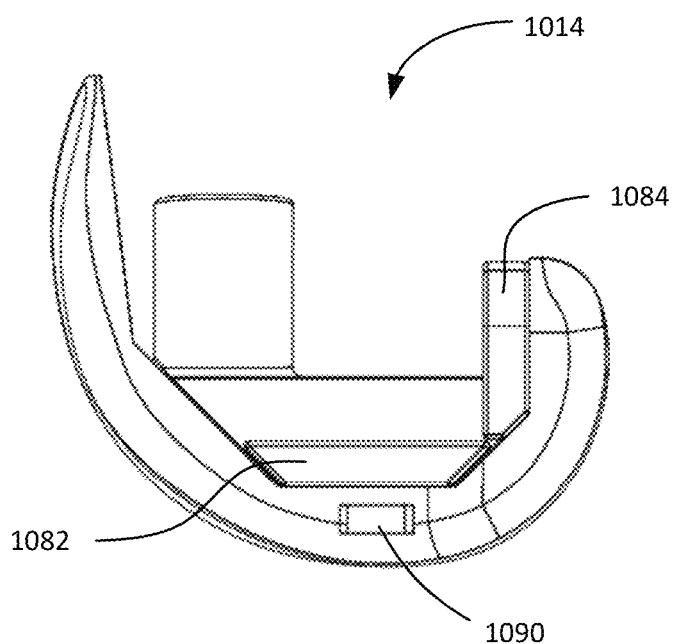
FIG. 23B is a medial side view of the femoral component of FIG. 23A.

Referring now to FIGS. 23A-B, FIG. 23A is a perspective front view of the femoral component 1014 of FIG. 14 coupled to one or more augments 1082, 1084 of the present disclosure and FIG. 23B is a medial side view of the femoral component 1014 of FIG. 23A. As briefly mentioned above with reference to FIGS. 14 and 15, the femoral component 1014 may include augment fixation apertures 1080 that may be configured to secure the one or more augments 1082, 1084 to the femoral component 1014, as well as impact driver apertures 1090 configured to receive a femoral component impact driver tool (not shown) to allow a surgeon to press fit the femoral component 1014 to the end of a prepared femur. The augments 1082, 1084 may be secured to the femoral component 1014 with fixation members 1086 and the augments 1082, 1084 may generally act to replace missing and/or compromised femoral bone and allow the femoral component 1014 to be adequately secured to a femoral bone under such conditions.

Figure 24A:
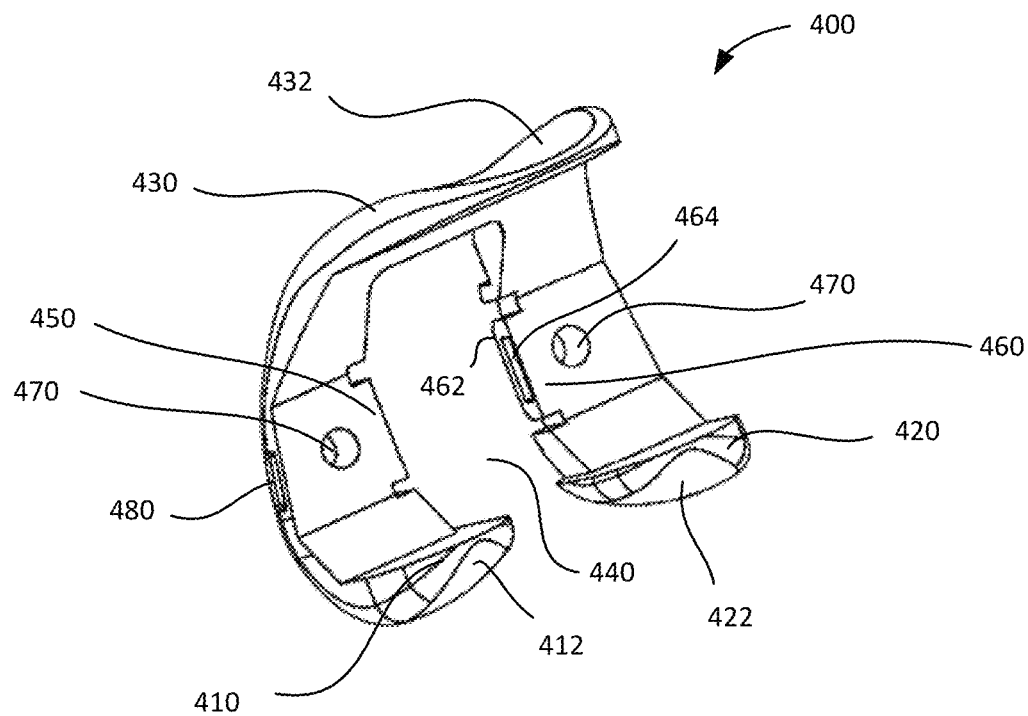
FIG. 24A is a perspective top view of a femoral trial component of the disclosure.
Figure 24B:
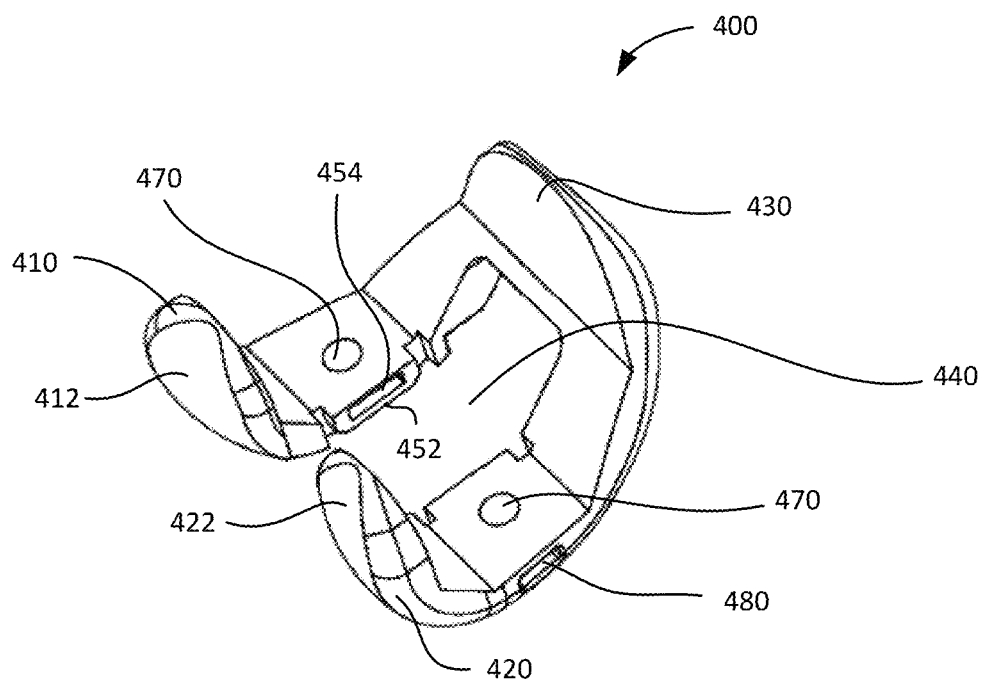
FIG. 24B is a perspective rear view of the femoral trial component of FIG. 24A.
Figure 24C:
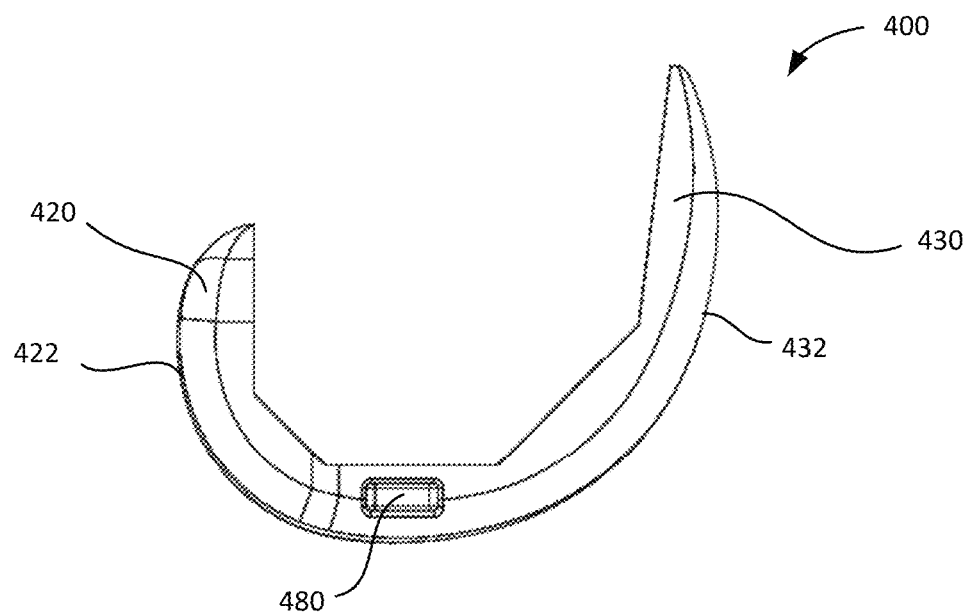
FIG. 24C is a lateral side view of the femoral trial component of FIG. 24A.
Figure 24D:
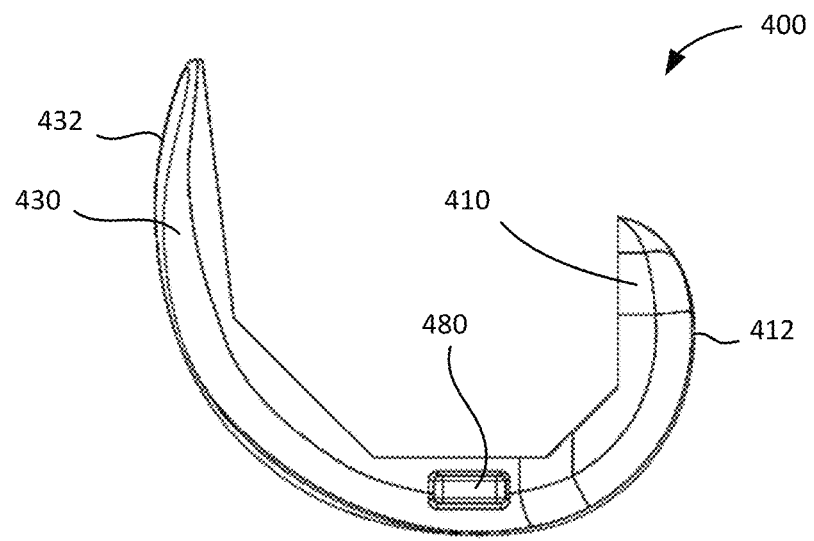
FIG. 24D is a medial side view of the femoral trial component of FIG. 24A.
Figure 24E:
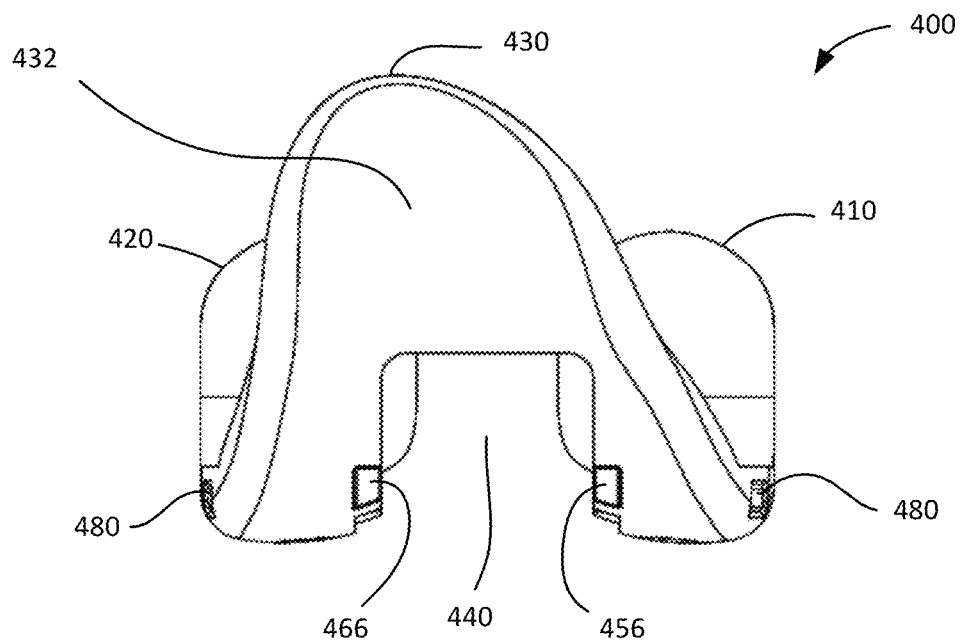
FIG. 24E is an anterior view of the femoral trial component of FIG. 24A.
Figure 24F:
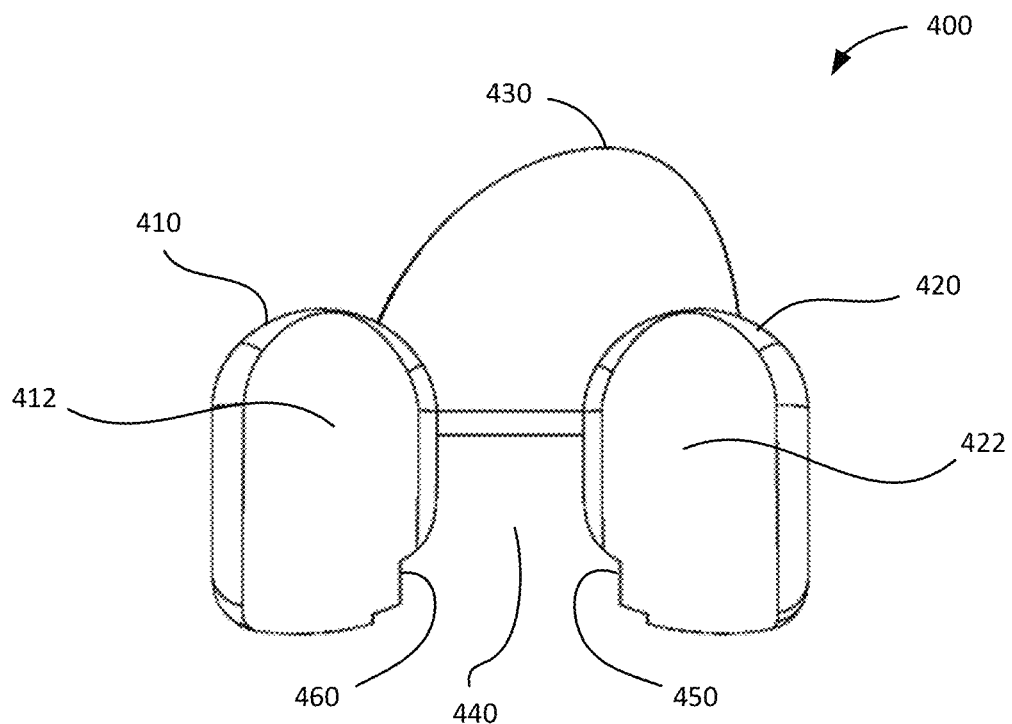
FIG. 24F is a posterior view of the femoral trial component of FIG. 24A.
Figure 24G:
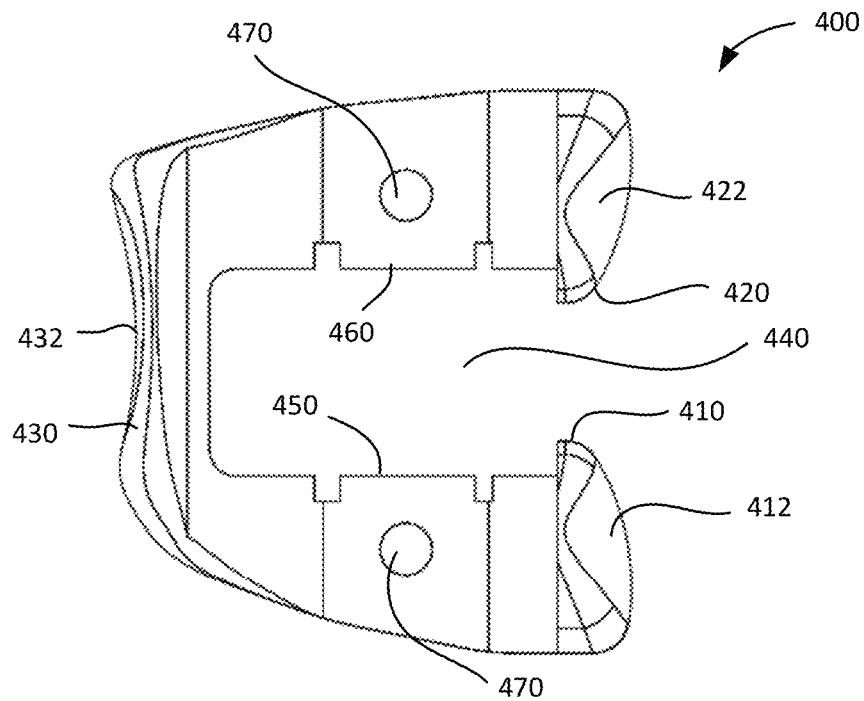
FIG. 24G is a superior view of the femoral trial component of FIG. 24A.
Figure 24H:
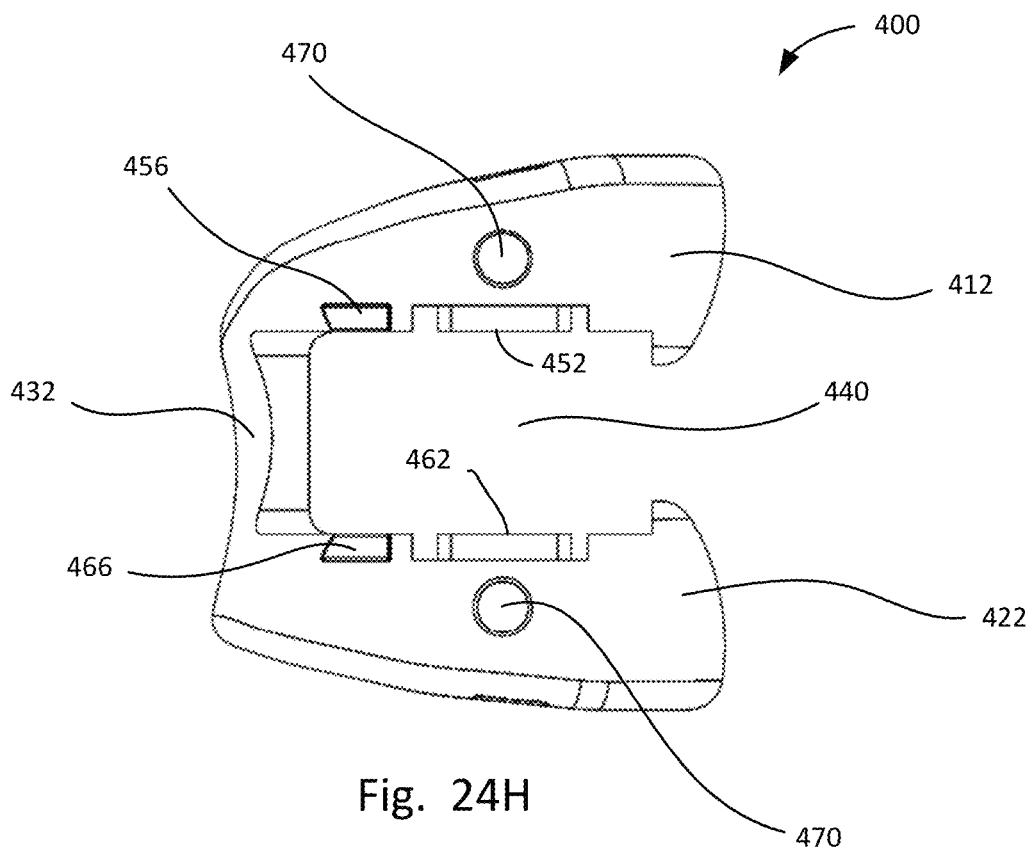
FIG. 24H is an inferior view of the femoral trial component of FIG. 24A.

Referring now to FIGS. 24A-H, a femoral trial component 400 of the disclosure is illustrated in FIGS. 24A-H. In particular, FIG. 24A shows a perspective top view of a femoral trial component of the disclosure, FIG. 24B shows a perspective rear view of the femoral trial component of FIG. 24A, FIG. 24C shows a lateral side view of the femoral trial component of FIG. 24A, FIG. 24D shows a medial side view of the femoral trial component of FIG. 24A, FIG. 24E shows an anterior view of the femoral trial component of FIG. 24A, FIG. 24F shows a posterior view of the femoral trial component of FIG. 24A, FIG. 24G shows a superior view of the femoral trial component of FIG. 24A, and FIG. 24H shows an inferior view of the femoral trial component of FIG. 24A.

The femoral trial component 400 may be referred to as a universal femoral trial component 400 because the femoral trial component 400 may be used as part of a universal femoral trial system for preparing and trialing a femoral bone of a patient (not shown) to receive a plurality of different femoral implant types, as will be discussed in more detail below. The femoral trial component 400 may include a medial condyle 410 having a medial condylar articulation surface 412, a lateral condyle 420 having a lateral condylar articulation surface 422, an attachment aperture 440 located intermediate the medial condyle 410 and the lateral condyle 420, a patellar projection 430 located anterior to the medial condyle 410 and the lateral condyle 420, a patellar articulation surface 432, fixation member drill apertures 470, impact driver apertures 480, medial attachment features 450 proximate the medial condyle 410, and lateral attachment features 460 proximate the lateral condyle 420. The medial attachment features 450 may further include a medial attachment projection 452, a medial attachment aperture 454 formed within the medial attachment projection 452, and a medial attachment recess 456. The lateral attachment features 460 may likewise include a lateral attachment projection 462, a lateral attachment aperture 464 formed within the lateral attachment projection 462, and a lateral attachment recess 466.

In practice, the femoral trial component 400 may be coupled to a partially prepared distal end of a femur (not shown). For example, a partially prepared distal end of a femur may include five distal cuts that are made to the distal end of the femur using standard techniques and tools (not shown) that are well known in the art. These five cuts may be made to correspond in both shape and angle to the five surfaces on the inner portion of the femoral trial component 400, as best seen in FIGS. 24C and 24D. The femoral trial component 400 may then be press fit onto the partially prepared distal end of the femur and the femoral trial component 400 may also be aligned relative to the distal end of the femur in the medial-lateral directions. The femoral trial component 400 may then be used to further prepare the distal end of the femur and/or perform one or more trial operations with the femoral trial component 400 still in place on the distal end of a femur.

For example, the attachment aperture 440 formed in the femoral trial component 400, along with the medial and lateral attachment features 450, 460, may be configured to receive any of a plurality of removably couplable femoral bone preparation attachments and/or any of a plurality of femoral trial attachments. Example femoral bone preparation attachments may include a posterior stabilizing notch cutting guide assembly 500, an augment cutting guide assembly (not shown), and a drill and broach guide assembly 700, as will be discussed in more detail below. Each of these femoral bone preparation attachments may be configured to removably couple to the universal femoral trial component 400 to allow a femoral bone of a patient to be selectively modified and prepared to receive a selected femoral implant type. Example femoral trial attachments may include a cruciate retaining trial attachment 800 including a cruciate retaining central portion articulation surface 810 and a posterior stabilizing trial attachment 600 including a posterior stabilizing central portion articulation surface 610, as will be discussed in more detail below. The cruciate retaining trial attachment 800 and the posterior stabilizing trial attachment 600 may each be configured to removably couple to the universal femoral trial component 400 to provide a central portion articulation surface 610, 810 above the attachment aperture 440 and allow for trialing of an articulation surface for a selected femoral implant type that includes a medial condylar articulation surface, a lateral condylar articulation surface, and a central portion articulation surface, for the selected femoral implant type. In this manner, the femoral bone preparation attachments and the femoral trial attachments may be used to help finish preparing the femur of the patient to receive any type of femoral component disclosed herein, and/or further perform one or more trial operations with the femoral trial component 400 still in place on the femur, as will be discussed in more detail below.

Figure 35A:
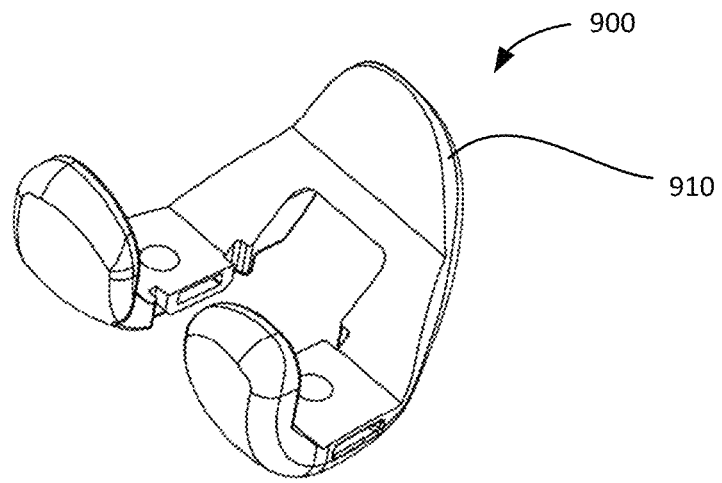
FIG. 35A is a perspective rear view of another femoral trial component of the disclosure.
Figure 35B:
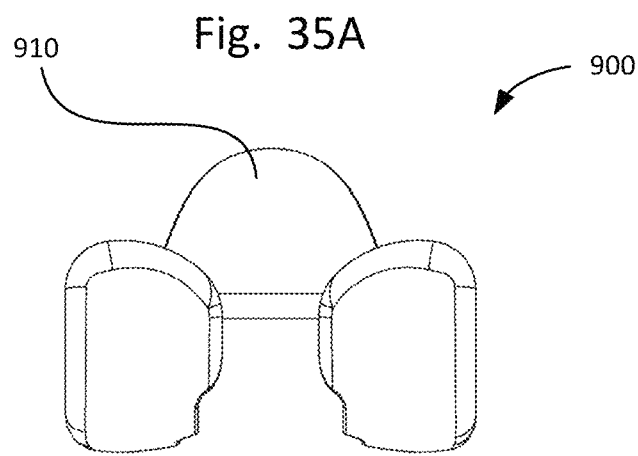
FIG. 35B is a posterior view of the femoral trial component of FIG. 35A.
Figure 35C:
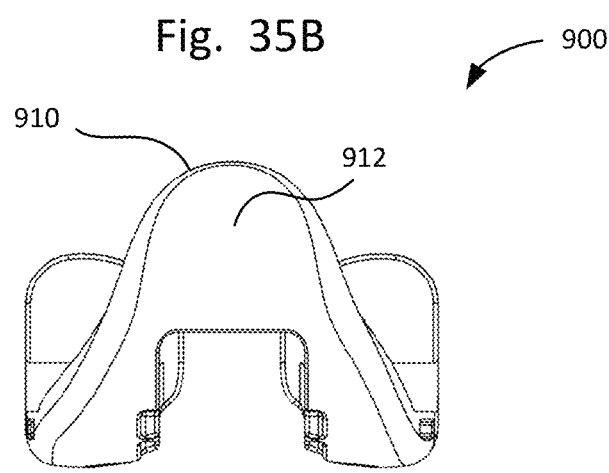
FIG. 35C is an anterior view of the femoral trial component of FIG. 35A.

The femoral trial component 400 shown in FIGS. 24A-H is a right side femoral trial component 400 having a patellar projection 430 with a right angled medial-lateral shape, as best seen in FIGS. 24E and 24F, which mimics the patellar region of a right femur (not shown). Note how the patellar projection 430 angles towards the right in the posterior view of the femoral trial component 400 shown in FIG. 24F and towards the left in the anterior view of the femoral trial component 400 shown in FIG. 24E. A left side femoral trial component (not shown) will have a patellar projection 430 shape that is a mirror image of that shown in FIGS. 24E and 24F, having a left angled medial-lateral shape that mimics the patellar region of a left femur (not shown). In another embodiment of the disclosure illustrated in FIGS. 35A-C, a universal femoral trial component 900 may include a patellar projection 910 with a universal shape that does not angle towards the right or left, but rather, the patellar projection 910 in this embodiment may have a symmetrical medial-lateral shape. In this manner, the universal femoral trial component 900 shown in FIGS. 35A-C has a universal shape that may be used to prepare and trial both right and left side femurs. The patellar projection 910 may have a patellar articular surface 912.

Figure 25A:
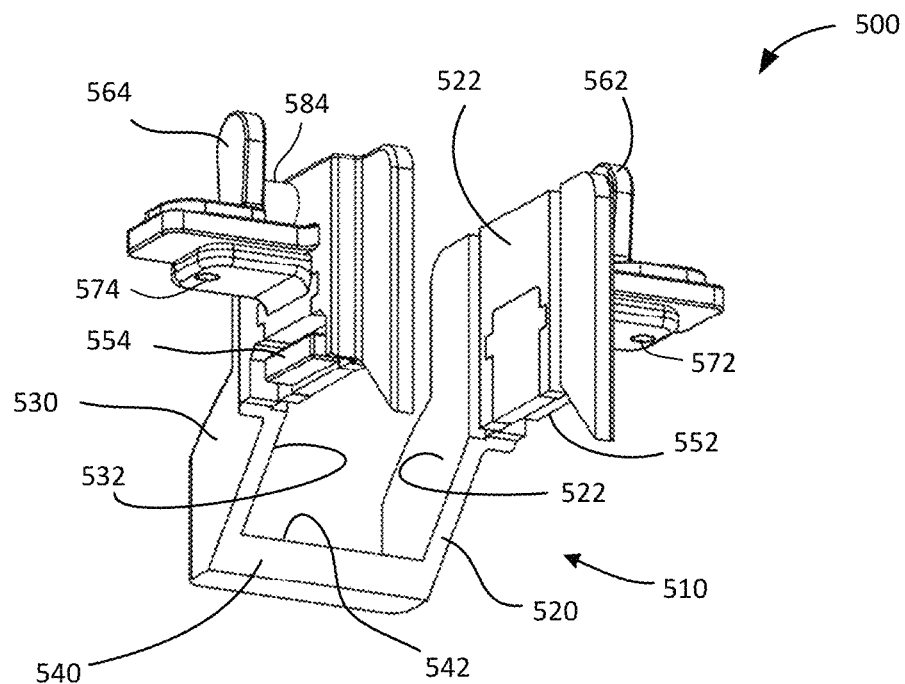
FIG. 25A is a perspective rear view of a posterior stabilizing notch cutting guide assembly of the disclosure.
Figure 25B:
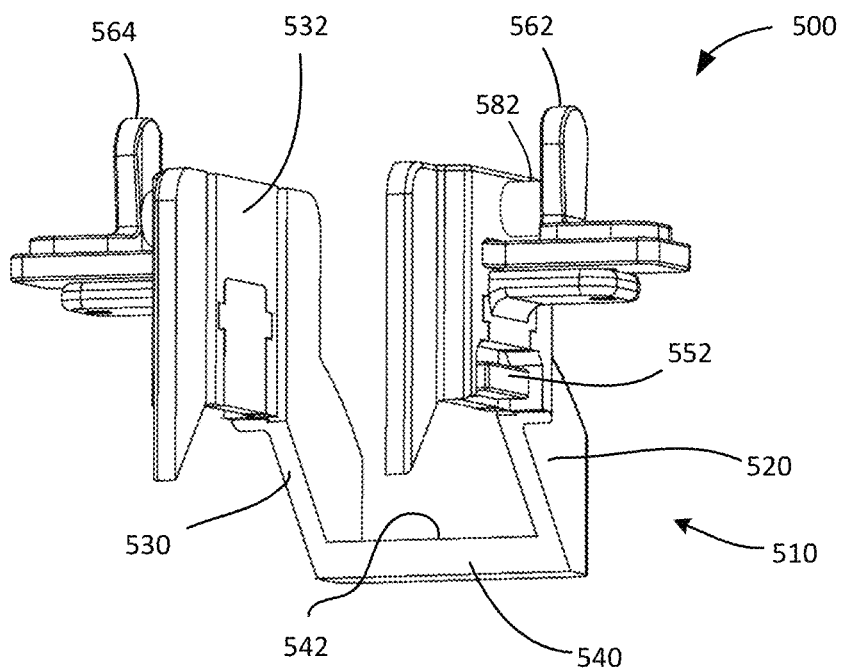
FIG. 25B is another perspective rear view of the posterior stabilizing notch cutting guide assembly of FIG. 25A.
Figure 25C:
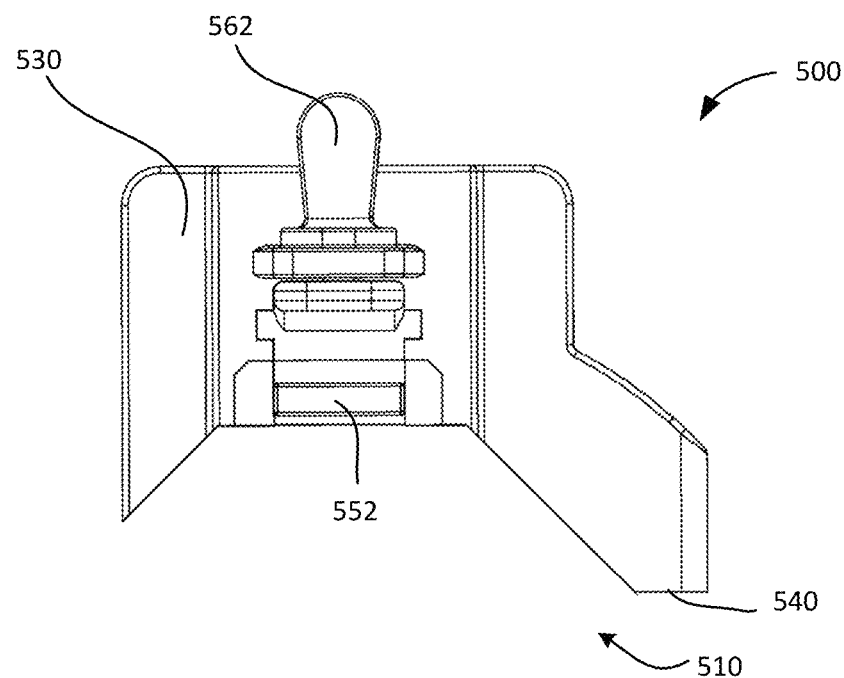
FIG. 25C is a medial side view of the posterior stabilizing notch cutting guide assembly of FIG. 25A.
Figure 25D:
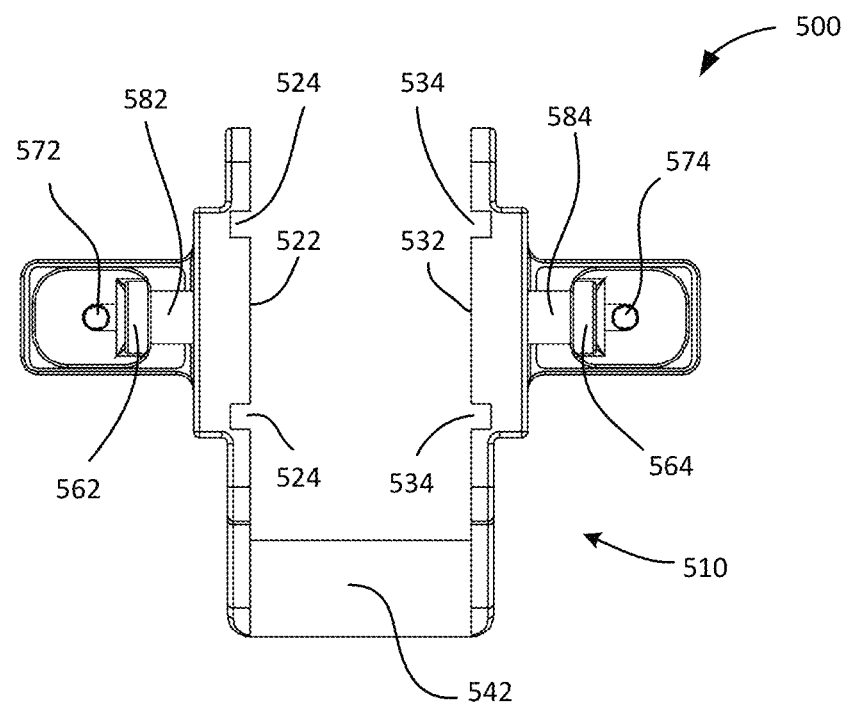
FIG. 25D is a top view of the posterior stabilizing notch cutting guide assembly of FIG. 25A.
Figure 26:
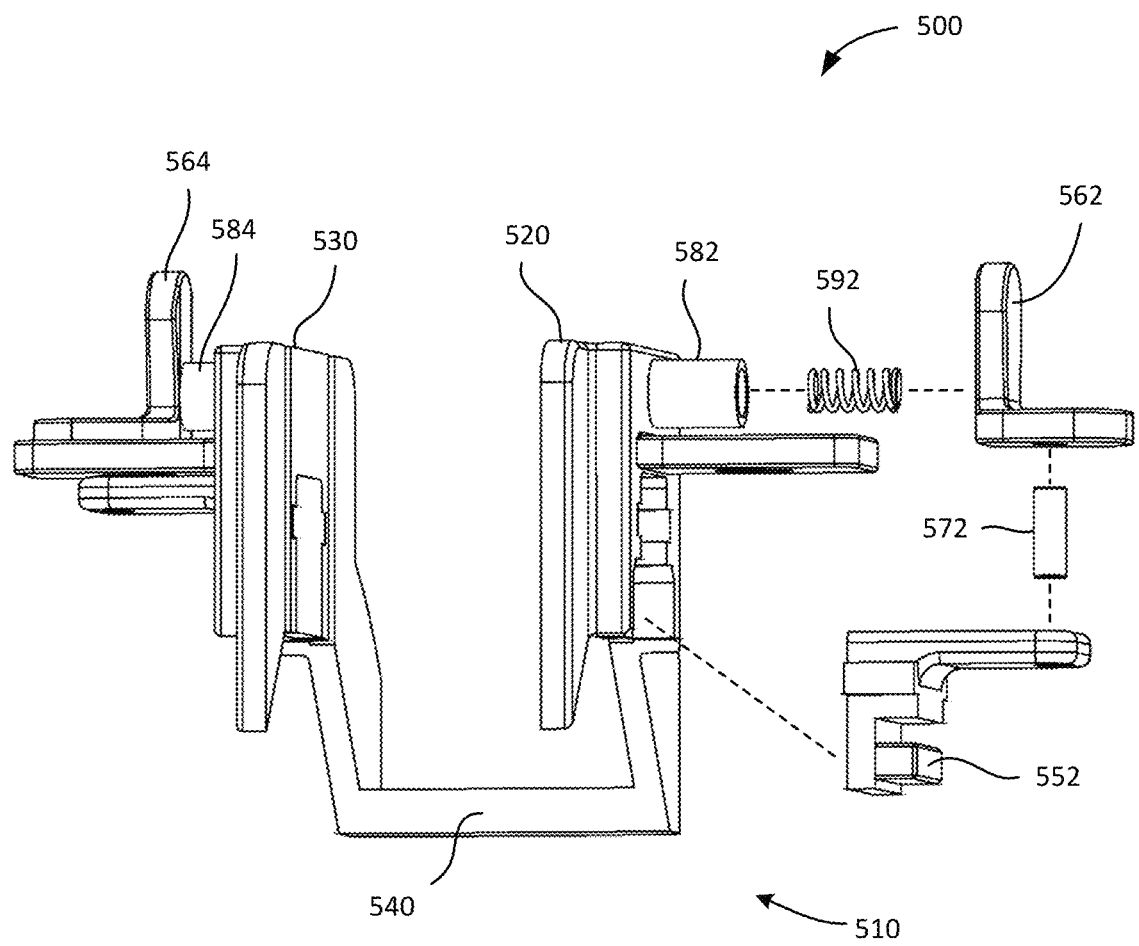
FIG. 26 is a partial exploded view of the posterior stabilizing notch cutting guide assembly of FIG. 25A.

FIGS. 25A-26 illustrate a posterior stabilizing notch cutting guide assembly 500 that may be used with the femoral trial component 400 shown in FIGS. 24A-H to help prepare a femur of a patient to receive a PS femoral component of the present disclosure by guiding bone resection. In particular, FIG. 25A is a perspective rear view of the posterior stabilizing notch cutting guide assembly 500, FIG. 25B is another perspective rear view of the posterior stabilizing notch cutting guide assembly 500, FIG. 25C is a medial side view of the posterior stabilizing notch cutting guide assembly 500, FIG. 25D is a top view of the posterior stabilizing notch cutting guide assembly 500, and FIG. 26 is a partial exploded view of the posterior stabilizing notch cutting guide assembly 500.

The posterior stabilizing notch cutting guide assembly 500 may include a posterior stabilizing notch cutting guide body 510 that includes a medial member 520 having a medial cutting guide surface 522 and medial channels 524 formed therein, a lateral member 530 having a lateral cutting guide surface 532 and lateral channels 534 formed therein, and a patellar member 540 having a patellar cutting guide surface 542.

The posterior stabilizing notch cutting guide assembly 500 may also include a locking mechanism which may include: a first locking member 552, a second locking member 554, a first release lever 562 coupled to the first locking member 552 via a first pin 572, a second release lever 564 coupled to the second locking member 554 via a second pin 574, a first resilient member 592 located between the first release lever 562 and the posterior stabilizing notch cutting guide body 510, with the first resilient member 592 housed in a first resilient member housing 582, a second resilient member (not shown) similarly located between the second release lever 564 and the posterior stabilizing notch cutting guide body 510, with the second resilient member housed in a second resilient member housing 584.

The first resilient member 592 may be configured to apply a biasing force that acts to push the first locking member 552 away from the posterior stabilizing notch cutting guide body 510 in the medial direction and the second resilient member may be configured to apply a biasing force that acts to push the second locking member 554 away from the posterior stabilizing notch cutting guide body 510 in the lateral direction.

Figure 27A:
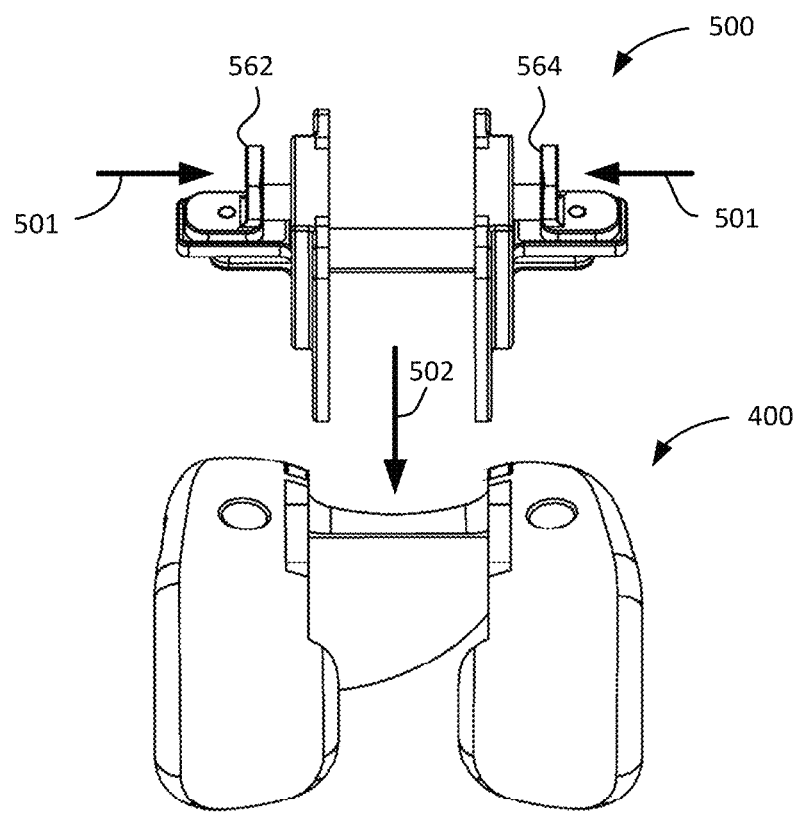
FIG. 27A is a posterior view of the posterior stabilizing notch cutting guide assembly of FIG. 25A above the femoral trial component of FIG. 24A.
Figure 27B:
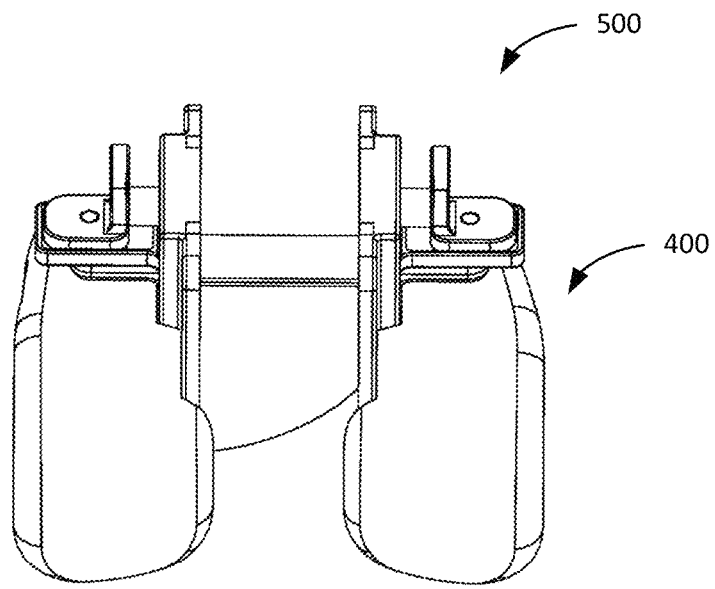
FIG. 27B is posterior view of the posterior stabilizing notch cutting guide assembly of FIG. 27A coupled to the femoral trial component of FIG. 27A.

Referring to FIGS. 27A and 27B, the posterior stabilizing notch cutting guide assembly 500 may be removably coupled to the universal femoral trial component 400 by squeezing the first release lever 562 and the second release lever 564 together toward each other (see arrows 501 in FIG. 27A) in order to overcome the biasing forces of the first resilient member 592 and the second resilient member; then inserting the posterior stabilizing notch cutting guide assembly 500 into the attachment aperture 440 of the universal femoral trial component 400 (see arrow 502 in FIG. 27A); and finally releasing the first release lever 562 and the second release lever 564 to allow the biasing forces of the first resilient member 592 and the second resilient member to push the first locking member 552 and the second locking member 554 away from the posterior stabilizing notch cutting guide body 510, causing the first locking member 552 to enter within the medial attachment aperture 454 of the femoral trial component 400 and the second locking member 554 to enter within the lateral attachment aperture 464 of the femoral trial component 400 to couple the posterior stabilizing notch cutting guide assembly 500 to the universal femoral trial component 400, as shown in FIG. 27B.

Figure 28A:
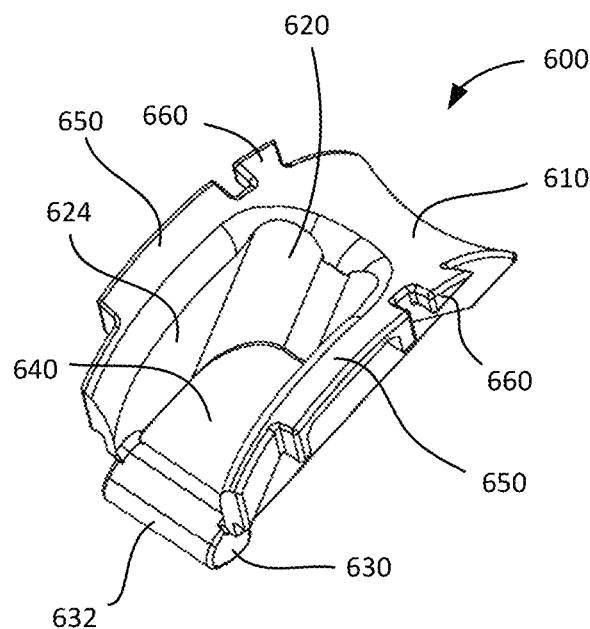
FIG. 28A is a perspective rear view of a posterior stabilizing trial attachment of the disclosure.
Figure 28B:
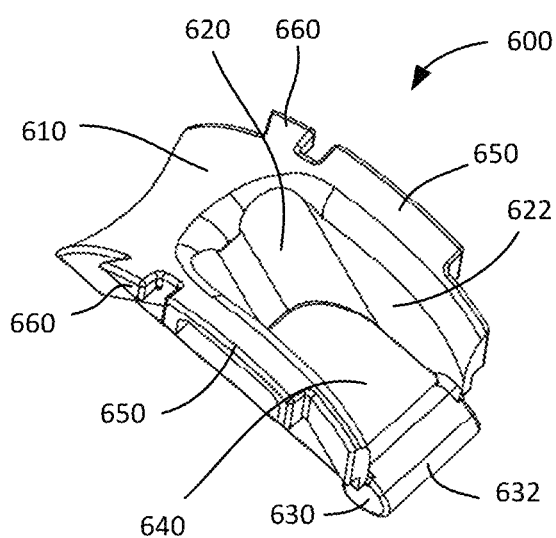
FIG. 28B is another perspective rear view of the posterior stabilizing trial attachment of FIG. 28A.
Figure 28C:
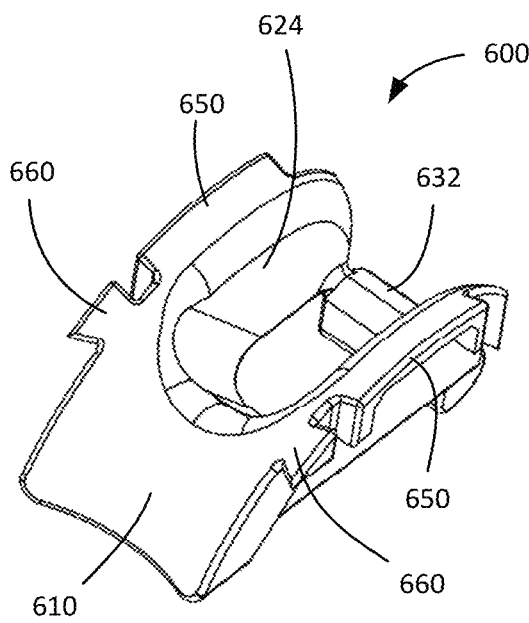
FIG. 28C is a perspective front view of the posterior stabilizing trial attachment of FIG. 28A.
Figure 28D:
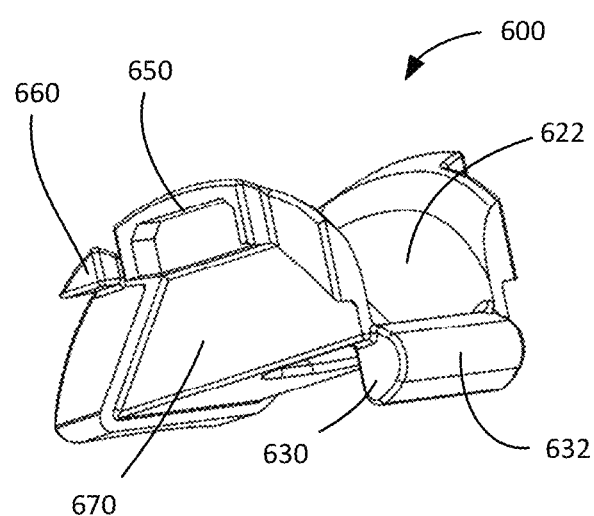
FIG. 28D is a perspective side view of the posterior stabilizing trial attachment of FIG. 28A.

FIGS. 28A-D illustrate a posterior stabilizing trial attachment 600 that may be used with the femoral trial component 400 shown in FIGS. 24A-H to aid performance of one or more trial operations with the femoral trial component 400 in place on the distal end of the femoral bone. In particular, FIG. 28A is a perspective rear view of the posterior stabilizing trial attachment 600, FIG. 28B is another perspective rear view of the posterior stabilizing trial attachment 600, FIG. 28C is a perspective front view of the posterior stabilizing trial attachment 600, and FIG. 28D is a perspective side view of the posterior stabilizing trial attachment 600.

The posterior stabilizing trial attachment 600 may include a central portion articulation surface 610, an internal articulation surface 620 having a medial portion 622 and a lateral portion 624, a cam bar element 630 having a cam bar articulating surface 632, a posterior stabilizing box 670, and a gap 640 formed between the medial and lateral portions 622, 624 within the posterior stabilizing box 670. Each of these components of the posterior stabilizing trial attachment 600, such as the posterior stabilizing box 670 and the cam bar element 630, may be configured to allow for trialing of a complete posterior stabilizing femoral implant.

Figure 29A:
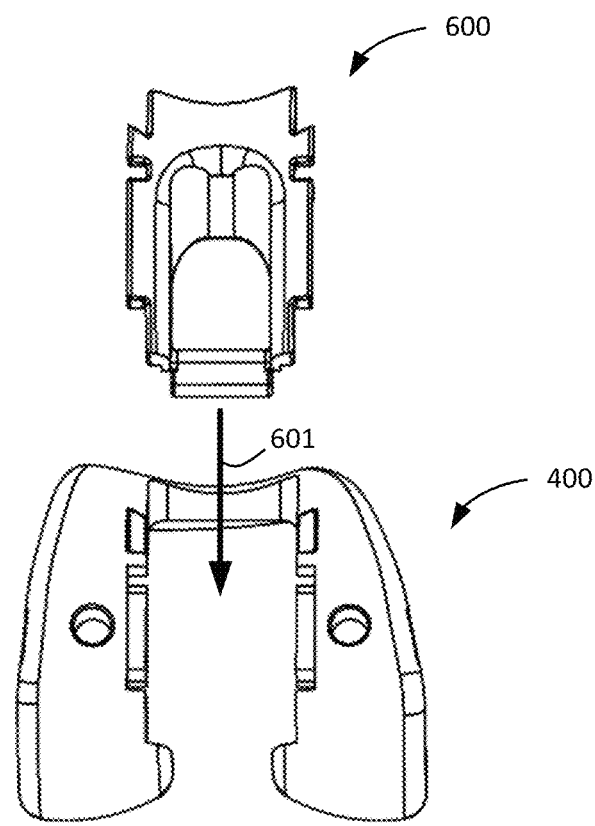
FIG. 29A is a posterior view of the posterior stabilizing trial attachment of FIG. 28A above the femoral trial component of FIG. 24A.
Figure 29B:
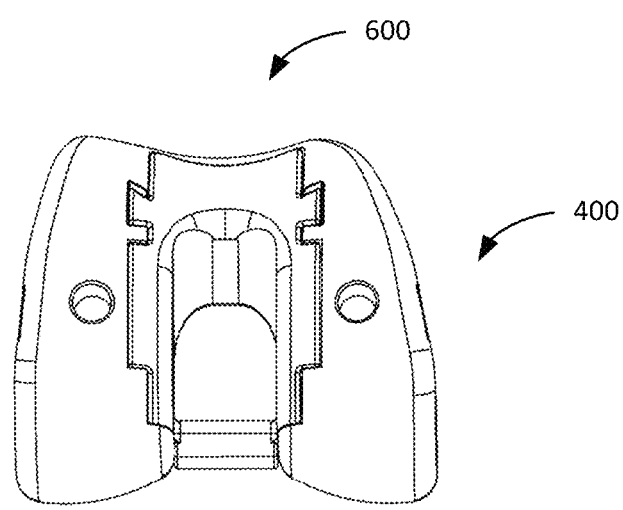
FIG. 29B is a posterior view of the posterior stabilizing trial attachment of FIG. 29A coupled to the femoral trial component of FIG. 29A.

The posterior stabilizing trial attachment 600 may also include attachment projections 650, 660 on the medial and lateral sides of the posterior stabilizing trial attachment 600. The attachment projections 650, 660 may have shapes that are complementary to the medial and lateral attachment features 450, 460 and/or the medial and lateral attachment recesses 456, 466 that are formed in the femoral trial component 400. In this manner, the attachment projections 650, 660 may be configured to couple to the medial and lateral attachment features 450, 460 and/or the medial and lateral attachment recesses 456, 466 formed in the femoral trial component 400, as shown in FIGS. 29A and 29B. This may be accomplished by holding the posterior stabilizing trial attachment 600 above the femoral trial component 400 and moving the posterior stabilizing trial attachment 600 toward the attachment aperture 440 formed in the universal femoral trial component 400 (see arrow 601 in FIG. 29A)

until the posterior stabilizing trial attachment 600 is coupled to the femoral trial component 400, as shown in FIG. 29B. In at least one embodiment, the posterior stabilizing trial attachment 600 may be further configured to magnetically couple to the femoral trial component 400.

In this manner, the posterior stabilizing trial attachment 600 may removably couple to the universal femoral trial component 400 and provide the central portion articulation surface 610 above the attachment aperture 440 of the femoral trial component 400 to allow for trialing of a complete articulation surface for a selected femoral implant type, such as a PS femoral component disclosed herein. A complete articulation surface may include a medial condylar articulation surface, a lateral condylar articulation surface, and the central portion articulation surface 610, for the selected femoral implant type.

Figure 30A:
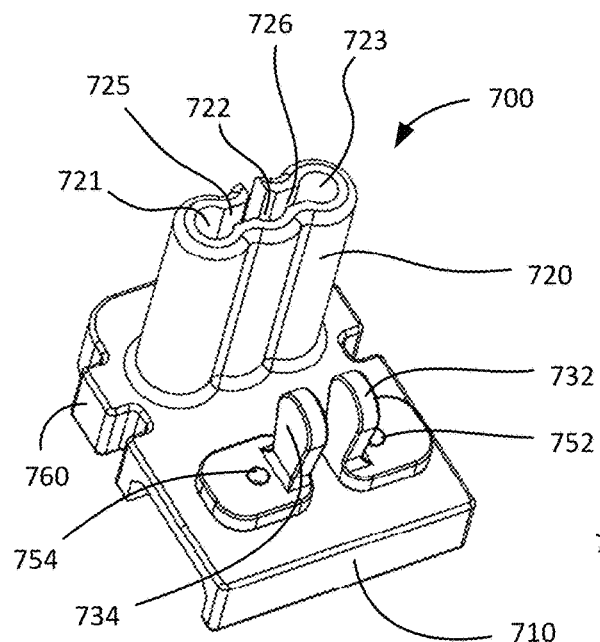
FIG. 30A is a perspective rear view of a drill and broach guide assembly of the disclosure.
Figure 30B:
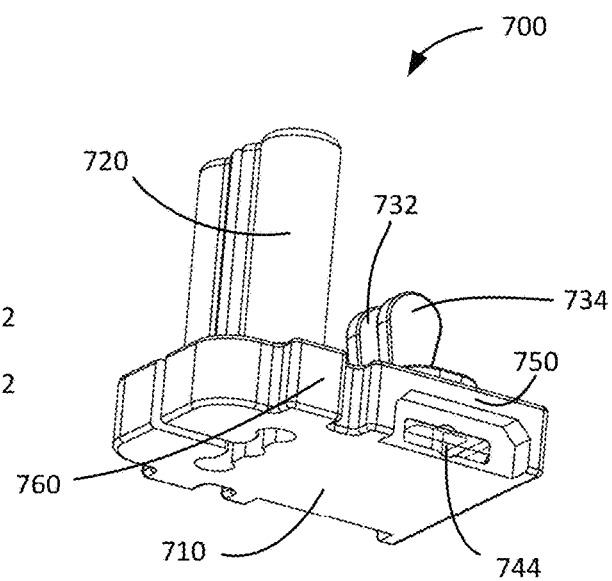
FIG. 30B is a perspective bottom view of the drill and broach guide assembly of FIG. 30A.
Figure 30C:
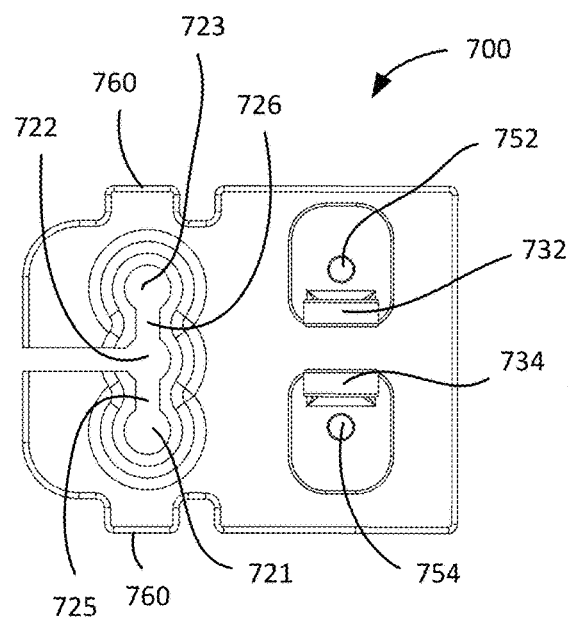
FIG. 30C is a top view of the drill and broach guide assembly of FIG. 30A.
Figure 30D:
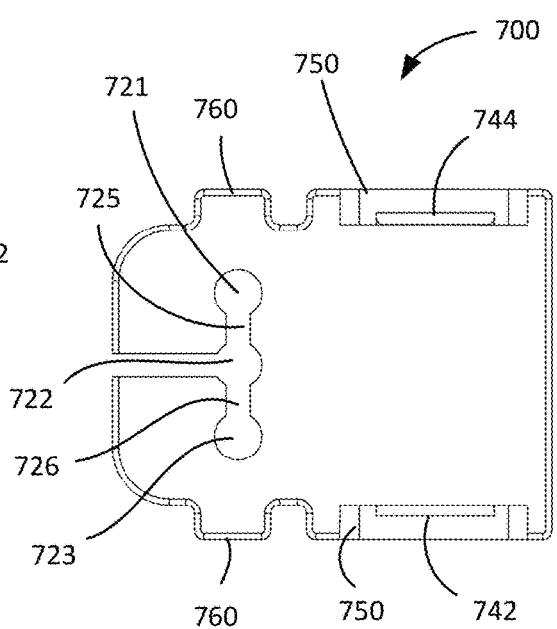
FIG. 30D is a bottom view of the drill and broach guide assembly of FIG. 30A.
Figure 31:
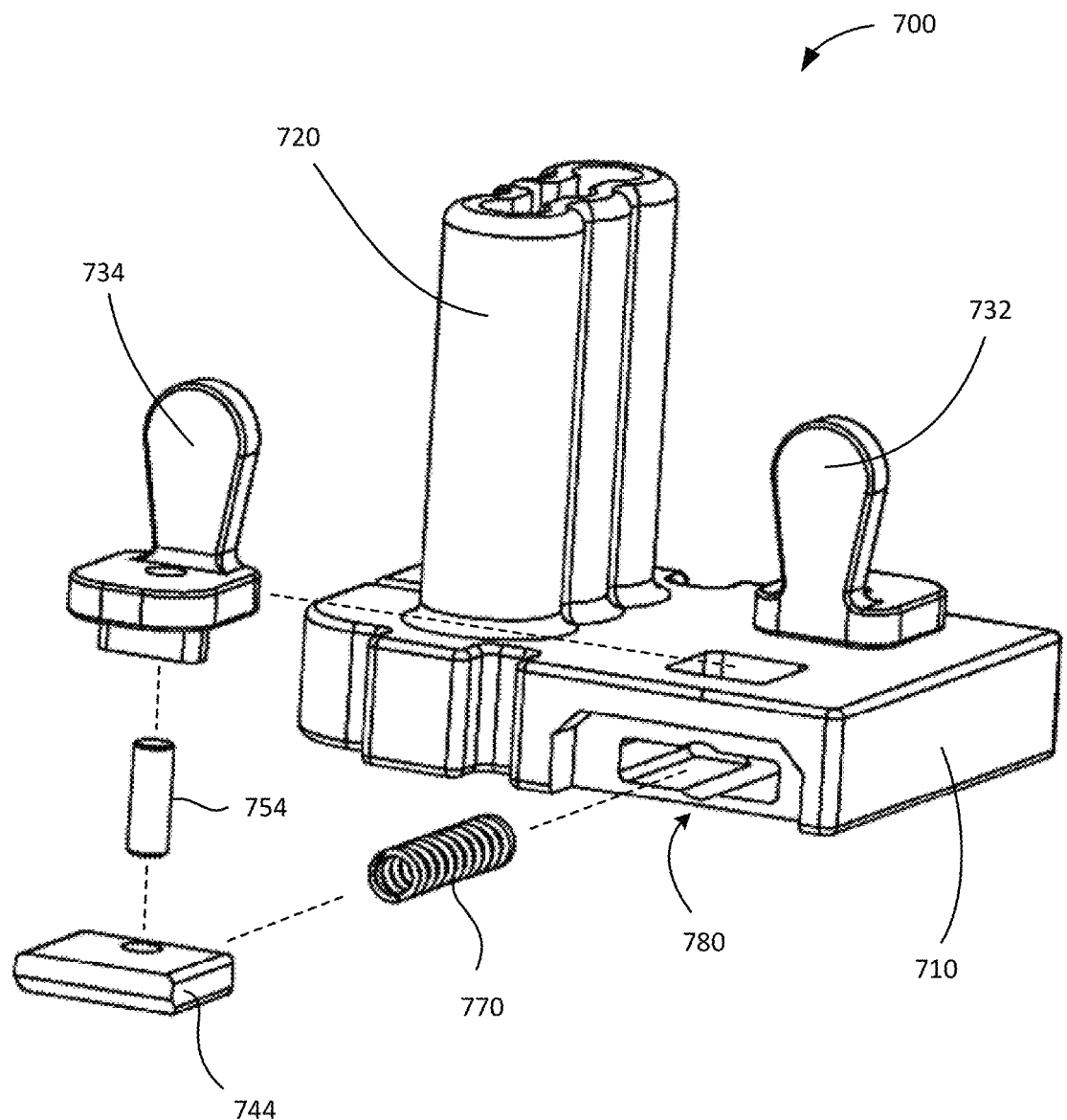
FIG. 31 is a partial exploded view of the drill and broach guide assembly of FIG. 30A.

FIGS. 30A-31 illustrate a drill and broach guide assembly 700 that may be used with the femoral trial component 400 shown in FIGS. 24A-H to help prepare a femur of a patient to receive a femoral component of the present disclosure that utilizes a keel or other bone fixation member that may require a pre-drilled and/or broached bone aperture. In particular, FIG. 30A is a perspective rear view of the drill and broach guide assembly 700, FIG. 30B is a perspective bottom view of the drill and broach guide assembly 700, FIG. 30C is a top view of the drill and broach guide assembly 700, FIG. 30D is a bottom view of the drill and broach guide assembly 700, and FIG. 31 is a partial exploded view of the drill and broach guide assembly 700.

The drill and broach guide assembly 700 may include a drill and broach guide body 710, attachment projections 750, 760, and a drill and broach guide 720. The drill and broach guide 720 may further include a first drill guide aperture 721, a second drill guide aperture 722, a third drill guide aperture 723, a first broach guide aperture 725 intermediate the first drill guide aperture 721 and the second drill guide aperture 722, and a second broach guide aperture 726 intermediate the second drill guide aperture 722 and the third drill guide aperture 723. The second drill guide aperture 722 may also be located intermediate the first broach guide aperture 725 and the second broach guide aperture 726.

The drill and broach guide assembly 700 may also include a drill and broach guide locking mechanism which may include: a first locking member 742, a second locking member 744, a first release lever 732 coupled to the first locking member 742 via a first pin 752, a second release lever 734 coupled to the second locking member 744 via a second pin 754, and a resilient member 770 located between the first locking member 742 and the second locking member 744 within a locking member housing 780 formed within the drill and broach guide body 710. The resilient member 770 may be configured to apply a biasing force between the first locking member 742 and the second locking member 744 to push the first locking member 742 and the second locking member 744 away from each other.

Figure 32A:
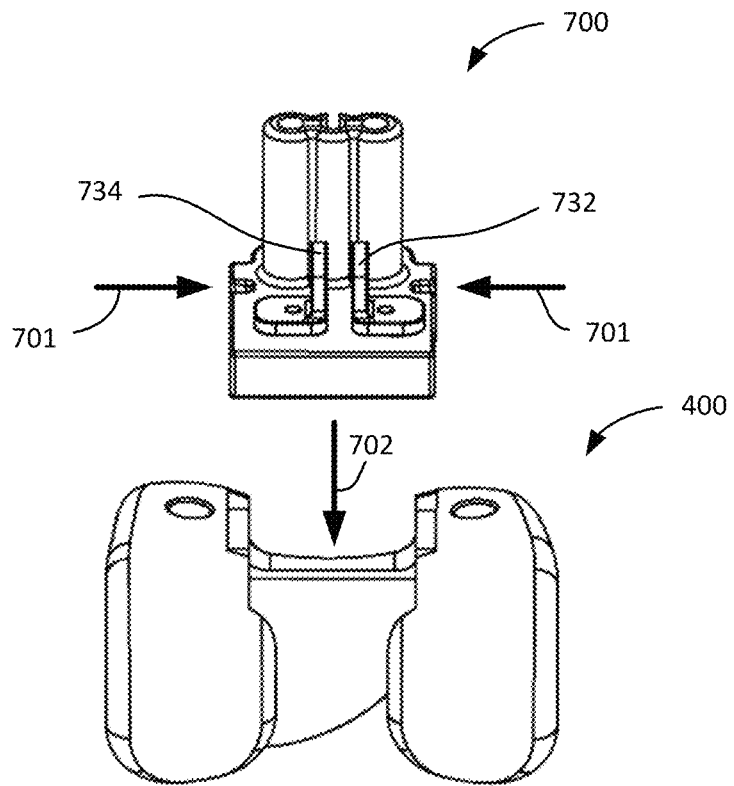
FIG. 32A is a posterior view of the drill and broach guide assembly of FIG. 30A above the femoral trial component of FIG. 24A.
Figure 32B:
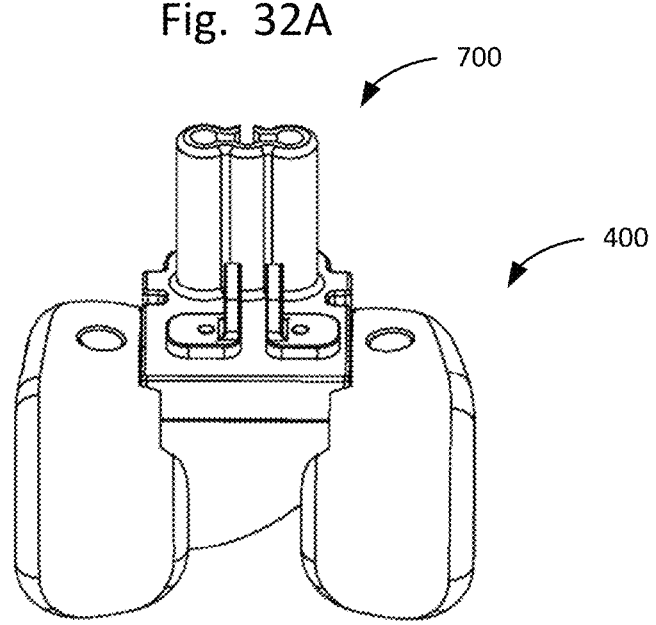
FIG. 32B is a posterior view of the drill and broach guide assembly of FIG. 32A coupled to the femoral trial component of FIG. 32A.

Referring to FIGS. 32A and 32B, the drill and broach guide assembly 700 may be removably coupled to the universal femoral trial component 400 by squeezing the first release lever 732, and the second release lever 734 together toward each other (see arrows 701 in FIG. 32A) in order to overcome the biasing force of the resilient member 770 between the first locking member 742 and the second locking member 744; then inserting the drill and broach guide assembly 700 into the attachment aperture 440 formed in the universal femoral trial component 400 (see arrow 702 in FIG. 32A); and finally releasing the first release lever 732 and the second release lever 734 to allow the biasing force of the resilient member 770 to push the first locking member 742 and the second locking member 744 away from each other, causing the first locking member 742 to enter within the medial attachment aperture 454 of the femoral trial component 400 and the second locking member 744 to enter within the lateral attachment aperture 464 of the femoral trial component 400 to couple the drill and broach guide assembly 700 to the universal femoral trial component 400, as shown in FIG. 32B. The attachment projections 750, 760 may also have shapes that are complementary to the medial and lateral attachment features 450, 460 and/or the medial and lateral attachment recesses 456, 466 formed in the femoral trial component 400 to aid coupling of the drill and broach guide assembly 700 to the universal femoral trial component 400, as well as magnetic coupling capabilities.

Figure 40:
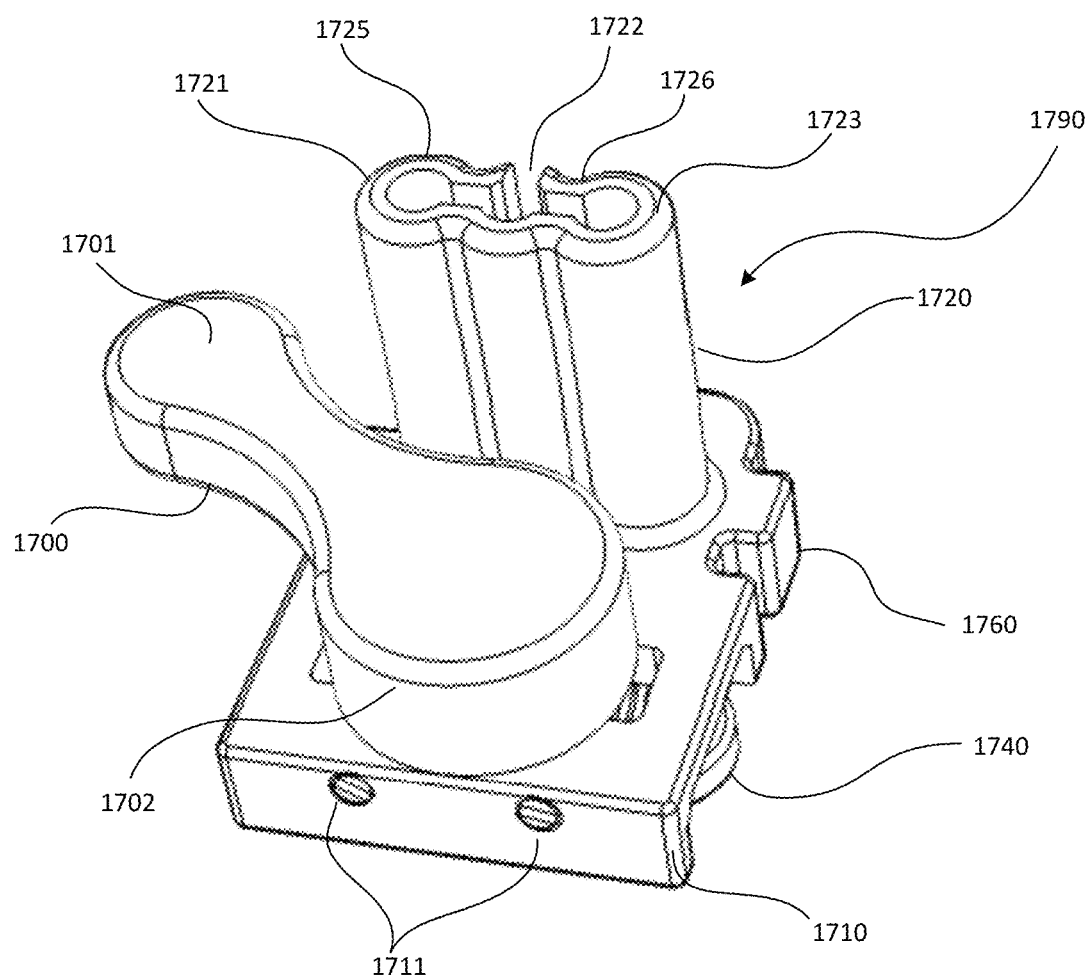
FIG. 40 is a perspective rear view of an embodiment of a drill and broach guide assembly of the disclosure.
Figure 41:
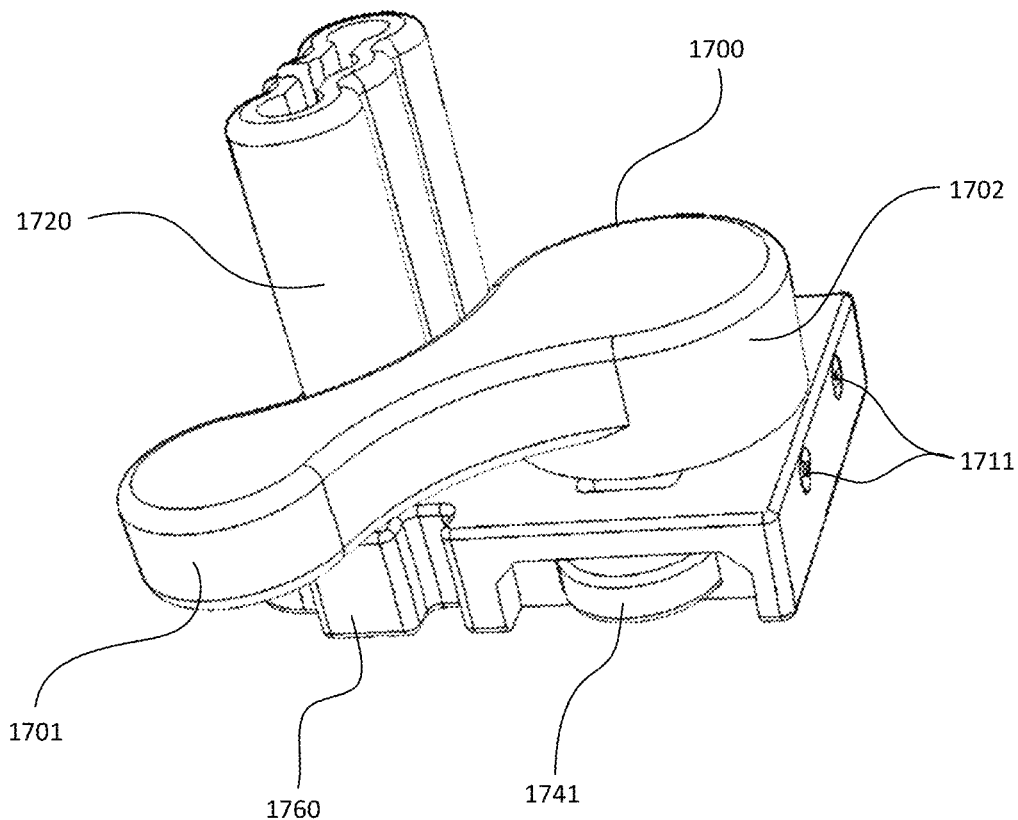
FIG. 41 is a side perspective view of the drill and broach guide assembly of FIG. 40.
Figure 42:
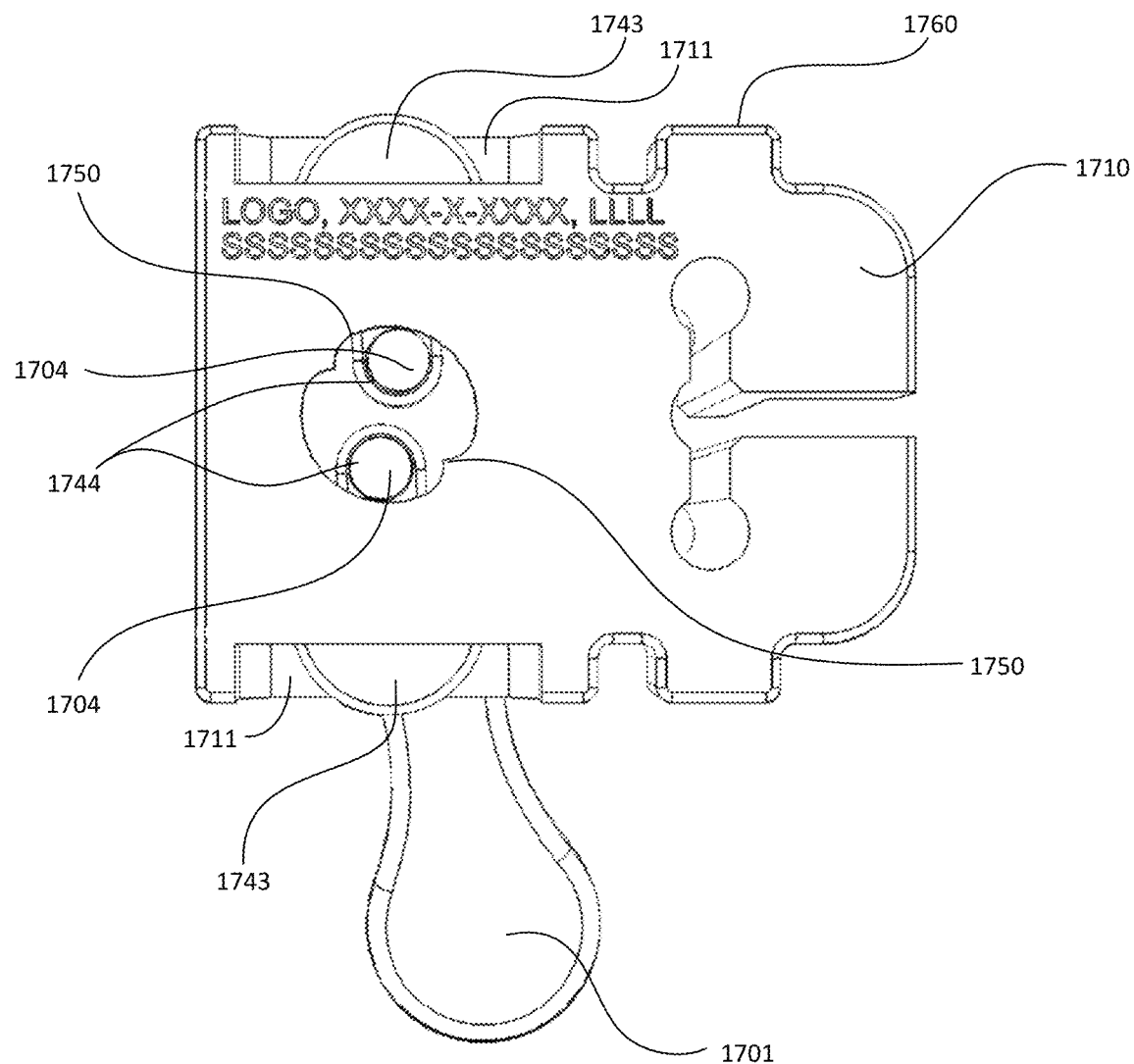
FIG. 42 is a bottom view of the drill and broach guide assembly of FIG. 40.
Figure 43:
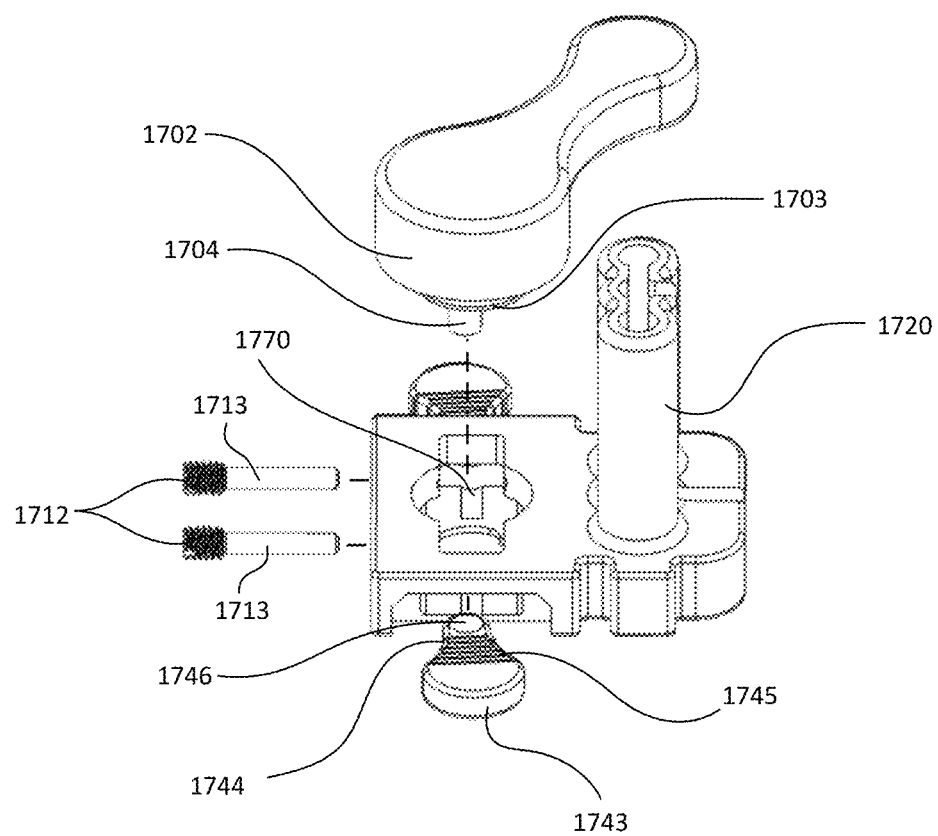
FIG. 43 is a partial exploded view of the drill and broach guide assembly of FIG. 40.
Figure 44:
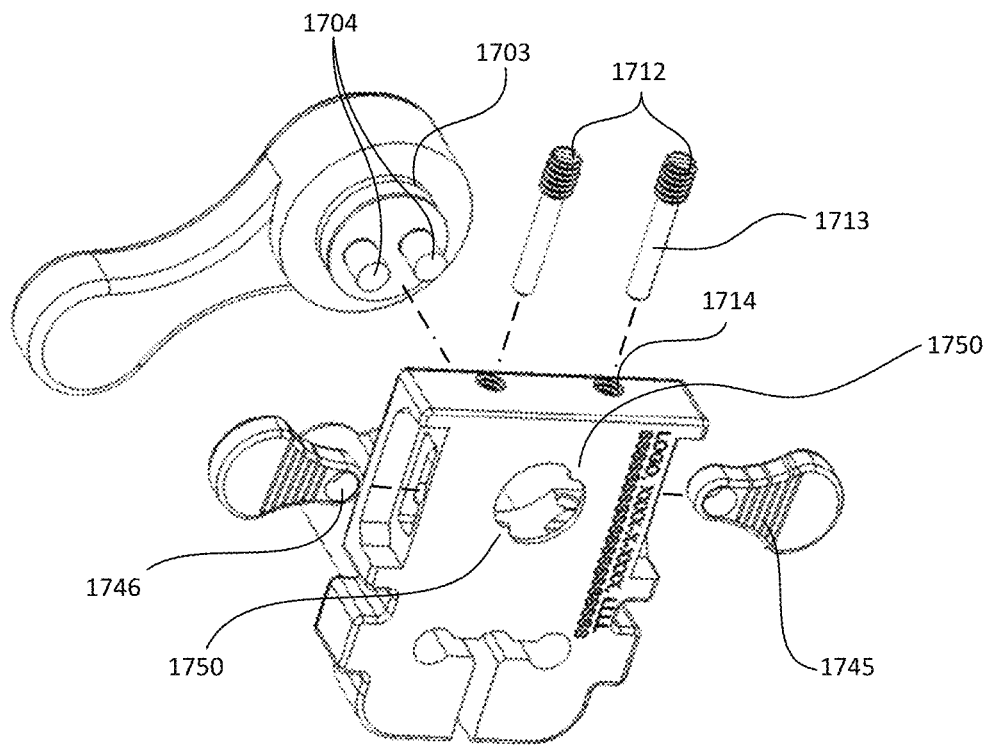
FIG. 44 is a partial exploded bottom perspective view of the drill and broach guide assembly of FIG. 40.

FIGS. 40-44 illustrate an embodiment of a drill and broach guide assembly 1790 that may be used with the femoral trial component 400 shown in FIGS. 24A-H to help prepare a femur of a patient to receive a femoral component of the present disclosure that utilizes a keep or other bone fixation member, which may require a pre-drilled and/or broached bone aperture. In particular, FIG. 40 is a perspective view of the drill and broach guide assembly 1790, FIG. 41 is a side perspective view of the drill and broach guide assembly 1790, FIG. 42 is a bottom view of the drill and broach guide assembly 1790, FIG. 43 is a partial exploded view of the drill and broach guide assembly 1790, and FIG. 44 is a partial exploded bottom perspective of the drill and broach guide assembly 1790.

The drill and broach guide assembly 1790 may include a drill and broach guide body 1710, attachment projections 1760 on opposing sides of the body 1710, and a drill and broach guide 1720. The drill and broach guide 1720 may further include a first drill guide aperture 1721, a second drill guide aperture 1722, a third drill guide aperture 1723, a first broach guide aperture 1725 intermediate the first drill guide aperture 1721 and the second drill guide aperture 1722, and a second broach guide aperture 1726 intermediate the second drill guide aperture 1722 and the third drill guide aperture 1723. The second drill guide aperture 1722 may also be located intermediate the first broach guide aperture 1725 and the second broach guide aperture 1726.

The drill and broach guide assembly 1790 may also include a drill and broach guide locking mechanism. The locking mechanism may include a handle 1700, with a grip 1701, a base 1702, a track 1703, and a handle tab connection 1704. The handle 1700 fits within a cavity 1770 in the body 1710 of the drill and broach guide, so that the handle tab connections pass into the cavity 1770 and the base 1702 may rest on the body 1710. The handle is attached to the body 1710 via pins 1711. The handle is operationally connected to a first tab 1740 and a second tab 1741. The first tab 1740 and the second tab 1741 are extendable from the base 1710 on opposing sides, as illustrated in FIGS. 40 and 41.

As illustrated in FIG. 42, the handle tab connection 1704 is visible in the cavity 1770, in a bottom of the base 1710. The handle tab connection 1704 is shown as two protrusions from the base 1702 of the handle 1700, which engage tab apertures 1746 in the first tab 1740 and the second tab 1741. However, it is understood that the handle tab connection 1704 may be any reasonable operational connection between the handle 1700 and the first tab 1740 and the second tab 1741. Other operational connections may include protrusions on the first tab 1740 and the second tab 1741, which engage with apertures on the handle 1700. Operational connections may include belt or screw drives, or any combination of bosses, bushings, or other bearing surfaces. The handle tab connection 1704 engages and passes through proximal ends 1744 of the first tab 1740 and the second tab 1741. A portion of the handle tab connections 1704, passing through and protruding through the proximal ends 1744 of the first tab 1740 and the second tab 1741, may engage rotation stops 1750 on the body 1710 at the edge of the cavity 1770. The rotation stops 1750 oppose one another across the cavity 1770, and are configured to limit the movement of the handle tab connection 1704 about an axis that passes through the cavity 1770. The rotation stops 1750 are illustrated as bumps or protrusions but may have any structural configuration that limits movement of the handle 1700 about the axis.

The first tab 1740 and the second tab 1741 each have a proximal end 1744, which is engaged with the handle 1700 as discussed above, a distal end 1743, and a compressible section 1745 connecting the proximal end 1744 and the distal end 1743. The first tab 1740 and the second tab 1741 are located within the body 1710 of the guide assembly 1790, so that the proximal ends 1744 are nearest the cavity 1770 and the distal ends 1743 extend away from the cavity 1770, as shown in FIG. 42. The compressible sections 1745 are depicted having spring-like configurations, but may have coiled or other resilient configurations.

FIGS. 43 and 44 illustrate more fully how the drill and broach guide 1790 is operationally connected. The handle 1700 may rotate relative to the body 1710 about the axis that passes through the cavity 1770. The handle 1700 is secured to the body 1710 via an engagement between pins 1711, the body 1710, and the track 1703 of the handle 1700. The pins 1711 each comprise a threaded section 1712 and a smooth section 1713. The pins 1711 are configured to screw into pin holes 1714 in the body 1710. The threaded sections 1712 engage with complementary threaded portions of the pin holes 1714. When threaded in the pin holes 1744, the smooth sections 1713 of the pins 1711 extend into the cavity 1770. When the base 1702 of the handle 1700 is seated on the body 1710, the track 1703 extends into the cavity 1770 and engages the smooth sections 1713 of the pins 1711. The track 1703 and the smooth sections 1713 have complementary profiles, for example the track 1703 is concave and the smooth sections 1713 are convex, which rest in the track 1703. The smooth sections 1713 engage with opposite sides of the track, which fixes the handle 1700 to the body 1710, yet allows the handle 1700 to rotate about the axis.

The rotation of the handle 1700, while operationally secured to the body 1710, creates a camming action causing the first tab 1740 and the second tab 1741 to extend from or retract into corresponding tab recesses 1771 in opposing sides of the body 1710. As the handle 1710 is turned, the handle tab connections 1704 act on the proximal ends 1744 of the first tab 1740 and second tab 1741 pushing the tabs 1740 1741 out of the body 1710. The protruding portions of the handle tab connections 1704 abut the rotation stops 1750 preventing the handle from a complete rotation. The drill and broach guide assembly 1790 may be configured so that the handle tab connections 1704 abut the rotation stops 1750 when the first tab 1740 and the second tab 1741 are at a most-extended position, away from the body. The compressible section 1745 of the first tab 1740 and the second tab 1741 may be configured to apply a biasing force between the distal ends 1743 and the proximal ends 1744 ends of each of the tabs 1740 1741 and the handle 1700.

In operation, the drill and broach guide assembly 1790 may be removably coupled to the universal femoral trial component 400 by inserting the drill and broach guide assembly 1790 into the attachment aperture 440 formed in the universal femoral trial component 400, similar to what is shown in FIG. 32A represented by arrow 702. The attachment projections 1760 may also have shapes that are complementary to the medial and lateral attachment features 450, 460 and/or the medial and lateral attachment recesses 456, 466 formed in the femoral trial component 400 to aid coupling of the drill and broach guide assembly 1790 to the universal femoral trial component 400, as well as magnetic coupling capabilities. Once seated in the trial component, the handle 1700 may be rotated so that the first tab 1740 and the second tab 1741 are extended into the medial attachment aperture 454 and the lateral attachment aperture 464 of the femoral trial component 400. As the tab distal ends 1743 abut walls of the attachment apertures 454 464, the compressible sections 1745 begin to compress, creating the biasing force discussed above. The handle 1700 may be turned further so that the handle tab connections 1704 abut the rotation stops 1750. The combination of the biasing force from the compressible sections 1745 in the medial attachment aperture 464 and the lateral attachment aperture 465 and the abutment of the handle tab connections against the rotation stops 1750, causes the drill and broach guide assembly to lock in place in the femoral trial component.

Figure 33A:
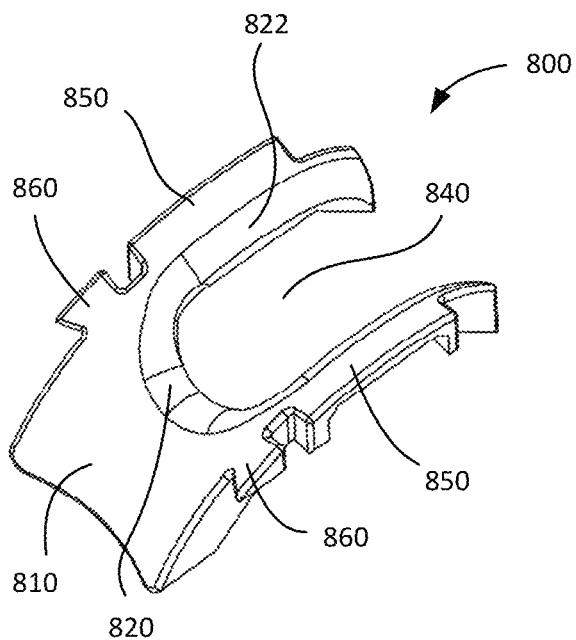
FIG. 33A is a perspective front view of a cruciate retaining trial attachment of the disclosure.
Figure 33B:
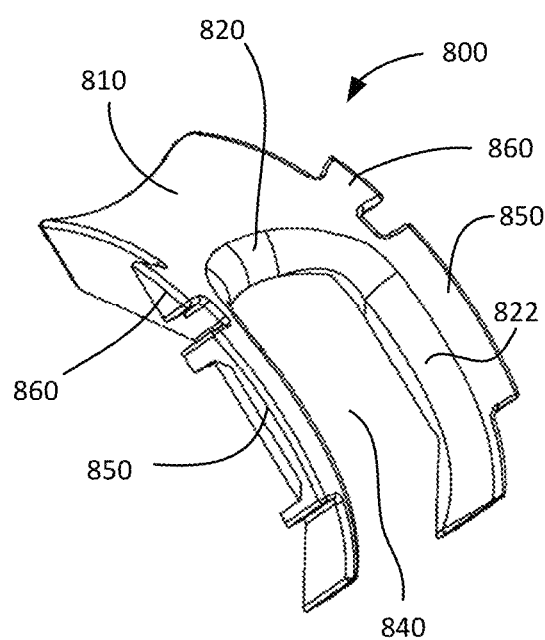
FIG. 33B is a perspective rear view of the cruciate retaining trial attachment of FIG. 33A.
Figure 33C:
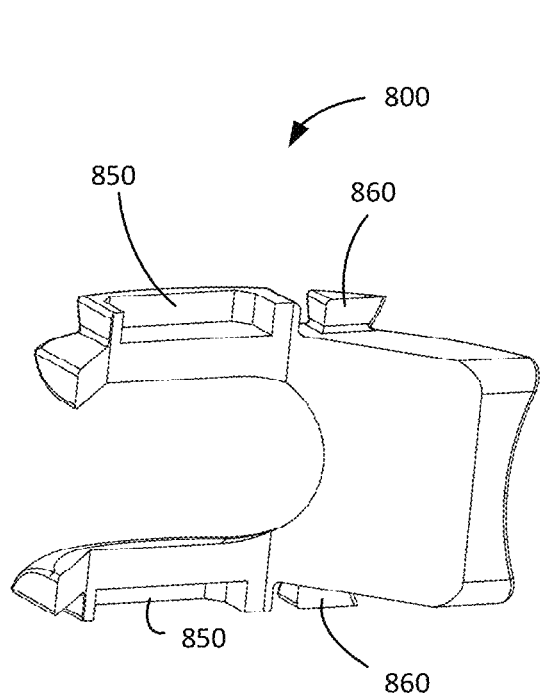
FIG. 33C is a perspective bottom view of the cruciate retaining trial attachment of FIG. 33A.
Figure 33D:
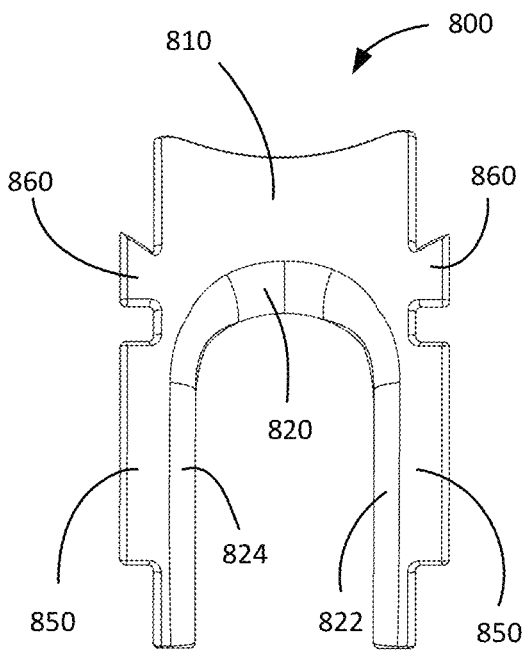
FIG. 33D is a top view of the cruciate retaining trial attachment of FIG. 33A.

FIGS. 33A-D illustrate a cruciate retaining trial attachment 800 that may be used with the femoral trial component 400 shown in FIGS. 24A-H to aid performance of one or more trial operations with the femoral trial component 400 in place on the distal end of the femoral bone. In particular, FIG. 33A is a perspective front view of the cruciate retaining trial attachment 800, FIG. 33B is a perspective rear view of the cruciate retaining trial attachment 800, FIG. 33C is a perspective bottom view of the cruciate retaining trial attachment 800, and FIG. 33D is a top view of the cruciate retaining trial attachment 800.

The cruciate retaining trial attachment 800 may include a central portion articulation surface 810, an internal articulation surface 820 having a medial portion 822 and a lateral portion 824, and a gap 840 formed between the medial and lateral portions 822, 824. Each of these components of the cruciate retaining trial attachment 800 may be configured to allow for trialing of a complete cruciate retaining femoral implant.

Figure 34A:
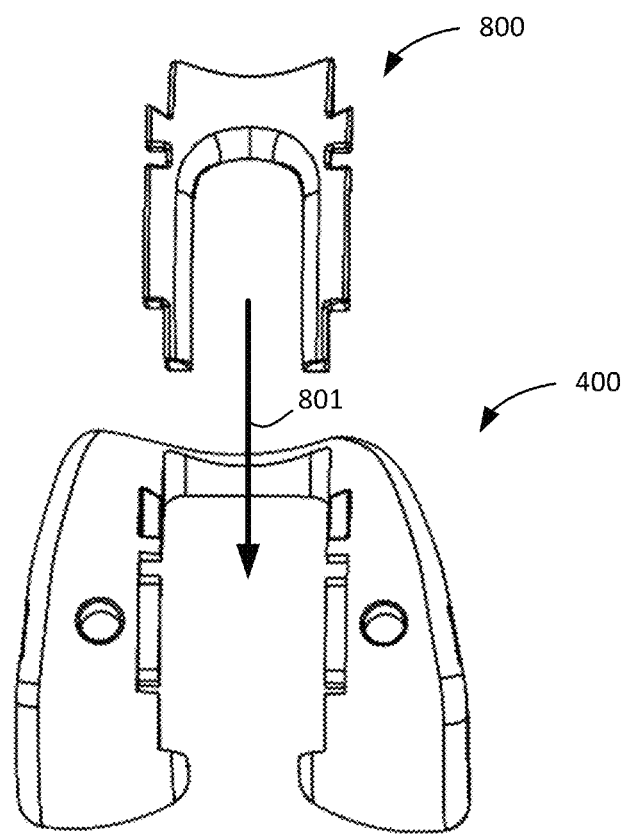
FIG. 34A is a posterior view of the cruciate retaining trial attachment of FIG. 33A above the femoral trial component of FIG. 24A.
Figure 34B:
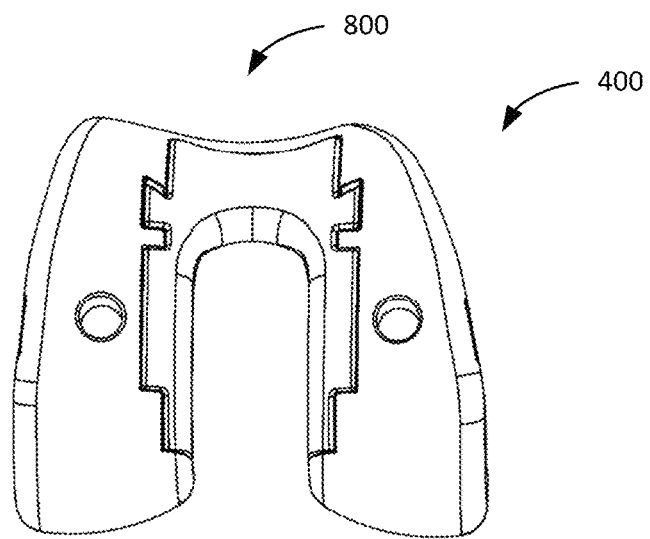
FIG. 34B is a posterior view of the cruciate retaining trial attachment of FIG. 34A coupled to the femoral trial component of FIG. 34A.

The cruciate retaining trial attachment 800 may also include attachment projections 850, 860 on the medial and lateral sides of the cruciate retaining trial attachment 800. The attachment projections 850, 860 may have shapes that are complementary to the medial and lateral attachment features 450, 460 and/or the medial and lateral attachment recesses 456, 466 that are formed in the femoral trial component 400. In this manner, the attachment projections 850, 860 may be configured to couple to the medial and lateral attachment features 450, 460 and/or the medial and lateral attachment recesses 456, 466 formed in the femoral trial component 400, as shown in FIGS. 34A and 34B. This may be accomplished by holding the cruciate retaining trial attachment 800 above the femoral trial component 400 and moving the cruciate retaining trial attachment 800 toward the attachment aperture 440 formed in the universal femoral trial component 400 (see arrow 801 in FIG. 34A) until the cruciate retaining trial attachment 800 is coupled to the femoral trial component 400, as shown in FIG. 34B. In at least one embodiment, the cruciate retaining trial attachment 800 may be further configured to magnetically couple to the femoral trial component 400.

In this manner, the cruciate retaining trial attachment 800 may removably couple to the universal femoral trial component 400 and provide the central portion articulation surface 810 above the attachment aperture 440 of the femoral trial component 400 to allow for trialing of a complete articulation surface for a selected femoral implant type, such as a CR femoral component disclosed herein. A complete articulation surface may include a medial condylar articulation surface, a lateral condylar articulation surface, and the central portion articulation surface 810, for the selected femoral implant type.

Any of the components disclosed herein may be included in a modular universal femoral trial kit (not shown) to aid in preparing and trialing a femoral bone of a patient to receive a plurality of different femoral implant types. In at least one embodiment, the modular universal femoral trial kit may include a container (not shown) that contains a femoral trial component 400, 900 and at least one femoral bone preparation attachment, such as the posterior stabilizing notch cutting guide assembly 500 and/or the drill and broach guide assembly 700, as one non-limiting example. In other embodiments, the modular universal femoral trial kit may also include at least one femoral trial attachment, such as the cruciate retaining trial attachment 800 and/or the posterior stabilizing trial attachment 600, as another non-limiting example.

Figure 36:
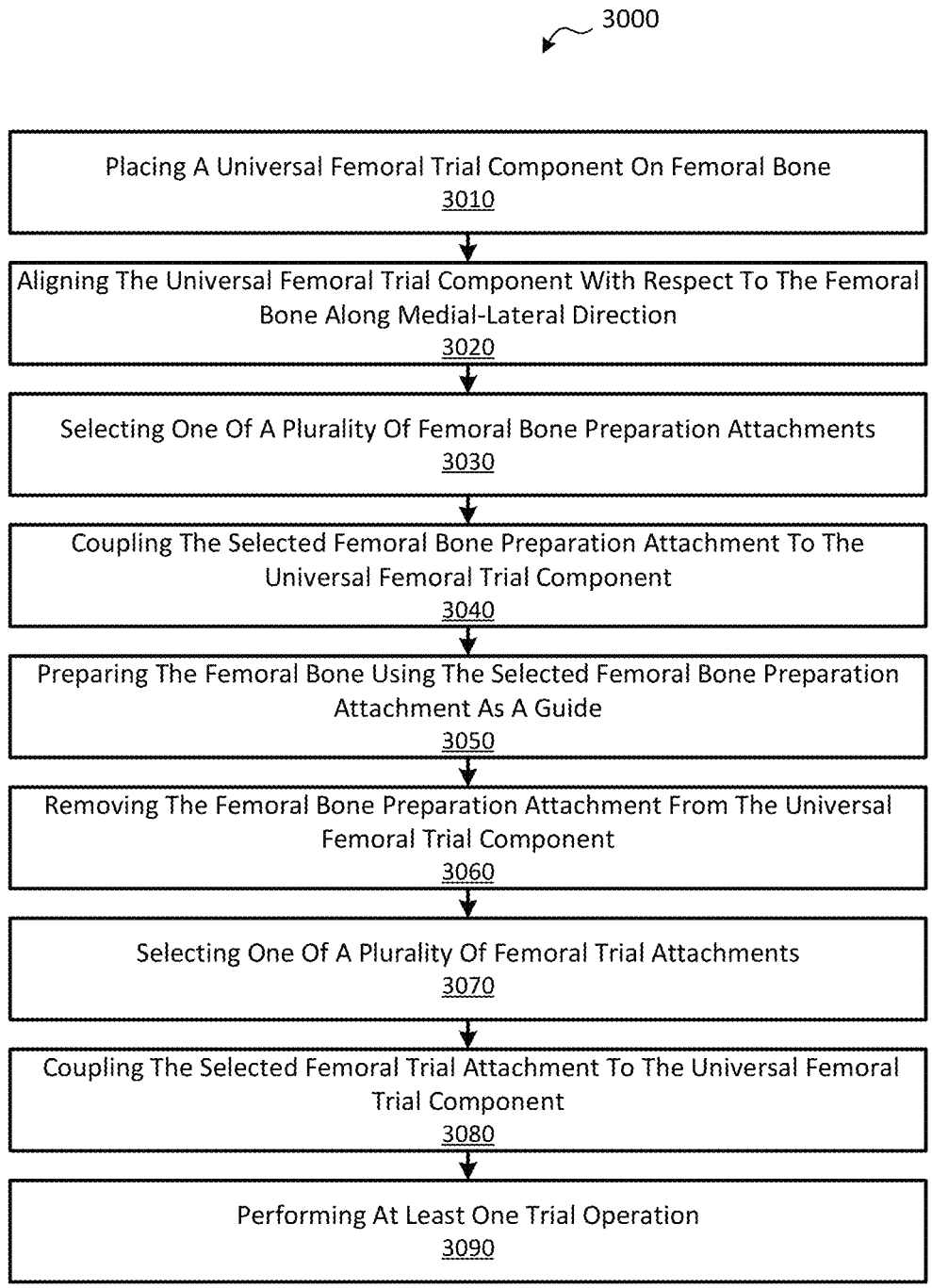
FIG. 36 is a flow chart diagram of a method for preparing and trialing a femoral bone with a femoral trial component.

FIG. 36 illustrates a flow chart diagram of a method 3000 for preparing and trialing a femoral bone with a universal femoral trial component 400, 900, according to one embodiment of the present disclosure. The method 3000 will be described in connection with the components and instrumentation described herein. However, those of skill in the art will recognize that alternative implants, assemblies, systems, and instrumentation may be used in the performance of the method 3000.

The method 3000 may begin with a step 3010 in which a universal femoral trial component 400, 900 may be placed on an inferior or distal end of a femoral bone. The distal end of the femoral bone may first be partially prepared with five distal cuts that are made to the distal end of the femur using standard techniques and tools (not shown) that are well known in the art. These five cuts may be made to correspond in both shape and angle to the five surfaces on the inner portion of the universal femoral trial component 400, 900 (e.g., see FIGS. 24C and 24D). The universal femoral trial component 400, 900 may then be press fit onto the partially prepared distal end of the femur.

In a step 3020, the universal femoral trial component 400, 900 may be further aligned with respect to the femoral bone along a medial-lateral direction in order to place the universal femoral trial component 400, 900 at a desired medial-lateral location with respect to the femoral bone.

In a step 3030, one of a plurality of femoral bone preparation attachments may be selected in order to guide resection of portions of the femoral bone, as desired. Example, femoral bone preparation attachments may include the posterior stabilizing notch cutting guide assembly 500 and the drill and broach guide assembly 700, as two non-limiting examples.

In a step 3040, the selected femoral bone preparation attachment may be coupled to the universal femoral trial component 400, 900 using techniques described previously herein (e.g., see description related to FIGS. 27A-B and FIGS. 32A-B).

In a step 3050, the femoral bone may be prepared to receive a desired femoral component by using the selected femoral bone preparation attachment as a guide to resect at least a portion of the femoral bone in order to prepare the femoral bone to receive the desired femoral component.

Once the femoral bone has been prepared with the selected femoral bone preparation attachment, the method may move to a step 3060.

In the step 3060, the selected femoral bone preparation attachment may be removed from the universal femoral trial component 400, 900.

In a step 3070, one of a plurality of femoral trial attachments may be selected in preparation for performing one or more trial operations with the universal femoral trial component 400, 900 still in place on the femoral bone.

In a step 3080, the selected femoral trial attachment may be coupled to the universal femoral trial component 400, 900 using techniques described previously herein (e.g., see description related to FIGS. 29A-B and FIGS. 34A-B).

In a step 3090, at least one trial operation may be performed with the selected femoral trial attachment coupled to the universal femoral trial component 400, 900, and the method 300 may end. For example, the surgeon may perform trialing of articulation surfaces of the knee joint to ensure that the articulation characteristics of the prosthetic knee joint will be satisfactory.

Various steps of any method disclosed herein may be reordered, omitted, and/or replaced with different steps within the scope of the present disclosure. Those of skill in the art, with the aid of the present disclosure, will recognize that many variations may be made to any other method disclosed herein, depending on the particular surgical procedure to be carried out, as well as the configuration of the system used in the performance of that surgical procedure. Moreover, any methods disclosed herein may include one or more steps or actions for performing the described method. These method steps and/or actions may be interchanged with one another. In other words, unless a specific order of steps or actions is required for proper operation of the embodiment, the order and/or use of specific steps and/or actions may be modified.

FIG. 37 illustrates a flow chart diagram of a method 4000 for revising a knee joint prosthesis implanted in a knee of a patient to provide increased stability to the knee joint prosthesis, according to one embodiment of the present disclosure. The method 4000 will be described in connection with the components and instrumentation described herein. However, those of skill in the art will recognize that alternative implants, assemblies, systems, and instrumentation may also be used in the performance of the method 4000.

The method 4000 may begin with a step 4010, in which a first knee joint prosthesis that is implanted in a knee of a patient is surgically accessed. The first knee joint prosthesis may comprise a first tibial insert that is located between a tibial base plate component that is implanted on a tibia of the patient and a femoral component that is implanted on a femur of the patient.

The method 4000 may then proceed to a step 4020, in which the first tibial insert may be removed from between the tibial base plate component and the femoral component.

The method 4000 may then proceed to a step 4030, in which a second tibial insert may be inserted between the tibial baseplate component and the femoral component to create a second knee joint prosthesis assembly that is more constrained that the first knee joint prosthesis assembly, and the method 4000 may end.

Figure 38A:
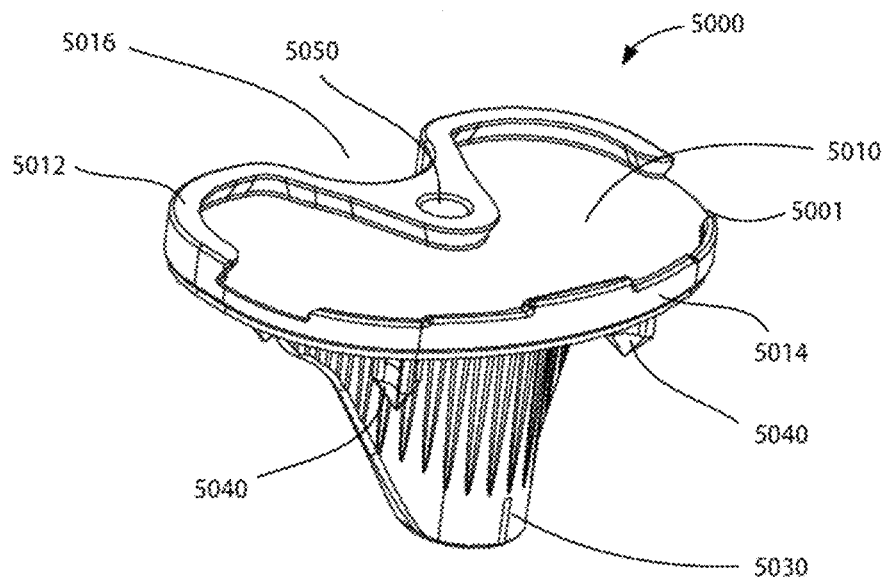
FIG. 38A is a perspective front view of a tibial tray of the disclosure.
Figure 38B:
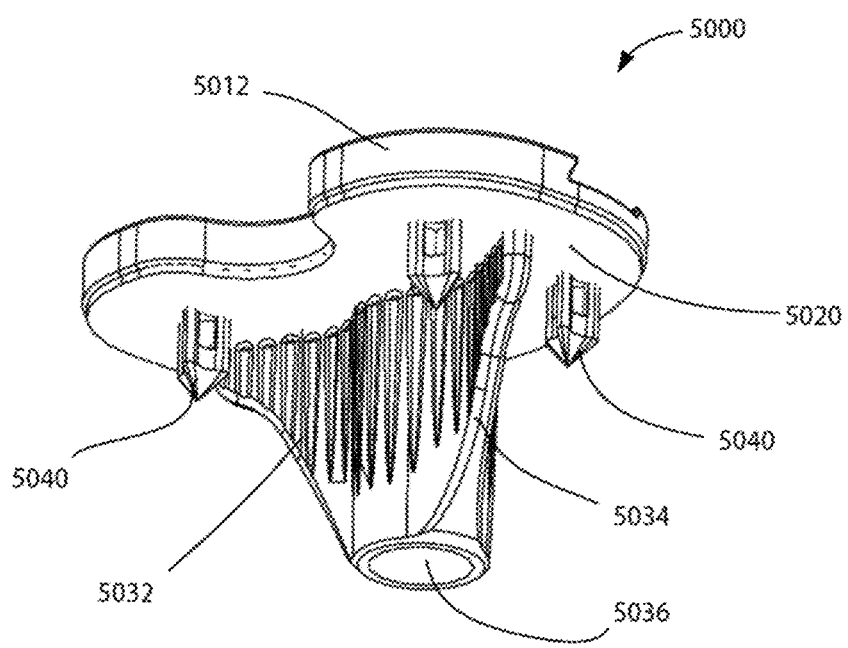
FIG. 38B is a perspective rear view of the tibial tray of FIG. 38A.
Figure 38C:
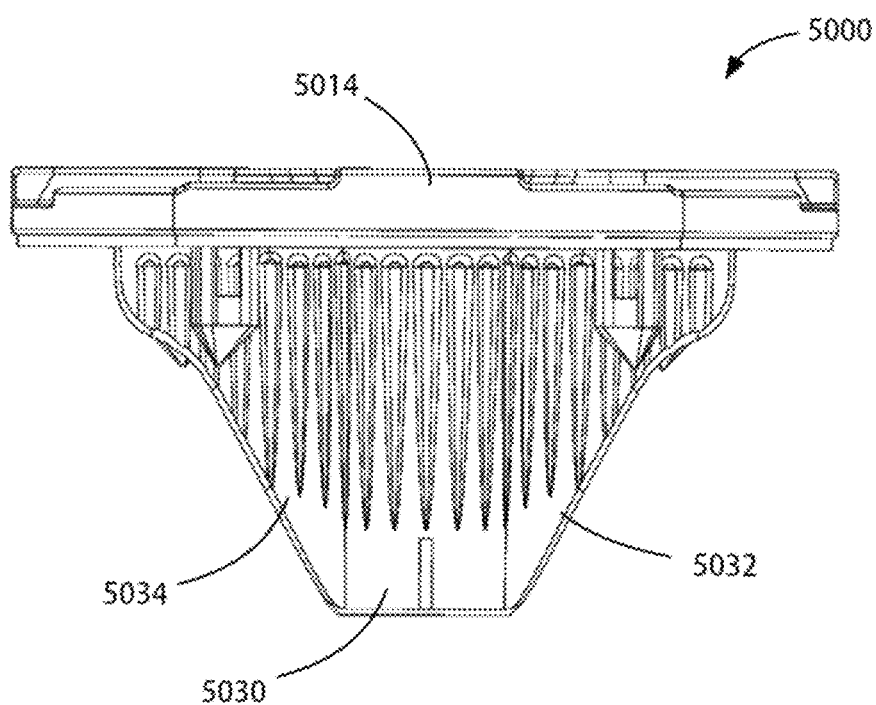
FIG. 38C is an anterior view of the tibial tray of FIG. 38A.
Figure 38D:
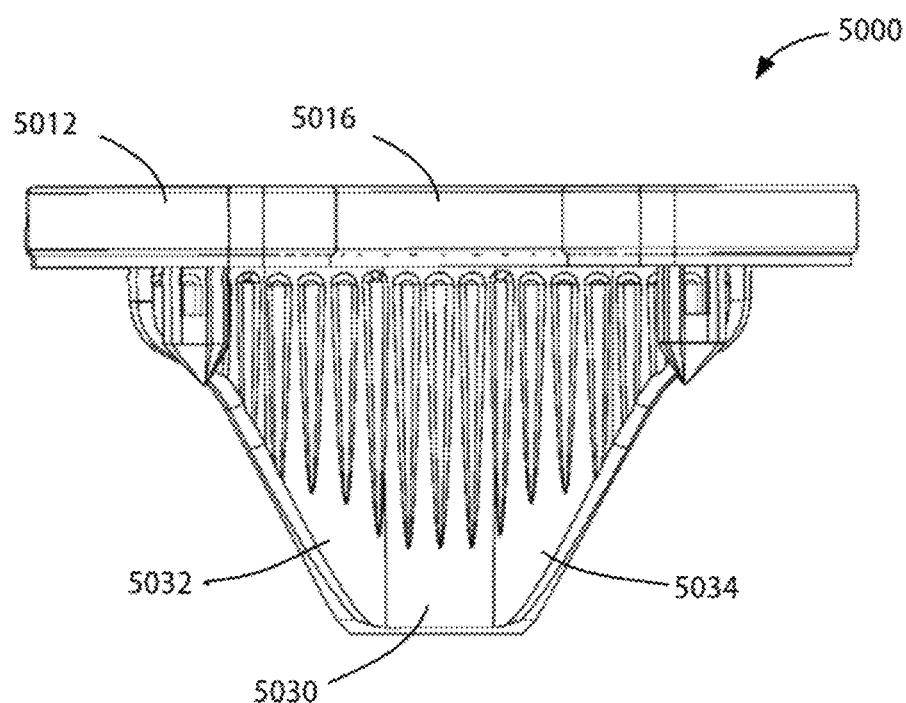
FIG. 38D is a posterior view of the tibial tray of FIG. 38A.
Figure 38E:
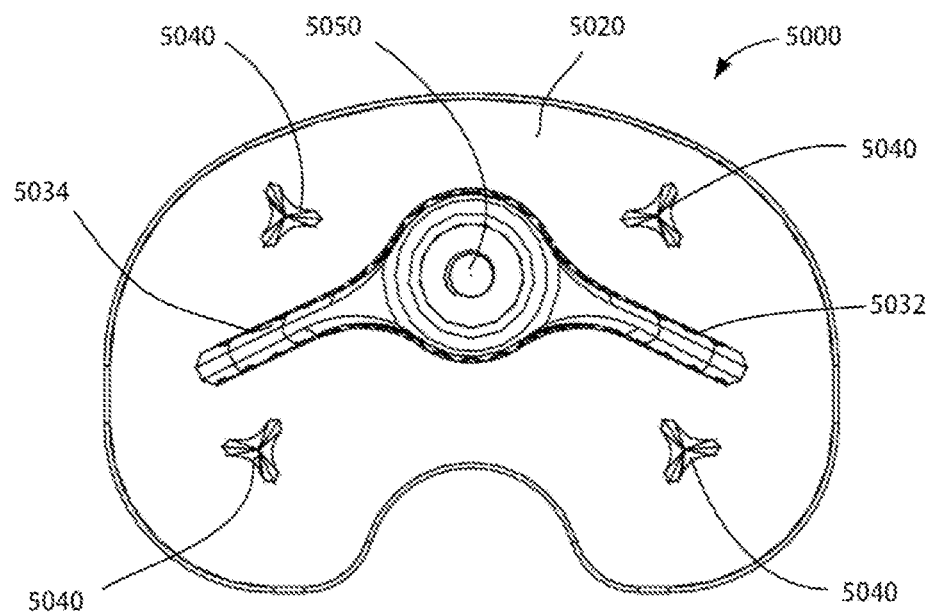
FIG. 38E is a bottom view of the tibial tray of FIG. 38A.
Figure 38F:
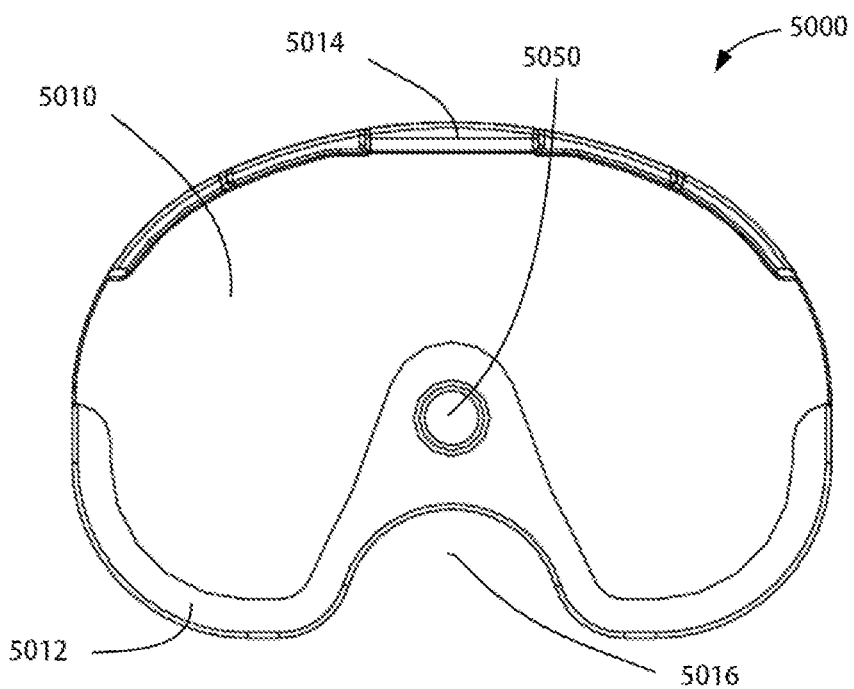
FIG. 38F is a top view of the tibial tray of FIG. 38A.
Figure 39:
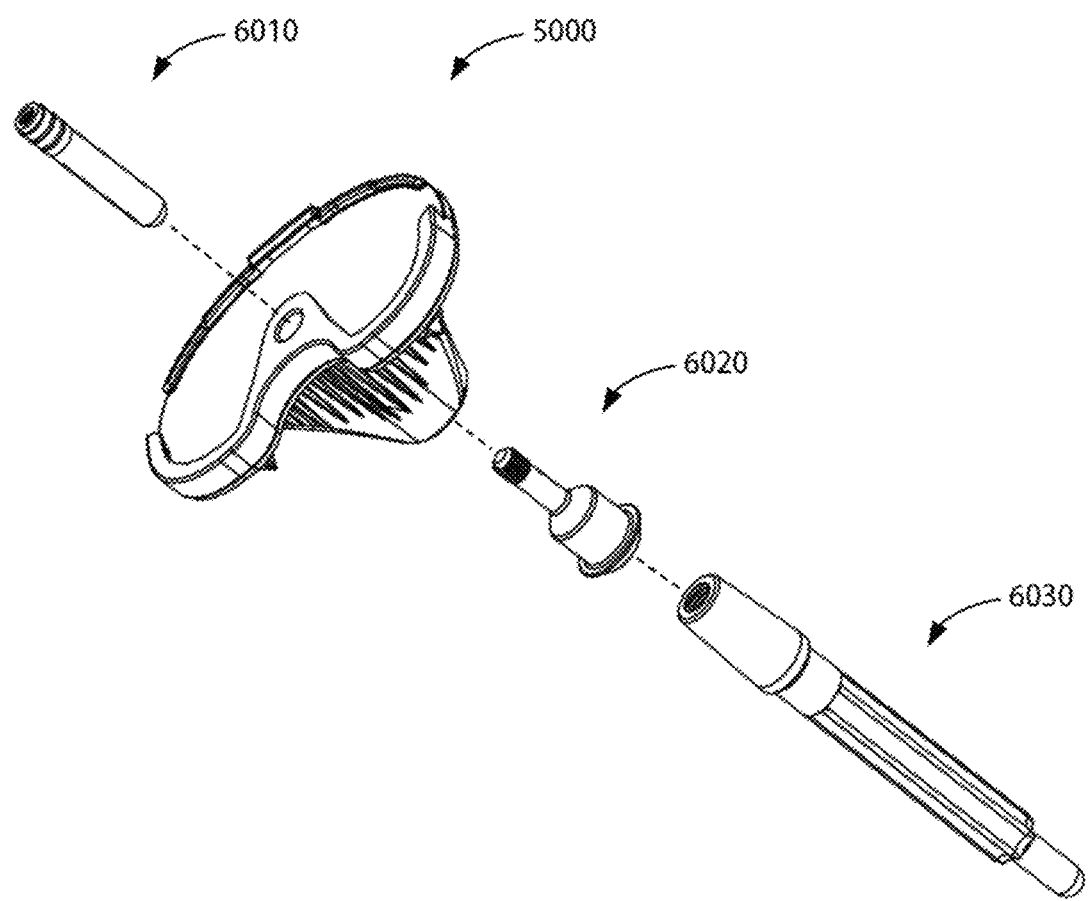
FIG. 39 is an exploded view of a tibial tray mounting system of the disclosure that utilizes the tibial tray of FIG. 38A.

FIGS. 38A-F and 39 illustrate an example tibial tray 5000 that may be used with any of the tibial inserts and femoral components described herein to create various prosthetic knee assemblies, according to embodiments of the present disclosure. In particular, FIG. 38A shows a perspective front view of the tibial tray 5000, FIG. 38B shows a perspective rear view of the tibial tray 5000, FIG. 38C shows an anterior view of the tibial tray 5000, FIG. 12D shows a posterior view of the tibial tray, FIG. 38E shows a bottom view of the tibial tray 5000, FIG. 38F shows a top view of the tibial tray 5000, and FIG. 39 shows an exploded view of an example tibial tray mounting system 6000 that utilizes the tibial tray 5000.

The tibial tray 5000 may generally include a tibial base plate 5001 that is superiorly mounted on top of a keel 5030. The tibial base plate 5001 may have a superior end 5010 configured to receive any of the tibial inserts described herein, and an inferior end 5020 configured to engage a superior surface of a prepared tibia of a patient (not shown). The superior end 5010 of the tibial base plate 5001 may include a posterior lip 5012 and an anterior lip 5014, each configured to couple to and retain any of the tibial inserts described herein. The posterior lip 5012 may have a notch 5016 to permit passage of ligaments and/or other soft tissues. The superior end 5010 of the tibial base plate 5001 may also include a tibial insert retaining aperture 5050 configured to receive a tibial insert retaining rod 6010, which may be used to further couple to and retain a suitable tibial insert to the tibial base plate 5001, as shown in FIG. 39, provided the tibial insert has a corresponding opening in the post of the tibial insert configured to receive the tibial insert retaining rod 6010 (e.g., see the tibial insert shown in FIGS. 22A-F).

The inferior end 5020 of the tibial base plate 5001 may include one or more spikes 5040 configured to penetrate tibial bone to further couple the tibial base plate 5001 to the superior surface of a prepared tibia. The Keel 5030 may also include a medial fin 5032 and a lateral fin 5034 each configured to penetrate tibial bone and provide additional coupling of the tibial tray 5000 to the tibia. Moreover, in some embodiments the Keel 5030 may also include a tibial stem aperture 5036 configured to receive a tibial stem 6030 and/or a stem adapter member 6020 to further couple the tibial tray 5000 to the tibia of a patient (see FIG. 39). The tibial stem 6030 may be configured to penetrate and reside within an intramedullary canal of the tibia to provide increased fixation of the tibial tray 5000 to the tibia.

It will be understood that the tibial tray 5000 and tibial tray mounting system 6000 shown in FIGS. 38A-F and 39 are merely one example of a tibial tray and tibial tray mounting system that may be used with the tibial inserts and femoral components described in the present disclosure and that other tibial trays and tibial tray mounting systems are also contemplated herein.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" may refer to a location on the device that is closest to the clinician using the device and farthest from the patient in connection with whom the device is used when the device is used in its normal operation. Conversely, the term "distal", "bottom", "down" or "downwardly" may refer to a location on the device that is farthest from the clinician using the device and closest to the patient in connection with whom the device is used when the device is used in its normal operation. Moreover, the terms "upper" and "lower", and "top" and "bottom", "front" and "rear" may be used as relative terms herein for ease of description and understanding. It is understood that in embodiments of the disclosure, upper and lower entities may be reversed, as may top and bottom, front and rear.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. An assembly for facilitating orthopedic surgery, comprising:
   a body;
   a drill guide connected to the body; and
   an attachment mechanism connected to the body, the attachment mechanism comprising:
      a first tab;
      a second tab; and
      a handle connected to the first and second tabs such that rotation of the handle about an axis causes the first and second tabs to extend outward from the body to secure the body to an external frame that is configured to be secured to a patient,
   wherein:
      the first and the second tabs each comprise a proximal end, a distal end, and an intermediate section therebetween; and
      the intermediate section is compressible such that the proximal end and the distal end are configured to be translatable.

2. The assembly of claim 1, wherein the drill guide comprises at least one drill guide aperture that extends through the drill guide and through the body.

3. The assembly of claim 2, wherein the drill guide further comprises at least one broach guide aperture that extends through the drill guide and through the body.

4. The assembly of claim 3, wherein the at least one drill guide aperture is in communication with the at least one broach guide aperture.

5. The assembly of claim 1, wherein the proximal ends of the tabs are adjacent to one another, and the distal ends of the tabs extend away from each other.

6. The assembly of claim 5, wherein:
   the proximal ends of the tabs each have a handle attachment feature;
      wherein the handle further comprises tab attachment features complementary to the handle attachment features on each of the tabs; and
      rotation of the handle about the axis causes each of the first tab and the second tab to transition between a retracted position and an extended position, relative to the body.

7. The assembly of claim 6, wherein the proximal ends of the first and second tabs are located within a cavity in the body so that the handle attachment features and/or the tab attachment features extend into the cavity.

8. The assembly of claim 6, wherein:
   at least one of the first tab and the second tab further comprises a stop member;
   the body further comprises an abutment member;
   rotation of the handle causes the stop member to engage the abutment member to retain the at least one of the first tab and the second tab in the extended position.

9. The assembly of claim 1, further comprising the external frame;
   wherein the external frame is a trial component for joint arthroplasty.

10. The assembly of claim 9, wherein:
    the trial component comprises:
       a receiving aperture shaped to receive the body; and
       locking apertures, in communication with the receiving aperture, shaped to receive the distal ends of the first tab and the second tab when the handle is rotated with the body positioned in the receiving aperture.

11. An assembly comprising:
    a body;
    a drill and broach guide comprising:
       a first drill guide aperture;
       a second drill guide aperture;
       a third drill guide aperture;
       a first broach guide aperture intermediate the first drill guide aperture and the second drill guide aperture; and
       a second broach guide aperture intermediate the second drill guide aperture and the third drill guide aperture,
    wherein the second drill guide aperture is intermediate the first broach guide aperture and the second broach guide aperture; and
    a locking mechanism comprising:
       a handle connected to the body such that the handle is rotatable about an axis;
       a first tab having a first proximal end, a first distal end, and a first compressible intermediate section, wherein the first proximal end has a first handle connection feature;
       a second tab having a second proximal end, a second distal end, and a second compressible intermediate section, wherein the second proximal end has a second handle connection feature;
    wherein the handle is movably connected to the first handle connection feature and the second handle connection feature such that, rotation of the handle about the axis extends the first and second tabs outward from the body; and
    wherein:
       at least one of the first tab and the second tab further comprises a stop member;
       the body further comprises an abutment member; and
       rotation of the handle causes the stop member to engage the abutment member to retain the at least one of the first tab and the second tab in an extended position.

12. The assembly of claim 11, wherein the first and second tabs are located within a cavity in the body.

13. The assembly of claim 11 wherein:
    the handle further comprises a circular base and a grip portion, the circular base having a concave surface;
    the body further comprises an aperture, surrounding the axis, extending from a first surface of the body to a second surface of the body, wherein the circular base engages the aperture; and
    the handle is rotatably secured to the base at the aperture by two pins extending into the base proximate an edge of the aperture, so that the pins securely engage the concave surface, allowing the handle to rotate about the axis.

14. The assembly of claim 12, further comprising an external frame;

wherein the external frame is a trial component for joint arthroplasty; and wherein the trial component comprises:

a receiving aperture shaped to receive the body; and locking apertures, in communication with the receiving aperture, shaped to receive the first and second distal ends of the first tab and the second tab when the handle is rotated with the body positioned in the receiving aperture.

15. An assembly for preparing and trialing a bone to receive an implant, the assembly comprising:

a body;

a drill guide connected to the body; and an attachment mechanism connected to the body, the attachment mechanism further comprising:

a first tab;

a second tab; and a handle connected to the first and second tabs;

wherein the assembly is configured to be removably coupled to a trial component by:

rotating the handle such that the first tab and the second tab are first in a retracted position;

positioning the assembly adjacent to the trial component, and rotating the handle such that the first tab and the second tab move to an extended position and engage within corresponding attachment apertures in the trial component, wherein:

at least one of the first tab and the second tab further comprises a stop member and the body further comprises an abutment member; and rotation of the handle causes the stop member to engage the abutment member to retain the at least one of the first tab and the second tab in the extended position or the retracted position.

16. The assembly of claim 15, wherein:

the first and the second tabs each comprise a proximal end, a distal end, and an intermediate section therebetween;

the handle engages the first tab and the second tab at the proximal ends;

the handle is rotatable to transition the first and second tabs to the extended position so that the distal ends of the first and second tabs enter the corresponding attachment apertures in the trial component; and the intermediate section is compressible such that, in response to the distal ends abutting a surface, the intermediate section is compressed to urge the stop member against the abutment member and prevents rotation of the handle.

17. The assembly of claim 15, further comprising the trial component, wherein;

the first and the second tabs each comprise a proximal end, a distal end, and an intermediate section therebetween;

the trial component is designed to facilitate joint arthroplasty; and the trial component comprises:

a receiving aperture shaped to receive the body; and locking apertures, in communication with the receiving aperture, shaped to receive the distal ends of the first tab and the second tab when the handle is rotated with the body positioned in the receiving aperture.

* * * * *